United States Patent
Colonna et al.

(10) Patent No.: US 12,226,382 B2
(45) Date of Patent: Feb. 18, 2025

(54) METHODS FOR TREATING MICROGLIAL DYSFUNCTION

(71) Applicant: Washington University, St. Louis, MO (US)

(72) Inventors: Marco Colonna, St. Louis, MO (US); Tyler Ulland, St. Louis, MO (US)

(73) Assignee: Washington University, St. Louis, MO (US)

( * ) Notice: Subject to any disclaimer, the term of this patent is extended or adjusted under 35 U.S.C. 154(b) by 73 days.

(21) Appl. No.: 17/395,357

(22) Filed: Aug. 5, 2021

(65) Prior Publication Data

US 2021/0393563 A1     Dec. 23, 2021

Related U.S. Application Data

(63) Continuation of application No. 16/030,793, filed on Jul. 9, 2018, now abandoned.

(60) Provisional application No. 62/529,753, filed on Jul. 7, 2017.

(51) Int. Cl.
| | |
|---|---|
| *A61K 31/195* | (2006.01) |
| *A61P 25/28* | (2006.01) |
| *C12Q 1/6827* | (2018.01) |
| *C12Q 1/6883* | (2018.01) |

(52) U.S. Cl.
CPC ............ *A61K 31/195* (2013.01); *A61P 25/28* (2018.01); *C12Q 1/6827* (2013.01); *C12Q 1/6883* (2013.01); *C12Q 2600/156* (2013.01)

(58) Field of Classification Search
CPC ..... A61P 25/28; C12Q 1/6827; C12Q 1/6883; C12Q 2600/156
See application file for complete search history.

(56) References Cited

U.S. PATENT DOCUMENTS

| | | |
|---|---|---|
| 9,045,542 B2 | 6/2015 | Oh et al. |
| 2007/0292403 A1 | 12/2007 | Nivaggioli |
| 2015/0238582 A1 | 8/2015 | Eisenbach-Schwartz et al. |

FOREIGN PATENT DOCUMENTS

WO     2014074942 A1     5/2014

OTHER PUBLICATIONS

Gomez-Nicola et al (The Neuroscientist, 2015; 21(2):169-184) (Year: 2015).*
Ulrich et al (Neuron, 2017;94(2):237-48) (Year: 2017).*
Shibuya, Y. et al., "Inhibiting ACAT1/SOAT1 in Microglia Stimulates Autophagy-Mediated Lysosomal Proteolysis and Increases Abeta1-42 Clearance," J. Neurosci., Oct. 22, 2014, pp. 14484-14501, vol. 34, No. 43.
Snow, R. et al., "Creatine and the creatine transporter: A review," Mol. Cell. Biochem., Aug. 2001, pp. 169-181, vol. 224, No. 1-2, Kluwer Academic Publishers, Netherlands.
Tanzi, R., "The Genetics of Alzheimer Disease," Cold Spring Harb. Perspect. Med., Jul. 25, 2012, pp. 1-10, doi: 10.1101/cshperspect. a006296.
Tejera, D. et al., "Microglia in Alzheimer's Disease: The Good, the Bad and the Ugly," Curr. Alzheimer Res., 2016, pp. 370-380, vol. 13, No. 4.
Turnbull, I. et al., "Cutting Edge: TREM-2 Attenuates Macrophage Activation," J. Immunol., 2006, pp. 3520-3524, vol. 177.
Ulland, T. et al., "TREM2 Maintains Microglial Metabolic Fitness in Alzheimer's Disease," Cell, Aug. 10, 2017, pp. 649-663.e1-e6, vol. 170, No. 4, with Supplemental Figures, 7 pgs.
Ulrich, J. et al., "Altered microglial response to Abeta plaques in APPPS1-21 mice heterozygous for TREM2," Mol. Neurodegener., 2014, pp. 1-9, vol. 9, No. 20.
Vincent, E. et al., "Mitochondrial Phosphoenolpyruvate Carboxykinase Regulates Metabolic Adaptation and Enables Glucose-Independent Tumor Growth," Mol. Cell, Oct. 15, 2015, pp. 195-207, vol. 60.
Wang, Y. et al., "TREM2 Lipid Sensing Sustains the Microglial Response in an Alzheimer's Disease Model," Cell, Mar. 12, 2015, pp. 1061-1071, vol. 160.
Wang, Y. et al., "TREM2-mediated early microglial response limits diffusion and toxicity of amyloid plaques," J. Exp. Med., 2016, pp. 667-675, vol. 213, No. 5.
Werner, M. et al., "Role of PI3K in the generation and survival of B cells," Immunol. Rev., Sep. 2010, pp. 55-71, vol. 237, No. 1, John Wiley & Sons A/S, Singapore.
Woznicki, D. et al., "Formation of a Supplemental Long Time-Constant Reservoir of High Energy Phosphate by Brain In Vivo and In Vitro and Its Reversible Depletion by Potassium Depolarization," J. Neurochem., Jul. 1979, pp. 75-80, vol. 33, No. 1, Pergamon Press Ltd., Great Britain.

(Continued)

*Primary Examiner* — Rayna Rodriguez
(74) *Attorney, Agent, or Firm* — Armstrong Teasdale LLP

(57) ABSTRACT

Among the various aspects of the present disclosure is the provision of methods of treating a microglial dysfunction-associated diseases, disorder, and conditions. The present disclosure provides for a method for treating microglial dysfunction in a subject having a microglial dysfunction-associated neurodegenerative disease comprising administering to a subject a therapeutically effective amount of a microglial rescuing agent. The present disclosure also provides for a method of reversing neuronal damage in a subject having a microglial dysfunction-associated neurodegenerative disease, wherein the microglial dysfunction-associated neurodegenerative disease is characterized by a single nucleotide polymorphisms (SNPs) or mutation in Trem2 or ApoE affecting microglial functions.

9 Claims, 59 Drawing Sheets
(26 of 59 Drawing Sheet(s) Filed in Color)
Specification includes a Sequence Listing.

(56) References Cited

OTHER PUBLICATIONS

Wyss, M. et al., "Creatine and Creatinine Metabolism," Physiol. Rev., Jul. 2000, pp. 1107-1213, vol. 80, No. 3.

Yang, D-S. et al., "Reversal of autophagy dysfunction in the TgCRND8 mouse model of Alzheimer's disease ameliorates amyloid pathologies and memory deficits," Brain, 2011, pp. 258-277, vol. 134.

Yeh, F. et al., "TREM2 Binds to Apolipoproteins, Including APOE and CLU/APOJ, and Thereby Facilitates Uptake of Amyloid-Beta by Microglia," Neuron, Jul. 20, 2016, pp. 328-340, vol. 91.

Yuan, P. et al., "TREM2 Haplodeficiency in Mice and Humans Impairs the Microglia Barrier Function Leading to Decreased Amyloid Compaction and Severe Axonal Dystrophy," Neuron, May 18, 2016, pp. 724-739, vol. 90.

Annesley, T. et al., "Cyclocreatine Phosphate as a Substitute for Creatine Phosphate in Vertebrate Tissues. Energetic Considerations," Biochem. Biophys. Res. Commun., Jan. 10, 1977, pp. 185-190, vol. 74, No. 1.

Annesley, T. et al., "Formation and Utilization of Novel High Energy Phosphate Reservoirs in Ehrlich Ascites Tumor Cells," J. Biol. Chem., Nov. 25, 1978, pp. 8120-8125, vol. 253, No. 22.

Ara, G. et al., "Antitumor Activity of Creatine Analogs Produced by Alterations in Pancreatic Hormones and Glucose Metabolism," In Vivo, Mar.-Apr. 1998, pp. 223-231, vol. 12, No. 2.

Arase, H. et al., "Direct Recognition of Cytomegalovirus by Activating and Inhibitory NK Cell Receptors," Sci., May 17, 2002, pp. 1323-1326, vol. 296, No. 5571.

Atagi, Y. et al., "Apolipoprotein E is a Ligand for Triggering Receptor Expressed on Myeloid Cells 2 (TREM2)," J. Biochem., Oct. 23, 2015, pp. 26043-26050, vol. 290, No. 43.

Bailey, C. et al., "The Triggering Receptor Expressed on Myeloid Cells 2 Binds Apolipoprotein E," J. Biochem., Oct. 23, 2015, pp. 26033-26042, vol. 290, No. 43.

Cho, M-H. et al., "Autophagy in microglia degrades extracellular beta-amyloid fibrils and regulates the NLRP3 inflammasome," Autophagy, Oct. 2014, pp. 1761-1775, vol. 10, No. 10.

Dambuza, I. et al., "C-type lectins in immunity: recent developments," Curr. Opin. Immunol., 2015, pp. 21-27, vol. 32.

Ford, J. et al., "TREM and TREM-like Receptors in Inflammation and Disease," NIH Public Access, Author Manuscript, available in PMC Feb. 1, 2010, pp. 1-17, published in final edited form as: Curr. Opin. Immunol., Feb. 2009, pp. 38-46, vol. 21, No. 1.

Freeman, L. et al., "The pathogenic role of the inflammasome in neurodegenerative diseases," J. Neurochem., 2016, pp. 29-38, vol. 136, Suppl. 1.

Galluzzi, L. et al., "Metabolic Control of Autophagy," Cell, Dec. 4, 2014, pp. 1263-1276, vol. 159.

GEO Accession GSE65067, "Expression data from WT and TREM2 deficient microglia in a mouse model of Alzheimer's disease," NCBI, Jan. 16, 2015, 2 pgs.

GEO Accession GSE98563, "TREM2 is a global regulator of microglia energetic and biosynthetic metabolism during steady state and in Alzheimer's disease," NCBI, May 4, 2017; 2 pgs.

Gold, M. et al., "Beta-amyloid, Microglia and the Inflammasome in Alzheimer's Disease," HHS Public Access Author Manuscript, available in PMC Nov. 1, 2016, pp. 1-9, published in final edited form as: Semin. Immunopathol., Nov. 2015, pp. 607-611, vol. 37, No. 6.

Guerreiro, R. et al., "Genetics of Alzheimer's Disease," Neurotherapeutics, 2014, pp. 732-737, vol. 11.

Hara, T. et al., "Suppression of basal autophagy in neural cells causes neurodegenerative disease in mice," Nature, Jun. 15, 2006, pp. 885-889, vol. 441.

Hedrick, S. et al., "The Fine Specificity of Antigen and Ia Determinant Recognition by T Cell Hybridoma Clones Specific for Pigeon Cytochrome c," Cell, Aug. 1982, pp. 141-152, vol. 30, No. 1.

Heneka, M. et al., "NLRP3 is activated in Alzheimer's disease and contributes to pathology in APP/PS1 mice," HHS Public Access Author Manuscript, available in PMC Oct. 30, 2013, pp. 1-15, published in final edited form as: Nature, Jan. 31, 2013, pp. 674-678, vol. 493, No. 7434.

Heneka, M. et al., "Innate immunity in Alzheimer's disease," Nat. Immunol., Mar. 2015, pp. 229-236, vol. 16, No. 3.

Holtzman, D. et al., "Alzheimer's Disease: The Challenge of the Second Century," Sci. Transl. Med., Apr. 6, 2011, pp. 1-17, vol. 3, No. 77, 77sr1.

Hong, S. et al., "Complement and microglia mediate early synapse loss in Alzheimer mouse models," Sci., May 6, 2016, pp. 712-716, vol. 352, No. 6286.

Huang, Y. et al., "Alzheimer Mechanisms and Therapeutic Strategies," Cell, Mar. 16, 2012, pp. 1204-1222, vol. 148.

Jay, T. et al., "Disease Progression-Dependent Effects of TREM2 Deficiency in a Mouse Model of Alzheimer's Disease," J. Neurosci., Jan. 18, 2017, pp. 637-647, vol. 37, No. 3.

Kim, J. et al., "AMPK and mTOR regulate autophagy through direct phosphorylation of Ulk1," Nat. Cell Biol., Feb. 2011, pp. 132-141, vol. 13, No. 2.

Klionsky, D. et al., "Guidelines for the use and interpretation of assays for monitoring autophagy (3rd edition)," Autophagy, 2016, pp. 1-222, vol. 12, No. 1.

Komatsu, M. et al., "Loss of autophagy in the central nervous system causes neurodegeneration in mice," Nature, Jun. 15, 2006, pp. 880-884, vol. 441.

Kroemer, G. et al., "Autophagy and the Integrated Stress Response," Mol. Cell, Oct. 22, 2010, pp. 280-293, vol. 40.

Kuiper, J. et al., "Creatine Kinase-Mediated ATP supply Fuels Actin-Based Events in Phagocytosis," PLoS Biology, Mar. 2008, pp. 0568-0580, vol. 6, No. 3, e51.

Kurosawa, Y. et al., "Cyclocreatine treatment improves cognition in mice with creatine transporter deficiency," J. Clin. Invest., Aug. 2012, pp. 2837-2846, vol. 122, No. 8.

Laplante, M. et al., "mTOR Signaling in Growth Control and Disease," Cell, Apr. 13, 2012, pp. 274-293, vol. 149.

Lopresti, P. et al., "Direct determination of creatine kinase equilibrium constants with creatine or cyclocreatine as substrate," Biochem. Biophys. Acta, Oct. 19, 1989, pp. 317-320, vol. 998, No. 3.

Lucin, K. et al., "Microglial Beclin 1 Regulates Retromer Trafficking and Phagocytosis and is Impaired in Alzheimer's Disease," Neuron, Sep. 4, 2013, pp. 873-886, vol. 79.

Masliah, E. et al., "Comparison of Neurodegenerative Pathology in Transgenic Mice Overexpressing V717F beta-Amyloid Precursor Protein and Alzheimer's Disease," J. Neurosci., Sep. 15, 1996, pp. 5795-5811, vol. 16, No. 18.

McLaughlin, A. et al., "Specificity of Creatine Kinase for Guanidino Substrates. Kinetic and Proton Nuclear Magnetic Relaxation Rate Studies." J. Biol. Chem., Jul. 10, 1972, pp. 4382-4388, vol. 247, No. 13.

Meyer-Luehmann, M. et al., "Myeloid Cells in Alzheimer's Disease: Culprits, Victims or Innocent Bystanders?," Trends Neurosci., Oct. 2015, pp. 659-668, vol. 38, No. 10.

Netea-Maier, R. et al., "Modulation of inflammation by autophagy: Consequences for human disease," Autophagy, 2016, pp. 245-260, vol. 12, No. 2.

Neumann, H. et al., "Essential role of the microglial triggering receptor expressed on myeloid cells-2 (TREM2) for central nervous tissue immune homeostasis," J. Neuroimmunol., Mar. 2007, pp. 92-99, vol. 184, Nos. 1-2.

Oakley, H. et al., "Intraneuronal beta-Amyloid Aggregates, Neurodegeneration, and Neuron Loss in Transgenic Mice with Five Familial Alzheimer's Disease Mutations: Potential Factors in Amyloid Plaque Formation," J. Neurosci., Oct. 4, 2006, pp. 10129-10140, vol. 26, No. 40.

Office Action dated Feb. 5, 2021 from related U.S. Appl. No. 16/030,793; 17 pgs.

Office Action dated Jun. 19, 2019 from related U.S. Appl. No. 16/030,793; 11 pgs.

Office Action dated Jul. 29, 2020 from related U.S. Appl. No. 16/030,793; 13 pgs.

Office Action dated Dec. 16, 2019 from related U.S. Appl. No. 16/030,793; 17 pgs.

(56) References Cited

OTHER PUBLICATIONS

O'Neill, L. et al., "Immunometabolism governs dendritic cell and macrophage function," J. Exp. Med., 2016, pp. 15-23, vol. 213, No. 1.

Orre, M. et al., "Isolation of glia from Alzheimer's mice reveals inflammation and dysfunction," Neurobiol. Aging, Dec. 2014, pp. 2746-2760, vol. 35, No. 12.

Peng, Q. et al., "TREM2- and DAP12-Dependent Activation of PI3K Requires DAP10 and is Inhibited by SHIP1," Sci. Signal., May 18, 2010, pp. 1-15, vol. 3, No. 122, ra38.

Perry, V. et al., "Microglial priming in neurodegenerative disease," Nat. Rev. Neurol., Apr. 2014, pp. 217-224, vol. 10.

Rowley, G. et al., "On the Specificity of Creatine Kinase. New Glycocyamines and Glycocyamine Analogs Related to Creatine," J. Am. Chem. Soc., Oct. 20, 1971, pp. 5542-5551, vol. 93, No. 21.

Salter, M. et al., "Microglia emerge as central players in brain disease," Nat. Med., Sep. 2017, pp. 1018-1027, vol. 23, No. 9.

Saxton, R. et al., "mTOR Signaling in Growth, Metabolism, and Disease," Cell, Mar. 9, 2017, pp. 960-976, vol. 168.

Sergushichev, A. et al., "GAM: a web-service for integrated transcriptional and metabolic network analysis," Nucleic Acids Res., Apr. 20, 2016, pp. W194-W200, vol. 44.

\* cited by examiner

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 1
cctacacgac gctcttccga tct                                    23

<210> SEQ ID NO 2
<211> LENGTH: 22
<212> TYPE: DNA
<213> ORGANISM: Artificial Sequence
<220> FEATURE:
<223> OTHER INFORMATION: SYNTHESIZED

<400> SEQUENCE: 2
agatcggaag agcacacgtc tg                                     22

<210> SEQ ID NO 3
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 3 cttcccact ggcctcaag                                          19

<210> SEQ ID NO 4
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 4
ccaaaaccca gtgatccagc                                        20

<210> SEQ ID NO 5
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 5
tgctagccgc aggcattac                                         19

<210> SEQ ID NO 6
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 6
gggtgcccaa agaatcagaa c                                      21

<210> SEQ ID NO 7
<211> LENGTH: 18
<212> TYPE: DNA
<213> ORGANISM: Artificial Sequence
<220> FEATURE:
<223> OTHER INFORMATION: SYNTHESIZED

<400> SEQUENCE: 7 ggaggggtt gaggtgtt                                           18

<210> SEQ ID NO 8
<211> LENGTH: 23

```
<212> TYPE: DNA
<213> ORGANISM: Artificial Sequence
<220> FEATURE:
<223> OTHER INFORMATION: SYNTHESIZED

<400> SEQUENCE: 8 tgtgcactttt tattggtctc aag                                    23
```

METHODS FOR TREATING MICROGLIAL DYSFUNCTION

CROSS REFERENCE TO RELATED APPLICATIONS

This application claims the benefit of U.S. application Ser. No. 16/030,793, filed Jul. 9, 2018, which claims the benefit of U.S. Provisional Application No. 62/529,753, filed Jul. 7, 2017, the disclosures of which are hereby incorporated by reference in their entirety.

GOVERNMENTAL RIGHTS

This invention was made with government support under grant numbers AG051485, AG005681, and CA009547 awarded by National Institues of Health. The government has certain rights in the invention.

FIELD OF THE INVENTION

The present disclosure generally relates to compositions and methods of treating a microglial dysfunction associated disease, disorder, or condition.

BACKGROUND

Alzheimer's disease (AD) is the most common cause of late onset dementia. AD lesions in the CNS include plaques of amyloid β (Aβ) peptides and neurofibrillary tangles of hyperphosphorylated tau protein, both linked to synapse loss, neuronal death, and ultimately cognitive decline (Holtzman et al., 2011; Huang and Mucke, 2012). Rare familial AD is due to mutations in amyloid precursor protein (APP) and presenilins (PS) that promote the generation of Aβ peptides prone to aggregation (Tanzi, 2012). However, the risk for common late-onset AD is associated with rare variants of immune receptors expressed on microglia (Guerreiro and Hardy, 2014; Tanzi, 2012). One of these receptors, TREM2, recognizes phospholipids, apoptotic cells, and lipoproteins (Atagi et al., 2015; Bailey et al., 2015; Wang et al. 2015; Yeh et al., 2016). TREM2 transmits intracellular signals through two adapters, DAP12 and DAP10, which recruit protein tyrosine kinase Syk and phosphatidylinositol 3-kinase (PI3-K), respectively (Peng et al., 2010). Arginine-to-histidine variants at position 47 (R47H) or 62 (R62H) of TREM2 increase the risk for sporadic AD and impair binding to phospholipid ligands (Atagi et al., 2015; Bailey et al., 2015; Guerreiro and Hardy, 2014; Wang et al., 2015; Yeh et al., 2016). These variants, as well as TREM2 deficiency and haploinsufficiency in mouse models of AD, moderate microglial proliferation, survival, and accumulation around Aβ plaques, thereby facilitate Aβ plaque buildup and injury of adjacent neurons (Jay et al., 2017; Ulrich et al., 2014; Wang et al., 2015, 2016; Yuan et al., 2016). TREM2 has also been implicated in microglial phagocytosis of dead neurons, damaged myelin, and Aβ plaques (Neumann and Takahashi, 2007; Yeh et al., 2016). However, why defective TREM2 function or expression affects microglia responses to AD lesions is not known.

SUMMARY

Among the various aspects of the present disclosure is the provision of methods of treating a microglial dysfunction-associated diseases, disorder, and conditions.

One aspect of the present disclosure is directed to a method of treating microglial dysfunction in a subject having a microglial dysfunction-associated neurodegenerative disease comprising administering to a subject a therapeutically effective amount of a microglial rescuing agent. In some embodiments, the microglial rescuing agent comprises creatine, a creatine analog, or pharmaceutically acceptable salt thereof.

Another aspect of the present disclosure is directed to a method of treating microglial dysfunction in a subject having a microglial dysfunction-associated neurodegenerative disease comprising administering to a subject a therapeutically effective amount of dectin-1 ligand.

An additional aspect of the present disclosure is directed to a method of suppressing microglial autophagy in a subject having a microglial dysfunction-associated neurodegenerative disease.

In yet another aspect of the present disclosure is directed to a method of reversing neuronal damage in a subject having a microglial dysfunction-associated neurodegenerative disease, wherein the microglial dysfunction-associated jeurodegenerative disease is characterized by a single nucleotide polymorphisms (SNPs) or mutation in Trem2 or ApoE affecting microglial functions.

BRIEF DESCRIPTION OF THE FIGURES

The application file contains at least one drawing executed in color. Copies of this patent application publication with color drawing(s) will be provided by the Office upon request and payment of the necessary fee.

FIG. 1A CD45$^+$, CD11b$^+$, F4/80$^+$ cells were sorted from mouse brains of WT, Trem2$^{-/-}$, 5XFAD, and Trem2$^{-/-}$ 5XFAD mice. TEM images of microglia sorted from 8-month-old WT, Trem2$^{-/-}$, 5XFAD, and Trem2$^{-/-}$ 5XFAD mice. FIG. 1B average number of multivesicular and multilamellar structures/cell (30 cells analyzed/genotype). FIG. 1C confocal images of plaque bearing regions of the cortex (1.1 mm Bregma to 0.8 mm Bregma) of 8-month-old WT, Trem2$^{-/-}$, 5XFAD, and Trem2$^{-/-}$ 5XFAD mice show Iba-1$^{30}$ microglia (red), methoxy X04$^+$ plaques (blue), and LC3 (green). Z-stacks composed of ~30 images taken at 1.2 μm intervals were analyzed. Results are reported as an average of 2 regions of interest (ROI) analyzed. FIG. 1D quantification of the % of microglia that are positive for LC3 puncta. ~150-400 microglia/HPF were analyzed depending on the genotype of the animal. FIG. 1E confocal images of sections from post-mortem brains of R47H$^+$ AD patients and case-matched controls (CV, common variant of TREM2) show Iba-1$^+$ microglia (red), methoxy X04$^+$ plaques (blue), and LC3 (green). 3 ROIs/donor were analyzed and a total of between 400 and 700 microglia/individual were analyzed. FIG. 1F percentages of LC3+ microglia in post mortem specimens of AD patients with different genotypes. *$p<0.005$, **$p<0.001$ by One-way ANOVA with Holm-Sidak's multiple comparisons test. 15 cells from 2 separate mice were visualized for TEM (FIG. 1A, FIG. 1B). Confocal images are representative of 3 female mice per group (FIG. 1C) or 7 R47H, 4 R62H, and 8 case matched AD patients for post-mortem specimens (FIG. 1E). Immunoblots are representative of 3 independent experiments from microglia from 3 separate mice per group (FIG. 1G). Arrowheads indicate multilamellar and multivesicular structures (FIG. 1A) or LC3+ vesicles (FIG. 1C, FIG. 1E). See also FIG. 8 and Table 1.

FIG. 2A microglia were sorted as in FIG. 1A. Immunoblots for LC3I/II, p62, phosphoserine 473 AKT, phospho-AMPK, phospho-NDRG1, phospho-4EBP1, phospho-757 ULK1, and β-actin were performed on cell lysates. FIG. 2B quantification of the LC3II/I ratio in microglia from different genotypes. FIG. 2C single cell suspensions of brain tissue were incubated with MitoTraker Green and stained for $CD45^+$, $CD11b^+$, $F4/80^+$. Representative histograms comparing unstained cells and microglia from 5XFAD and $Trem2^{-/-}$ 5XFAD mice are shown. FIG. 2D quantification of the geometric mean fluorescence intensity (gMFI) of microglia from 3 mice of each genotype is shown. FIG. 2E confocal images of brain sections of 8 month-old WT, $Trem2^{-/-}$, 5XFAD, and $Trem2^{-/-}$ 5XFAD mice were taken as in FIG. 1C. Images depict lba-$1^+$ microglia (red), methoxy X04$^+$ plaques (blue), and cleaved caspase-3 (green). FIG. 2F quantification of the % of LC3$^+$ microglia that are positive for cleaved caspase-3. ** $p<0.001$ by One-way ANOVA with Holm-Sidak's multiple comparisons test (FIG. 2B and FIG. 2F).  $p<0.01$ by Student's T test (FIG. 2D). Immunoblots are representative of 3 independent experiments from microglia from 3 separate mice per group (FIG. 2A). Confocal images are representative of 3 female mice per group (FIG. 2E). See also FIG. 9.

FIG. 3A TEM images of WT and $Trem2^{-/-}$ BMDM cultured overnight in either in 10% or 0.5% LCCM as source of CSF1. FIG. 3B number of multivesicular structures/cell observed in the TEM images 30 cells/genotype and condition were analyzed. FIG. 3C quantification of the LC3II/LC3I ratio in BMDMs from WT and $Trem2^{-/-}$ mice cultured in 10% or 0.5% LCCM overnight or starved in HBSS for 4 hours prior to lysis. FIG. 3D immunoblots for LC3 and actin performed on lysates from WT and $Trem2^{-/-}$ BMDMs cultured in 10% or 0.5% LCCM overnight. Cell were treated with bafilomycin were treated for 5 hours prior to harvest at a final concentration of 0.5 pg/ml. FIG. 3E quantification of LC3II/LC3I ratio in BMDMs from WT and $Trem2^{-/-}$ mice treated as indicated. FIG. 3F-FIG. 3H immunoblots for phosphorylated Akt, NDRG1, S6K, 4EBP1, AMPK, Ulk1 and relative controls. Lysates were from WT and $Trem2^{-/-}$ BMDM cultured overnight in 10% or 0.5% LCCM. FIG. 3I immunoblots for phosphorylated Akt, NDRG1, S6K, 4EBP1, mTOR, total S6K, Akt, and actin performed on lysates from WT and $Trem2^{-/-}$ BMDMs cultured overnight in 10% or 0.5% LCCM followed by the addition of wortmannin for 3 hours prior to harvest. FIG. 3J and FIG. 3K immunoblots for LC3 and phosphoserine 473 AKT in WT and $Trem2^{-/-}$ BMDM cultured in 10% LCCM with the indicated concentration of tunicamycin. Bar graph shows LC3II/LC3I ratios. Error bar represents mean±SEM. *$p<0.05$, $p<0.01$, or **$p<0.001$ by One-way ANOVA with Holm-Sidak's multiple comparisons test (FIG. 3B, FIG. 3C, FIG. 3E, FIG. 3K). Data are representative of at least 3 independent experiments. Arrowheads indicate multilamellar and multivesicular structures (FIG. 3A). See also FIG. 10.

FIG. 4A top most changed metabolites between WT and $Trem2^{-/-}$ BMDM cultured overnight in 10% LCCM. Defined as $p\leq0.01$ and identified in the mouse metabolic network analysis in B. FIG. 4B shiny-genes and metabolites (GAM) output for network analysis combining mass spectrometry and RNA-seq data highlights differences between WT and $Trem2^{-/-}$ BMDM cultured in 10% LCCM. Enzyme-encoding mRNAs and metabolites downregulated or upregulated in $Trem2^{-/-}$ cells vs WT cells are indicated with green or red nodes and connecters, respectively. FIG. 4C top most changed metabolites between WT and $Trem2^{-/-}$ BMDM cultured in 0.5% LCCM. Defined as $p\leq0.01$ and identified in the mouse metabolic network analysis in FIG. 11C. FIG. 4D ATP content of WT and $Trem2^{-/-}$ BMDM cultured in the indicated concentration of LCCM overnight. FIG. 4E extracellular acidification rate (ECAR) and baseline oxygen consumption rate (OCR) by WT and $Trem2^{-/-}$ BMDM cultured overnight in the indicated concentration of LCCM. FIG. 4F and FIG. 4G mitochondrial mass of WT and $Trem2^{-/-}$ BMDM assessed by Mito Tracker Green incorporation and by the ratio of mitochondrial-to nuclear DNA . Error bar represents mean±SEM. *$p<0.05$, $p<0.01$, or **$p<0.001$ by One-way ANOVA with Holm-Sidak's multiple comparisons test (FIG. 4C) or Student's T test (FIG. 4F, FIG. 4G). Data are representative of at least 3 independent experiments. See also FIG. 11.

FIG. 5A ECAR of WT and $Trem2^{-/-}$ BMDM incubated overnight in 0.5% LCCM±10 mM cyclocreatine. FIG. 5B viability of WT and $Trem2^{-/-}$ BMDM incubated for 40 hours in 0.5% LCCM±cyclocreatine. FIG. 5C Immunoblots of LC3, phosphorylated mTOR, phosphorylated Akt, and actin in WT and $Trem2^{-/-}$ BMDM incubated overnight in 0.5% LCCM±5 mM cyclocreatine. FIG. 5D and FIG. 5F LC3, phosphoserine 473 AKT, p62, and actin immunoblots from WT and $Trem2^{-/-}$ BMDM incubated overnight in the indicated concentration of LCCM±depleted zymosan. FIG. 5E Quantification of the LC3II/LC3I ratio derived from immunoblots of LC3 as shown in D. FIG. 5G ATP content of WT and $Trem2^{-/-}$ BMDM cultured in the indicated concentration of LCCM±zymosan overnight. *$p<0.05$ or ****$p<0.001$ by One-way ANOVA with Holm-Sidak's multiple comparisons test (FIG. 5B, FIG. 5E, FIG. 5G). Data are representative of results from at least 3 independent experiments.

Figure 6A:
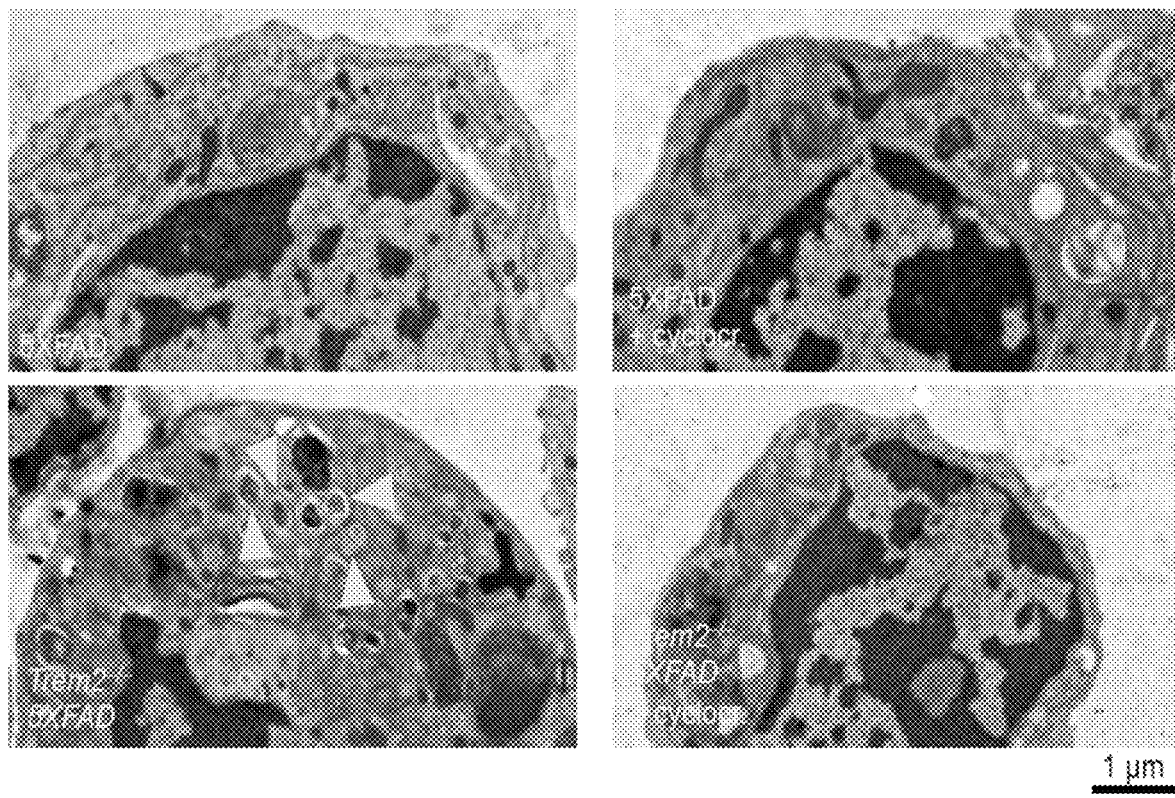
FIG. 6A, FIG. 6B, FIG. 6C, FIG. 6D, FIG. 6E and FIG. 6F depict enhanced energy storage can compensate for TREM2 deficiency in vivo.
Figure 6B:
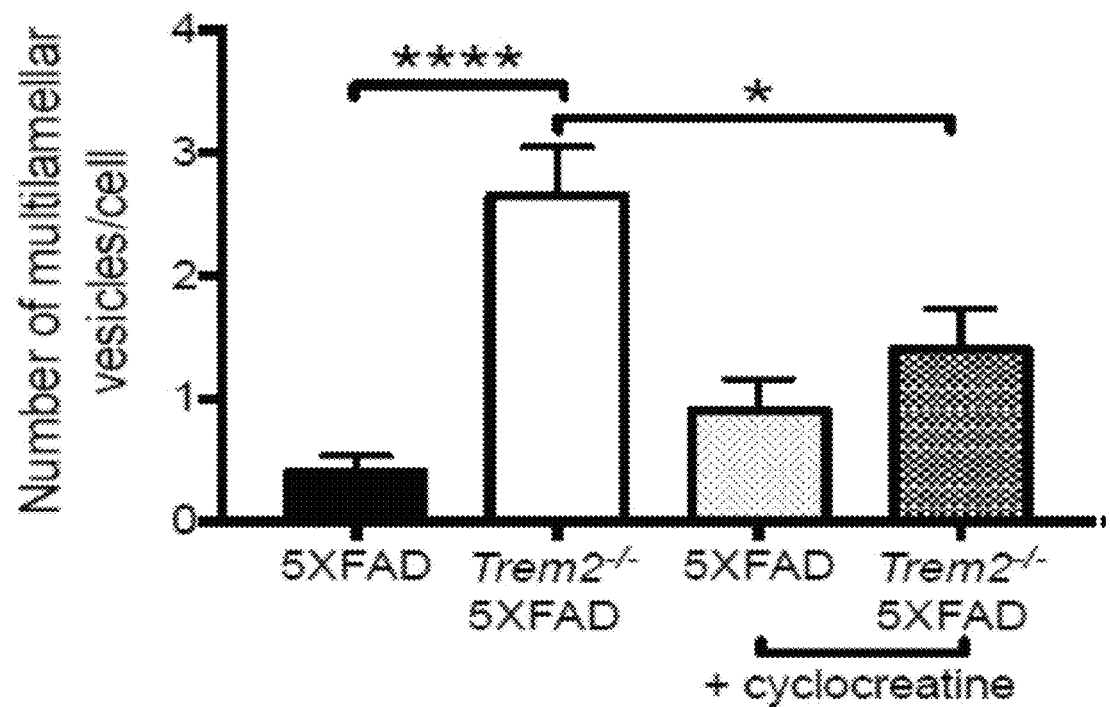
Figure 6C:
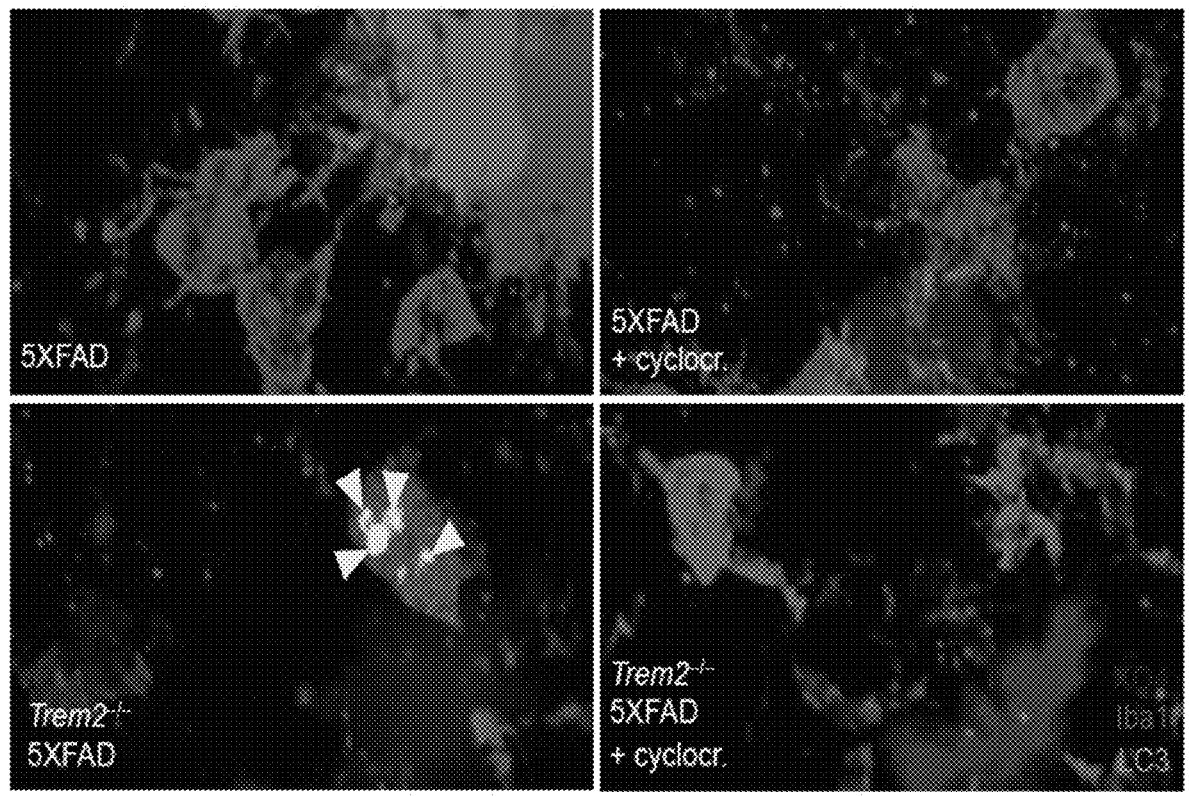
Figure 6D:
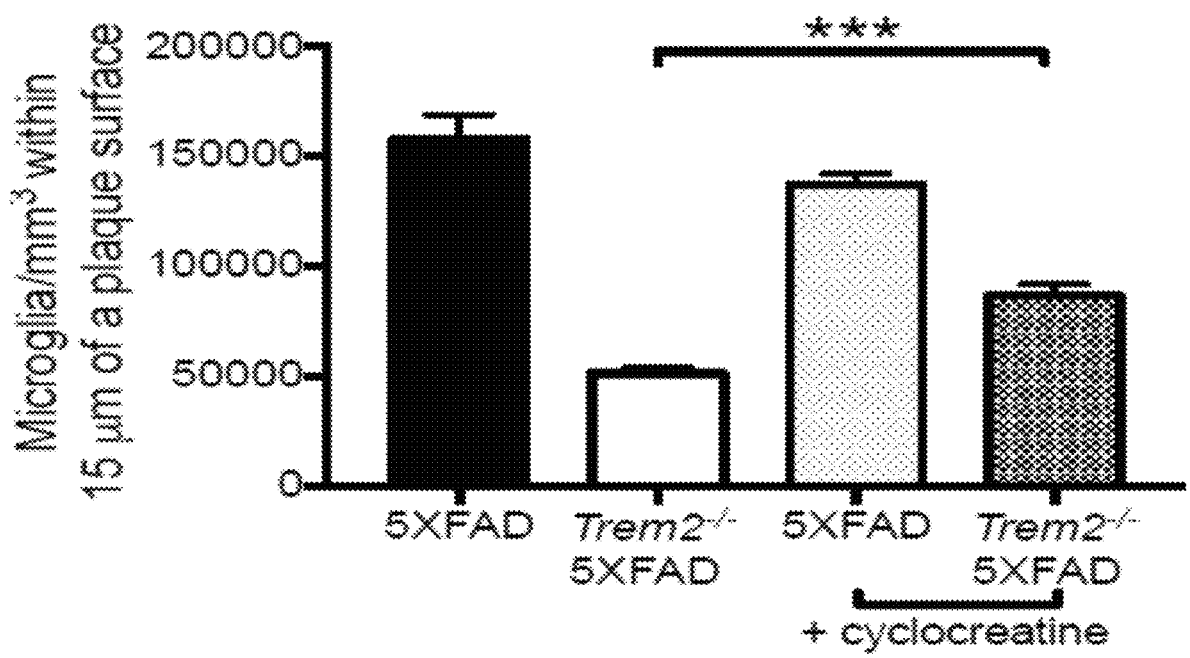
Figure 6E:
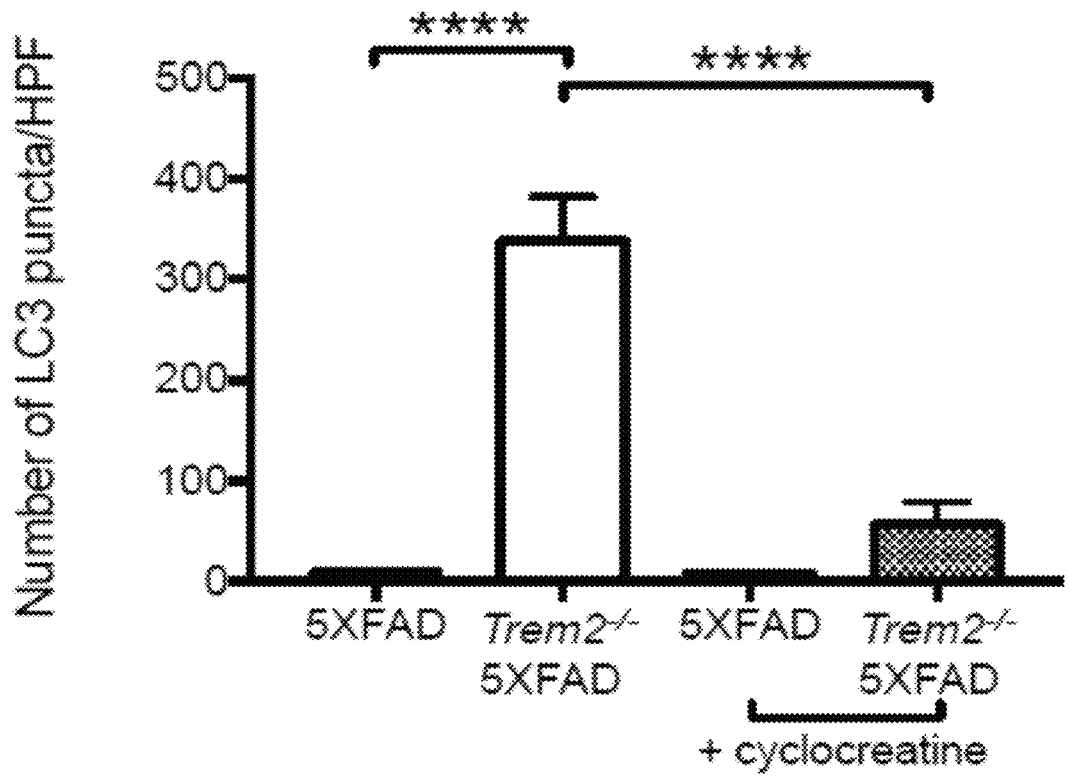
Figure 6F:
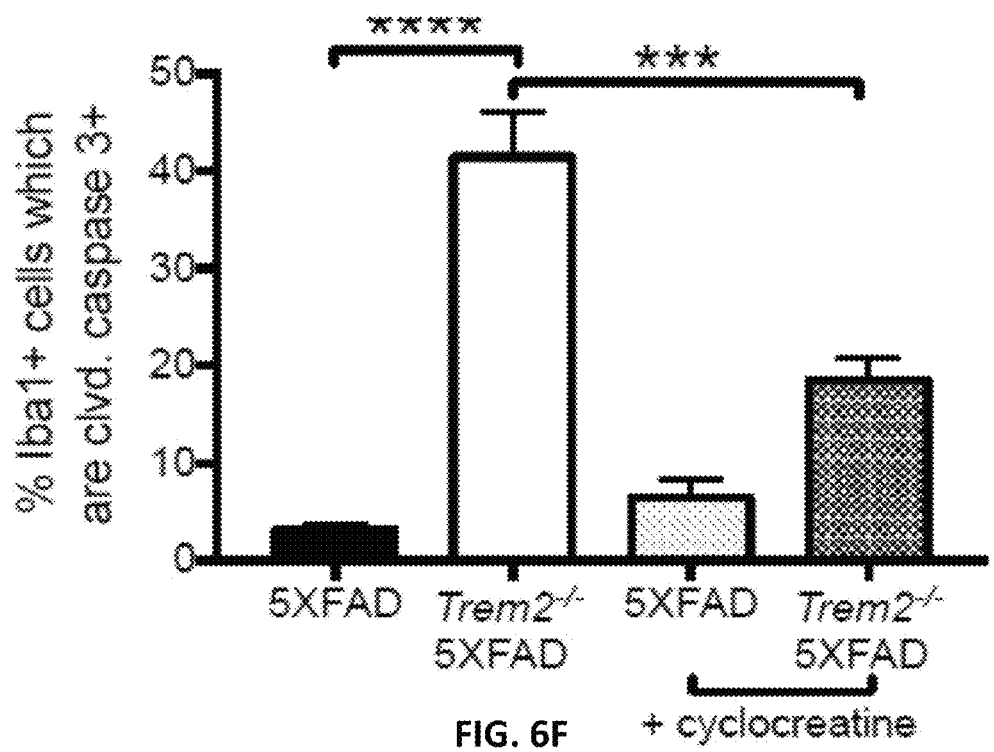

FIG. 6A TEM images of microglia sorted from 8-month-old SXFAD, and $Trem2^{-/-}$ SXFAD mice±cyclocreatine. FIG. 6B quantification of the number of multivesicular and multilamellar structures/cell from A. FIG. 6C confocal images of brain sections of 8-month-old SXFAD, and $Trem2^{-/-}$ SXFAD mice±cyclocreatine show lba-$1^+$ microglia (red), methoxy X04$^+$ plaques (blue), and LC3 (green). FIG. 6D clustering analysis quantifying the number of microglia per mm$^3$ within 15 μm of the surface of plaques. FIG. 6E quantification of the number of LC3 puncta per HPF in the cortexes of the indicated mice. FIG. 6F quantification of the percentage of microglia that were cleaved caspase-3 positive from the indicated mice. *$p<0.05$, *$p<0.005$ and **$p<0.001$ by One-way ANOVA with Holm-Sidak's multiple comparisons test (FIG. 6B, FIG. 6D-FIG. 6F) results pooled from 2 independent experiments representing a total of 5-8 male and female mice per treatment group. Arrowheads indicate multilamellar and multivesicular structures (FIG. 6A) or LC3$^+$ vesicles (FIG. 6C). See also FIG. 12.

Figure 7A:
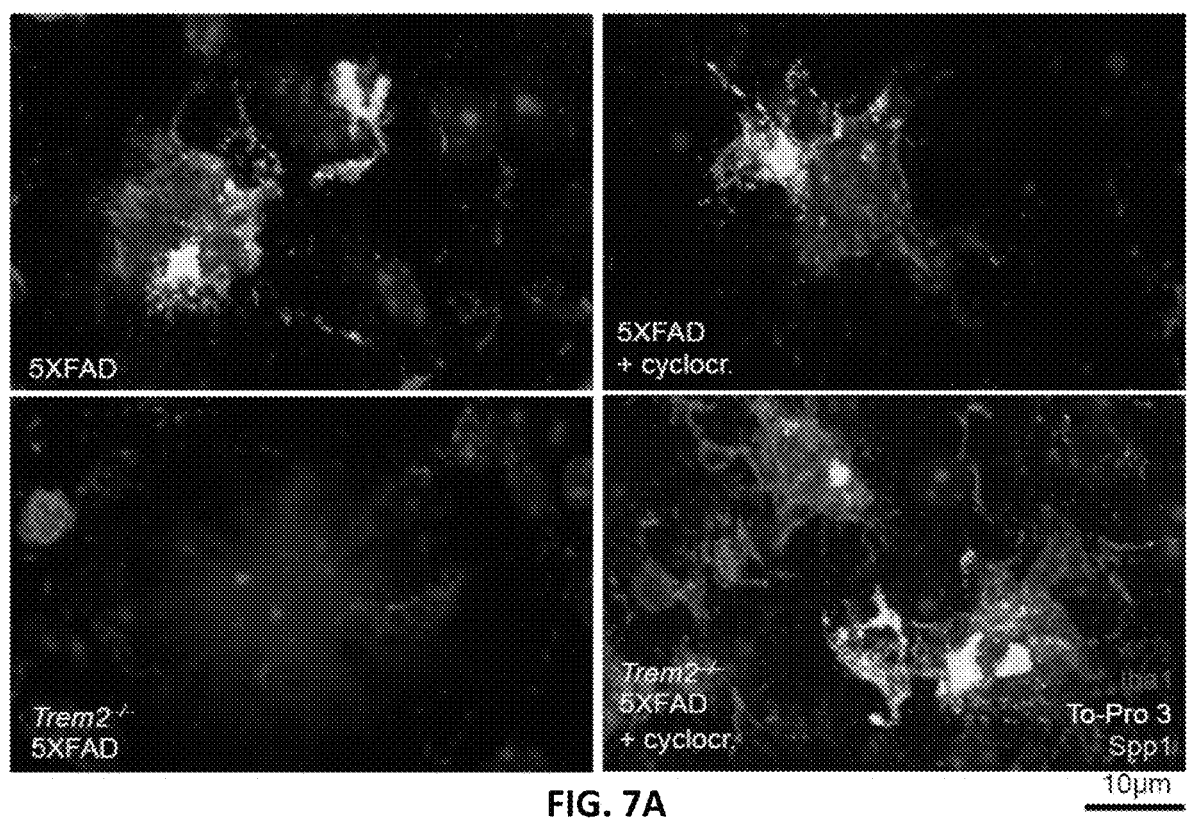
Figure 7B:
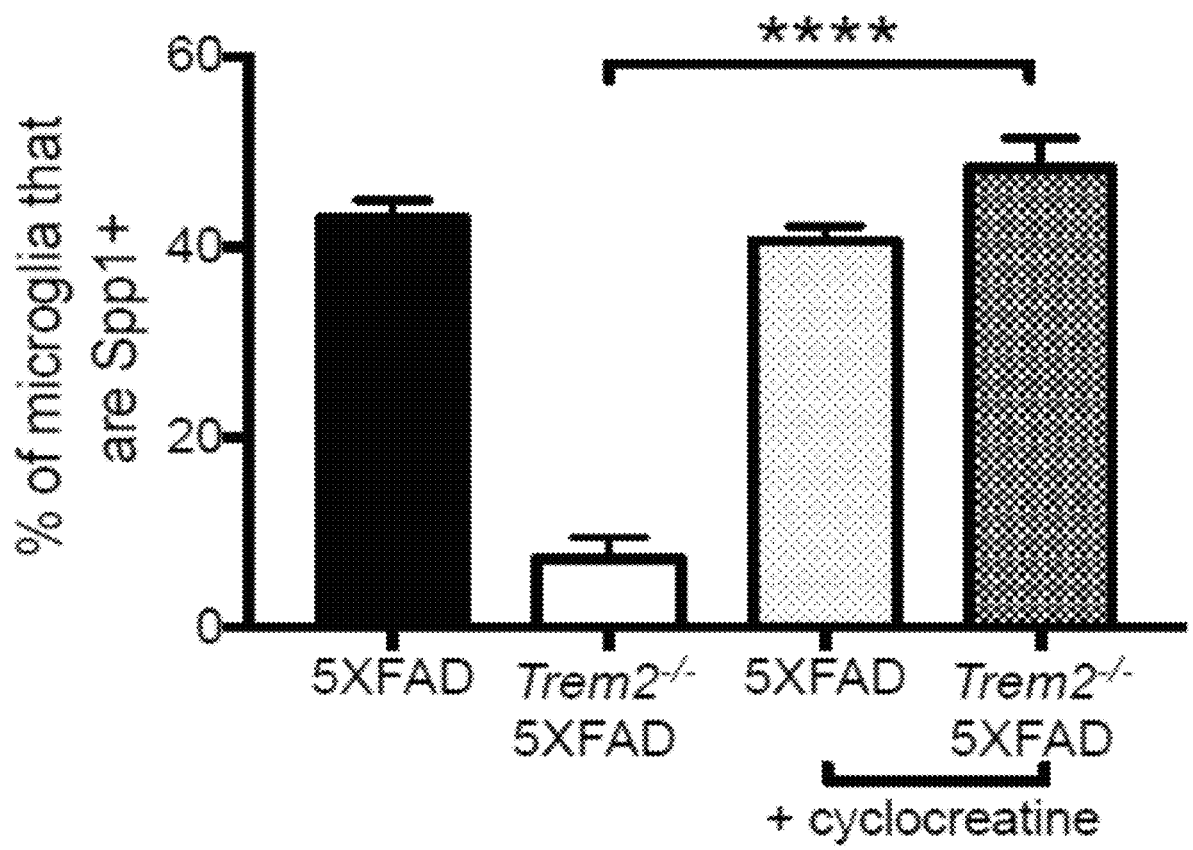
Figure 7C:
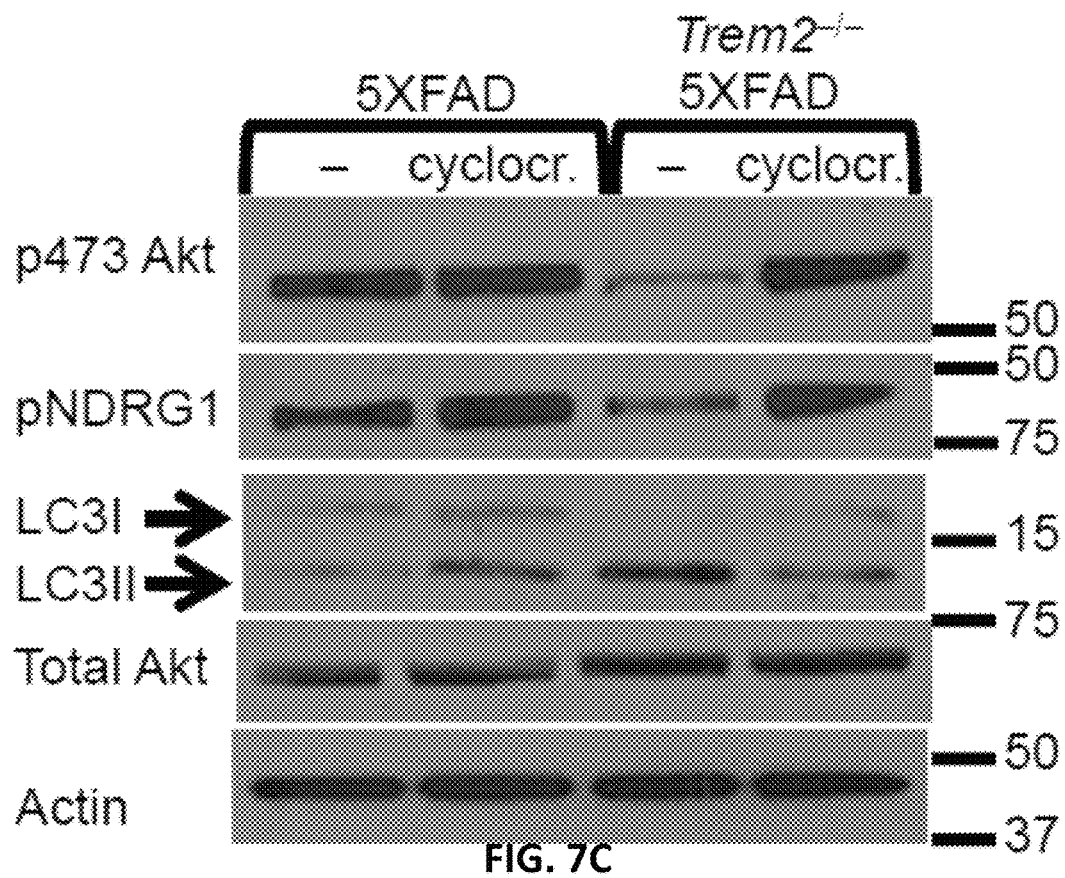
Figure 7D:
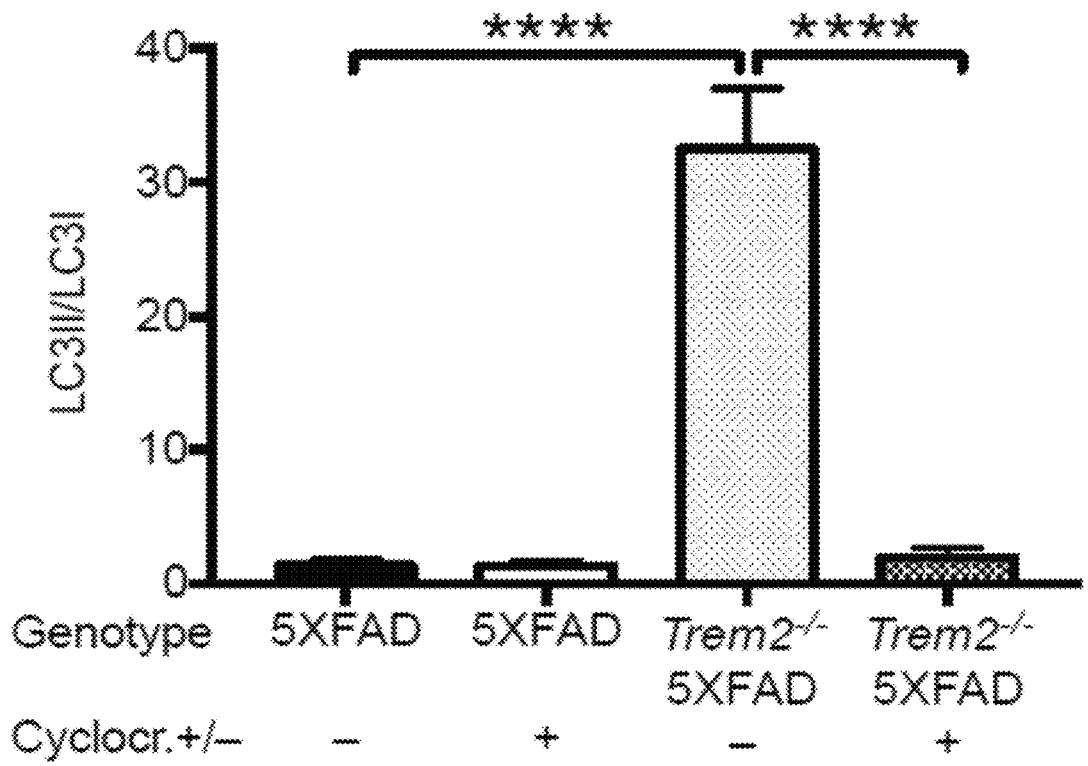
Figure 7E:
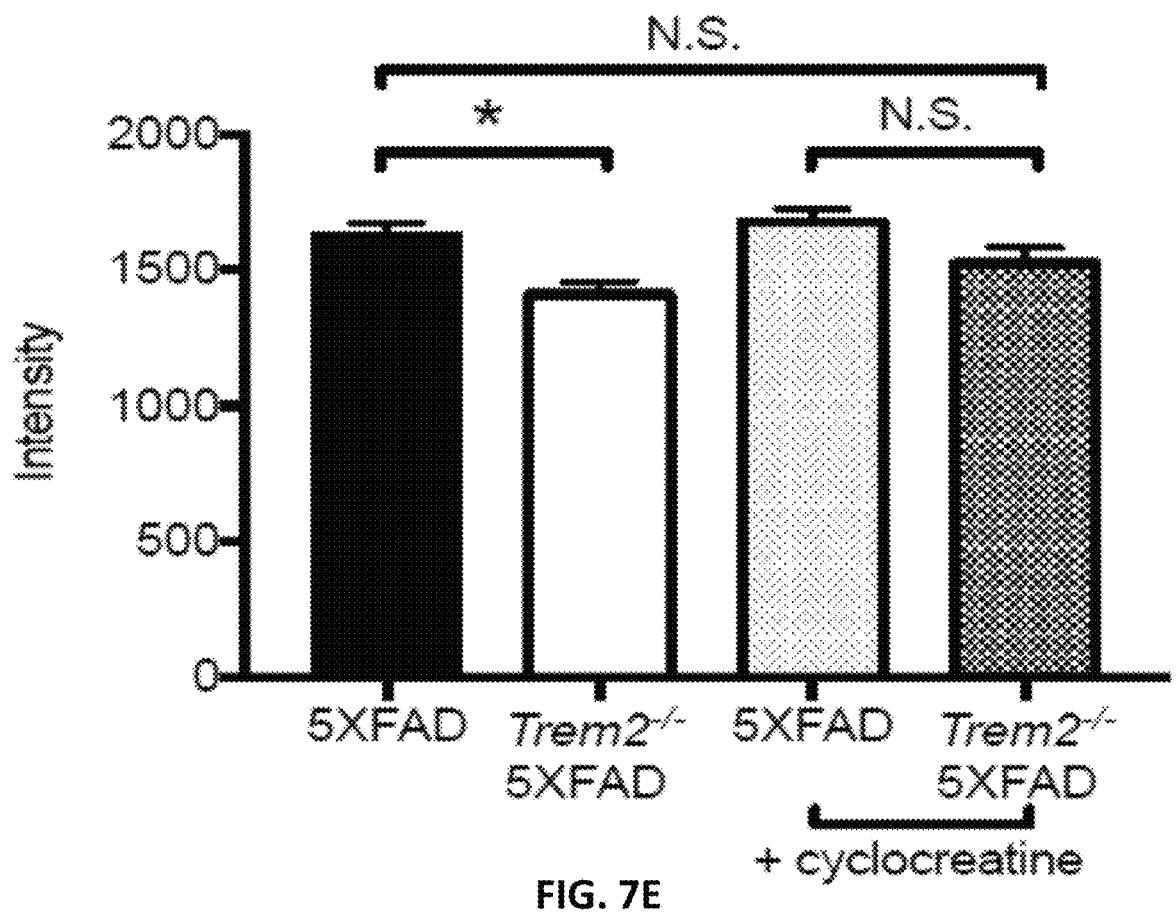
Figure 7F:
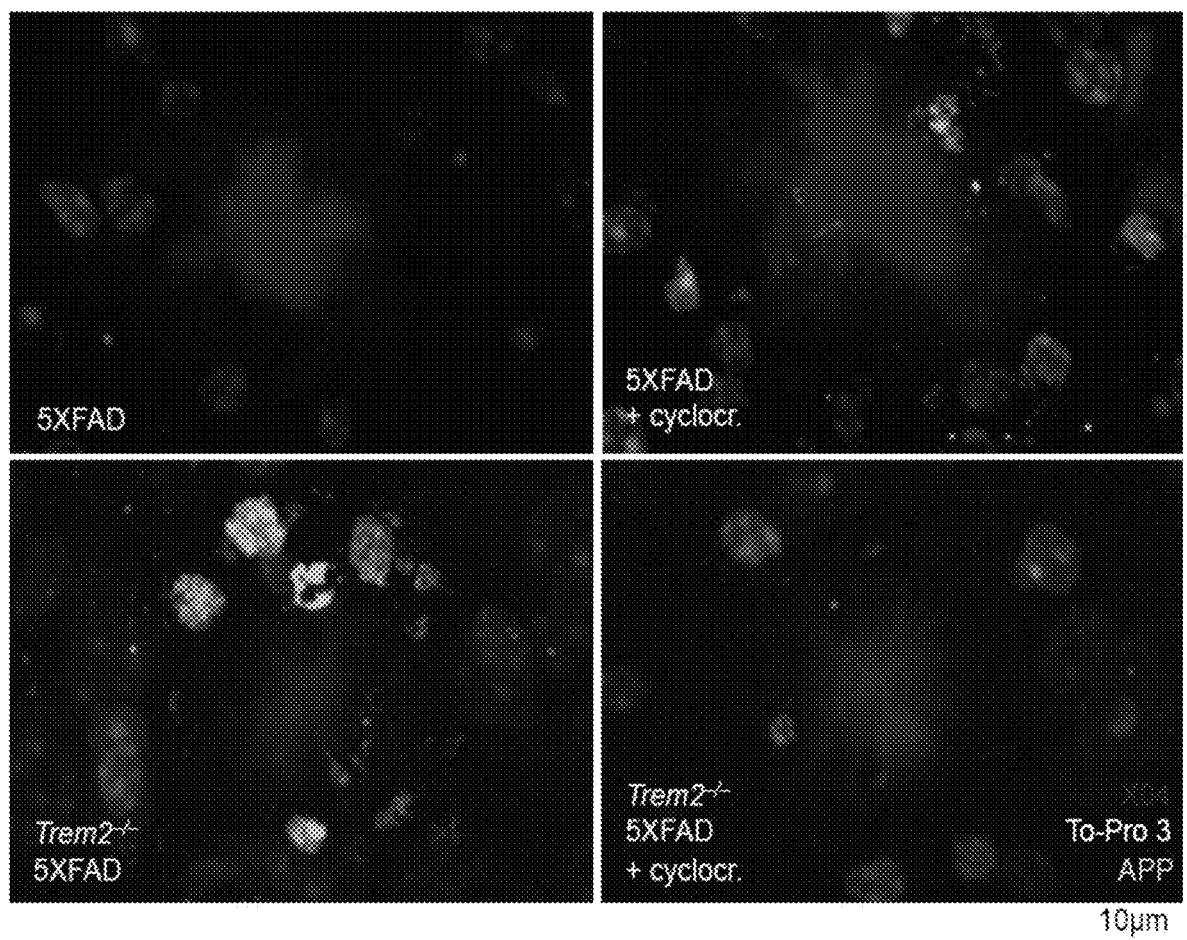
Figure 7G:
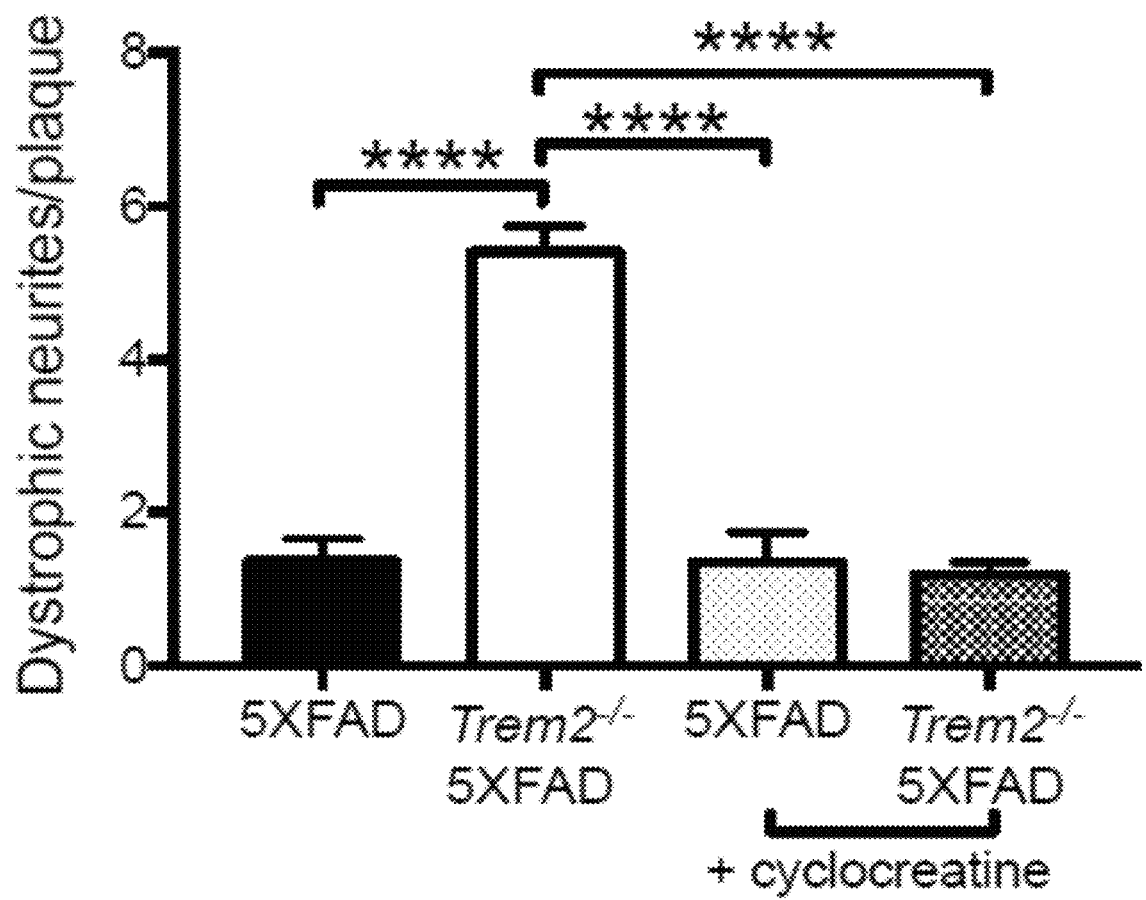

FIG. 7A, FIG. 7B, FIG. 7C, FIG. 7D, FIG. 7E, FIG. 7F and FIG. 7G depict Energy supplementation can compensate for TREM2 deficiency and decrease neuronal damage in vivo. FIG. 7A representative images depicting plaques (X04 in blue), nuclei (To-Pro3 in white), microglia (Iba-1 in red), and Spp1 (in green) staining in cortexes of mice from the indicated genotypes. FIG. 7B quantification of the percentage of microglia that were Spp1$^+$ in the indicated genotypes of mice. Confocal images were taken as in FIG. 1C. FIG. 7C immunoblots performed on lysates of microglia sorted from the indicated genotype and treatment group of mice. Immunoblots for phosphorylated Akt, NDRG1, total LC3, Akt, and actin. FIG. 7D quantification of the LC3II/LC3I ratio observed in immunoblots from 3 mice of each of the indicated genotypes and treatment groups. FIG. 7E average intensity of the plaques observed in the cortexes of mice from the indicated genotypes and treatment groups. FIG. 7F representative images depicting plaques (X04 in blue), nuclei (To-Pro3 in white), and N-terminus APP (green) from the indicated mice and treatment groups. Confocal images were taken as in FIG. 1C. FIG. 7G quantification of the number of dystrophic neurites/plaque in the indicated mice and treatment group. N.S. indicates not significant, *p<0.05, and ****p<0.001 by One-way ANOVA with Holm-Sidak's multiple comparisons test (FIG. 7A, FIG. 7C, FIG. 7D, FIG. 7F) results pooled from 2 independent experiments representing a total of 5-8 male and female mice per treatment group. See also FIG. 12.

Figure 8:
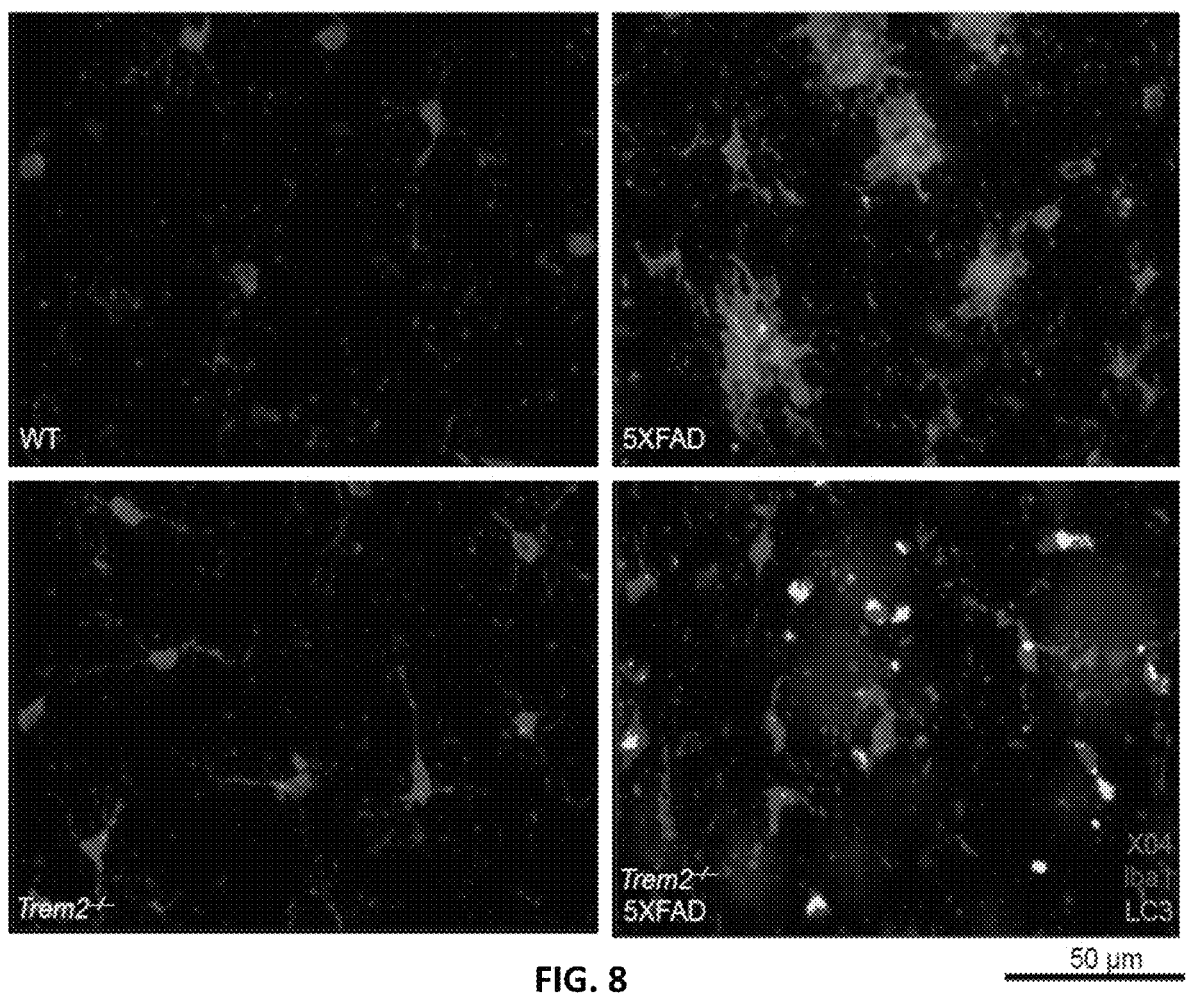

FIG. 8 depicts a wider field of view of LC3 in microglia. Related to FIG. 1. Lower magnification confocal images of cortexes of WT, Trem2$^{-/-}$, 5XFAD and Trem2$^{-/-}$5XFAD mice. Confocal images are representative of 3 female mice per group.

Figure 9A:
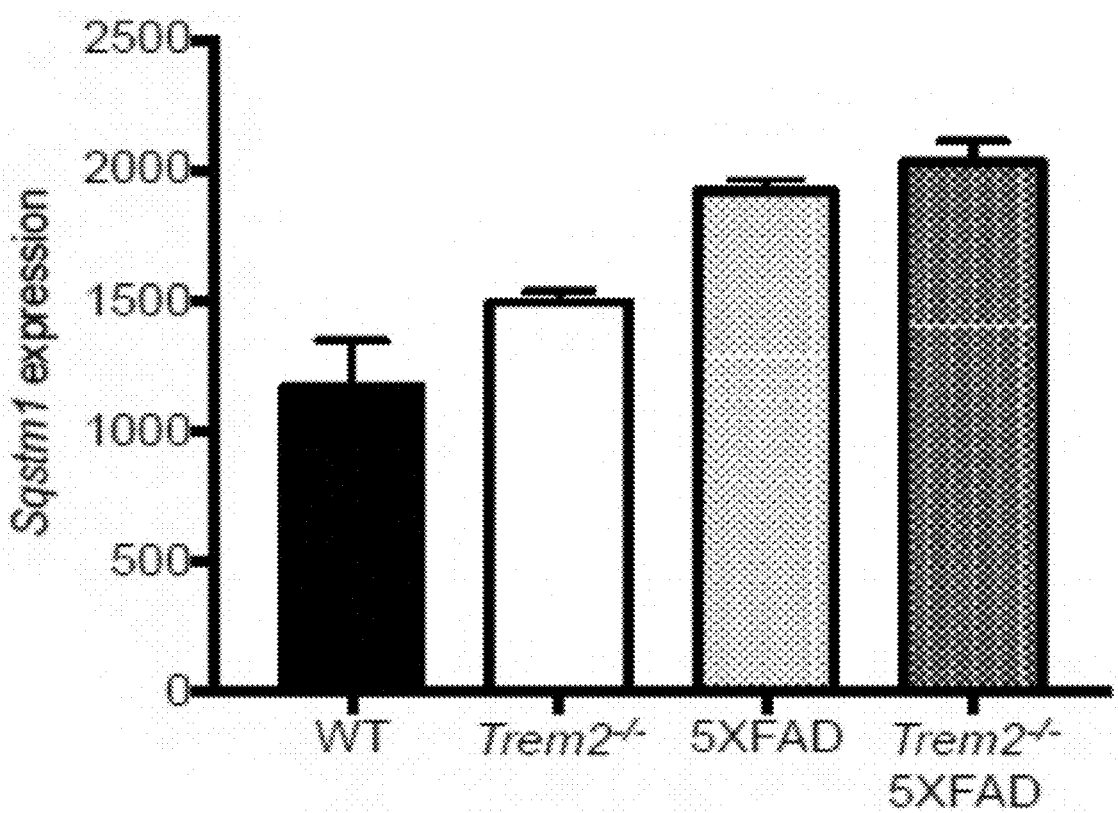
Figure 9B:
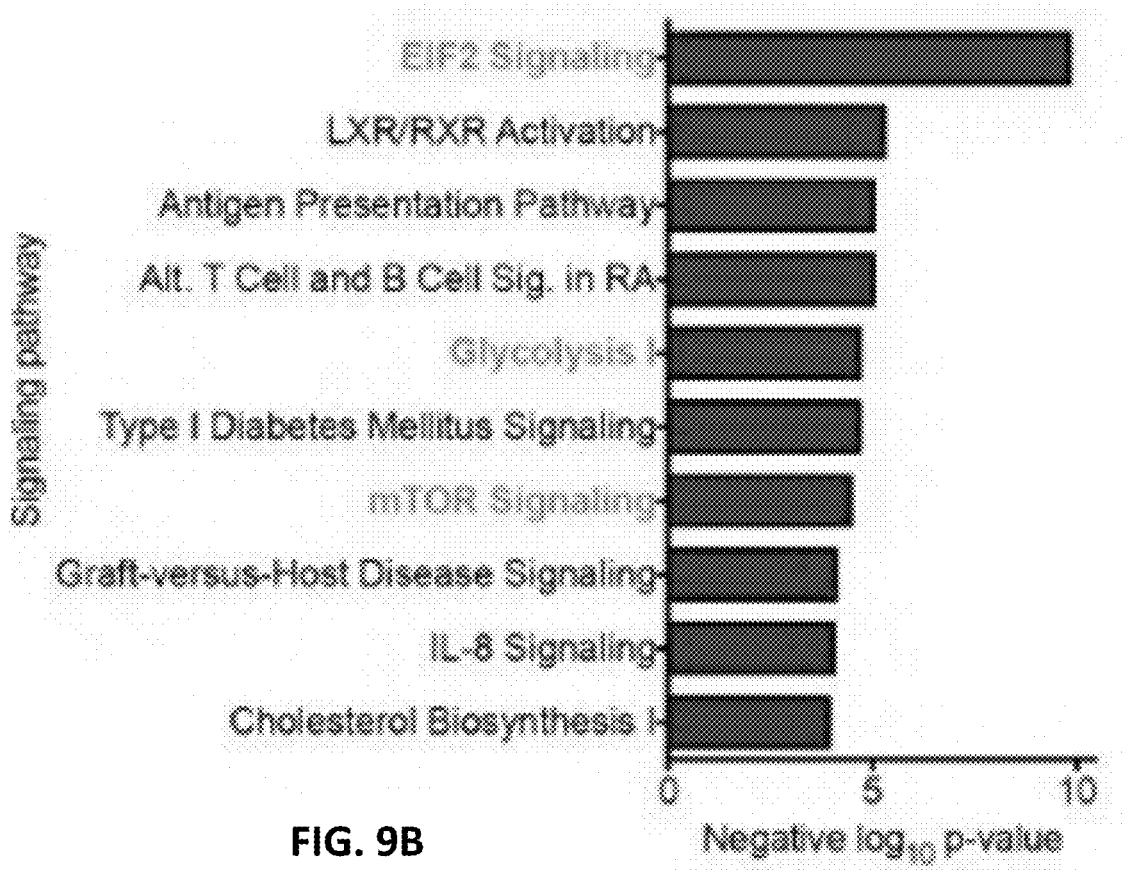
Figure 9C:
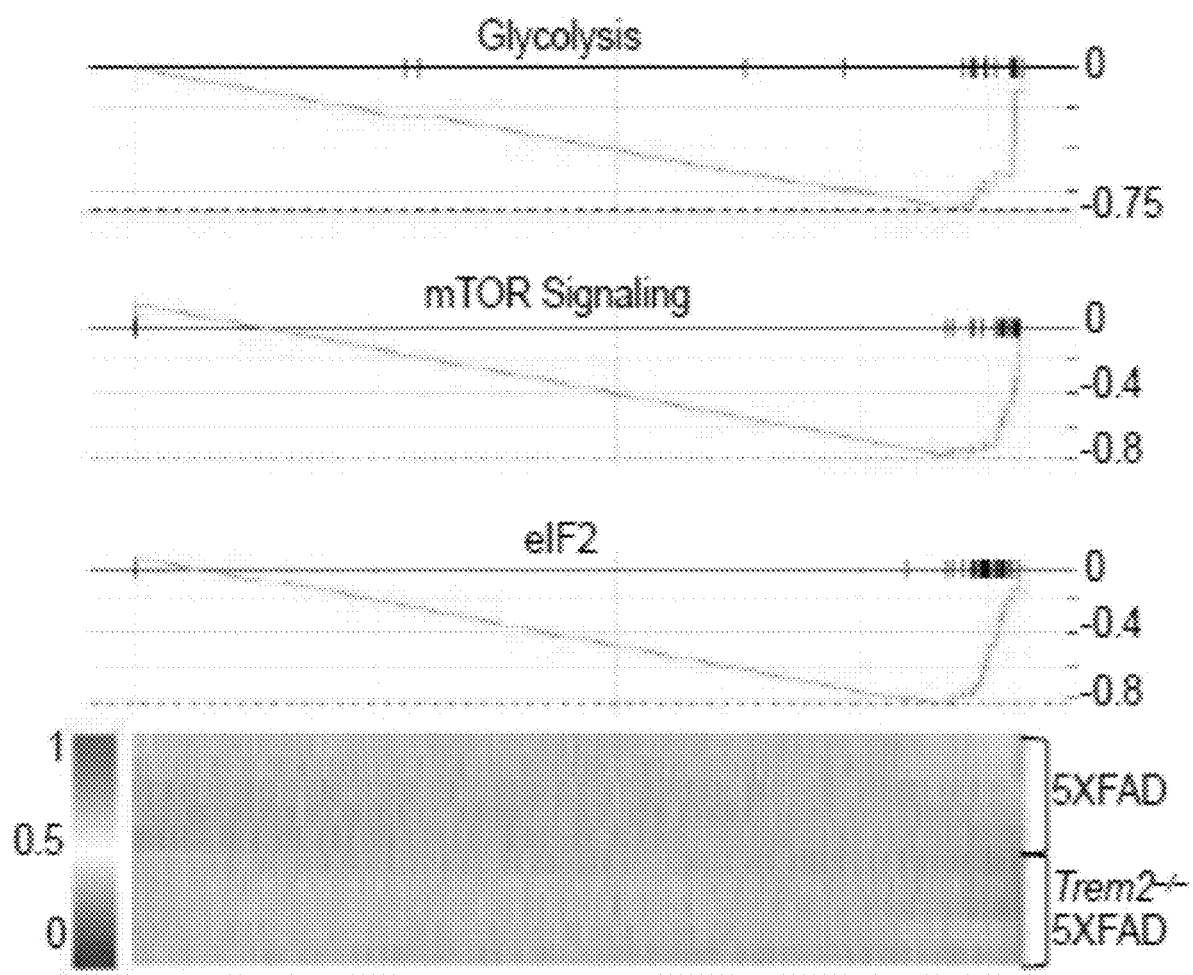
Figure 9D:
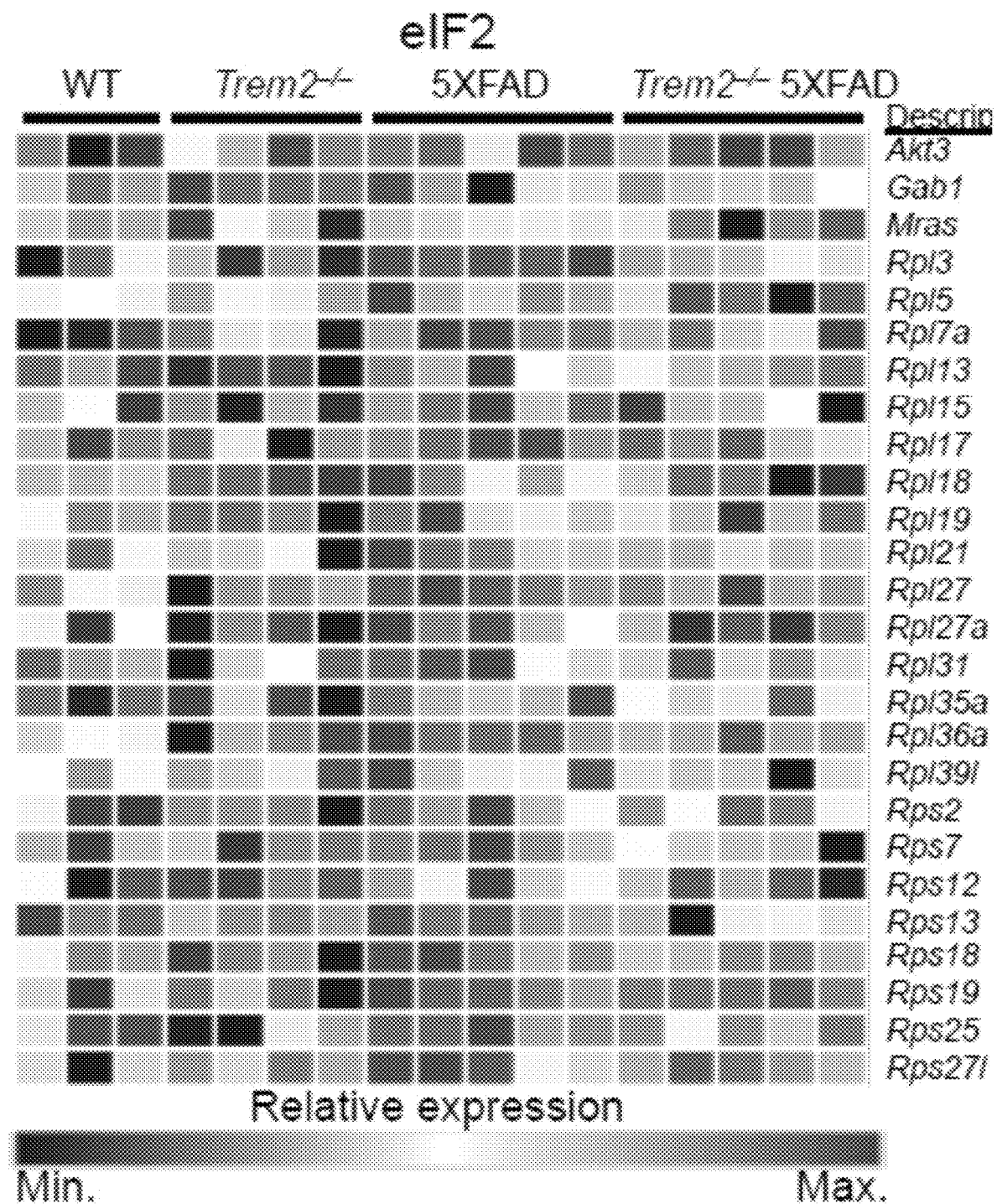
Figure 9E:
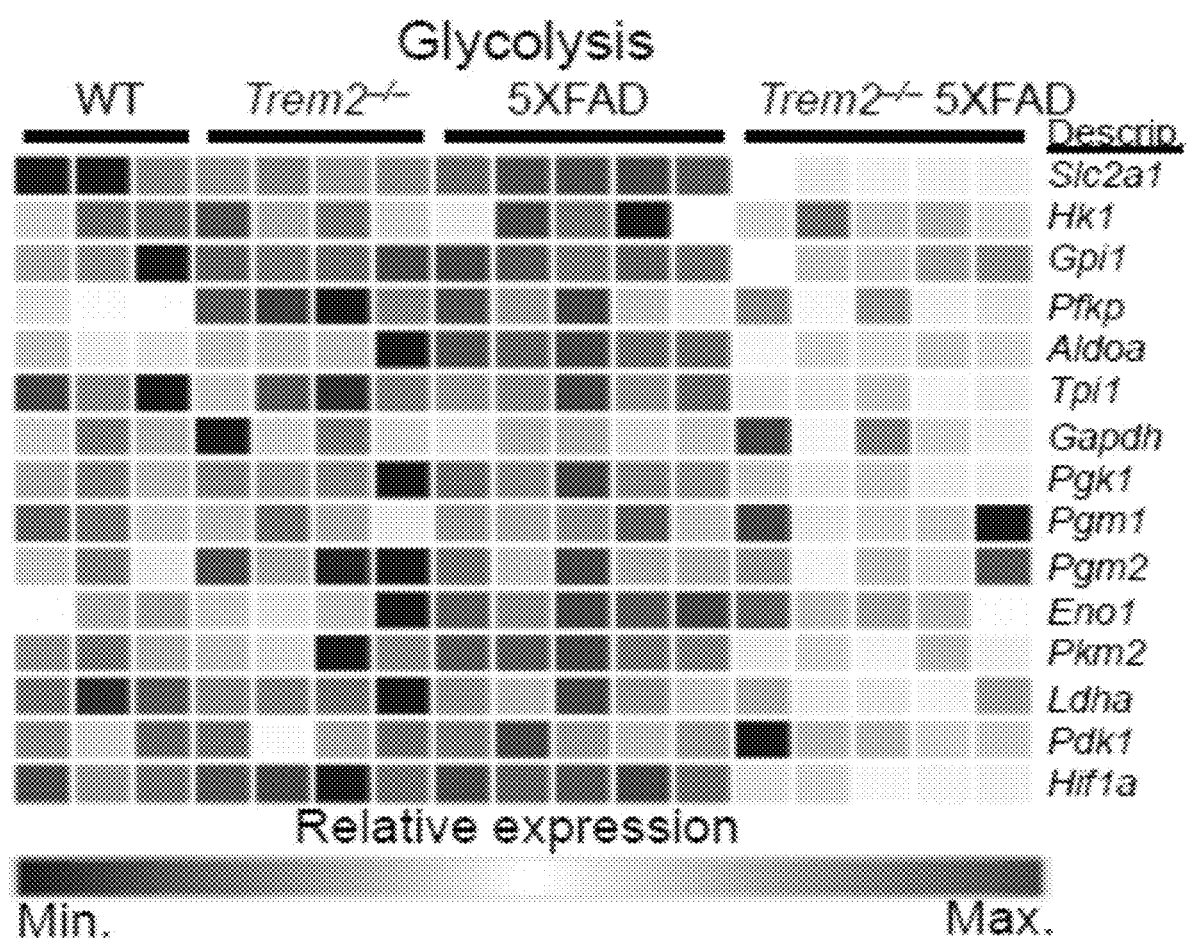
Figure 9F:
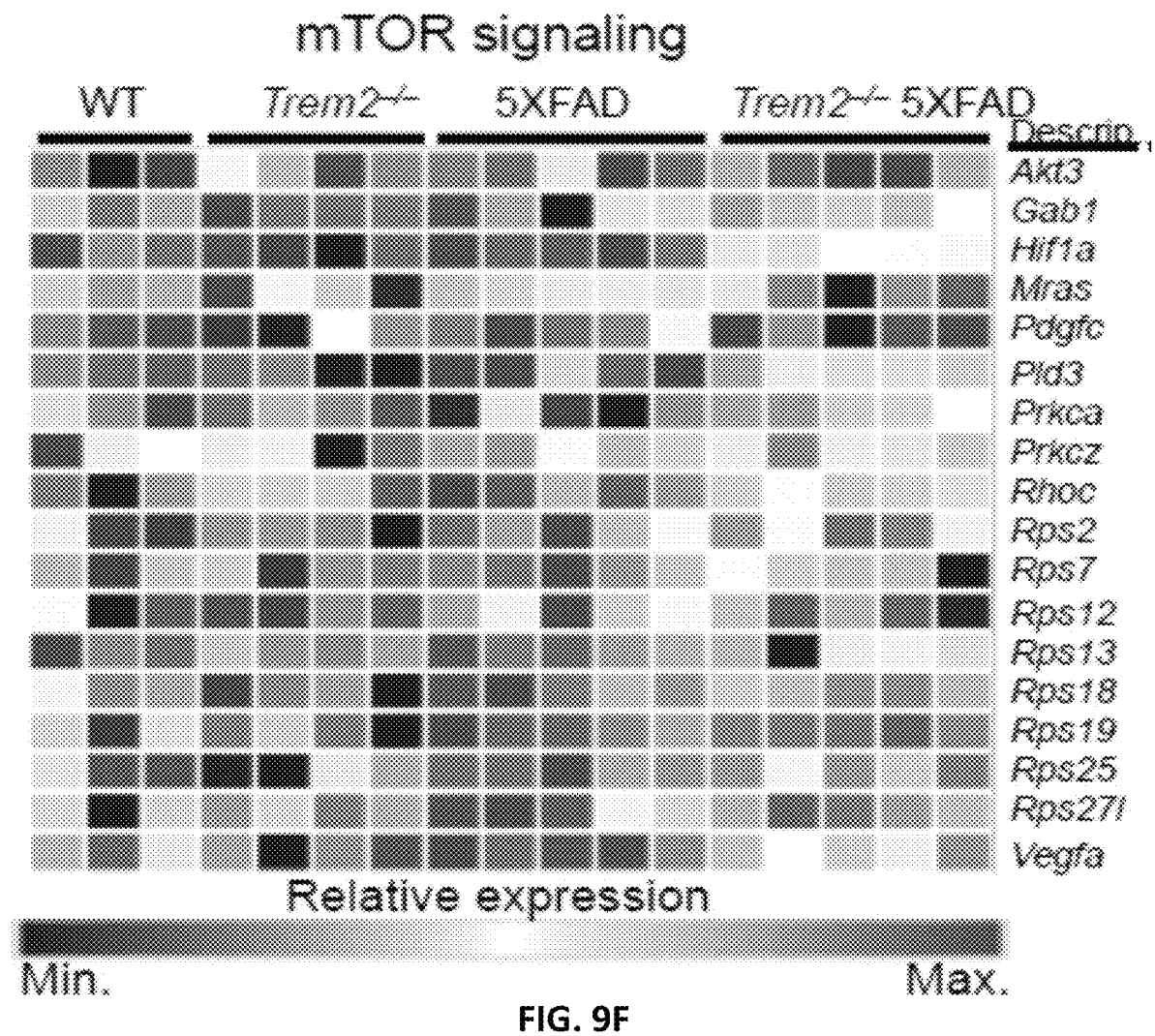
Figure 9G:
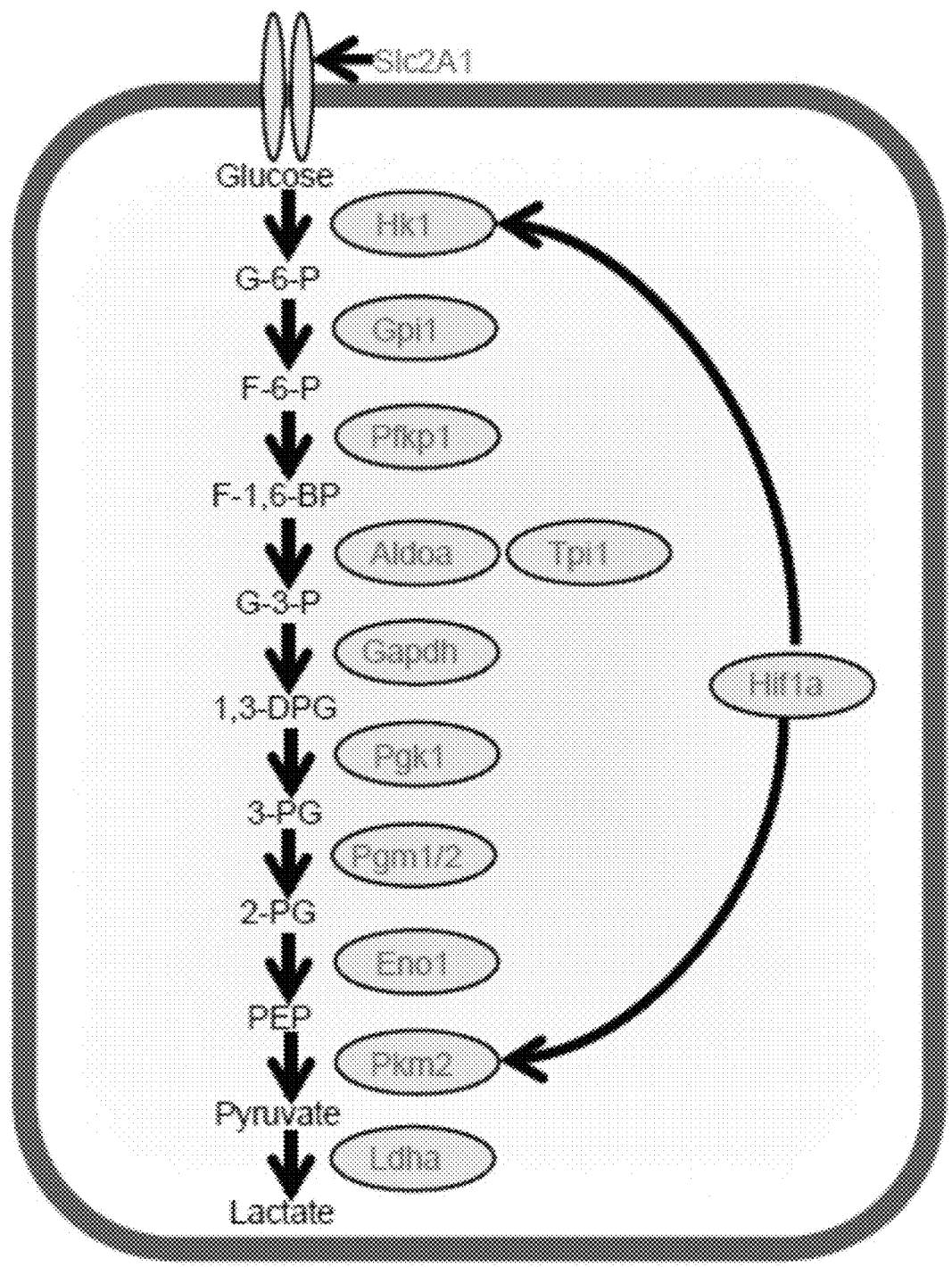
Figure 9H:
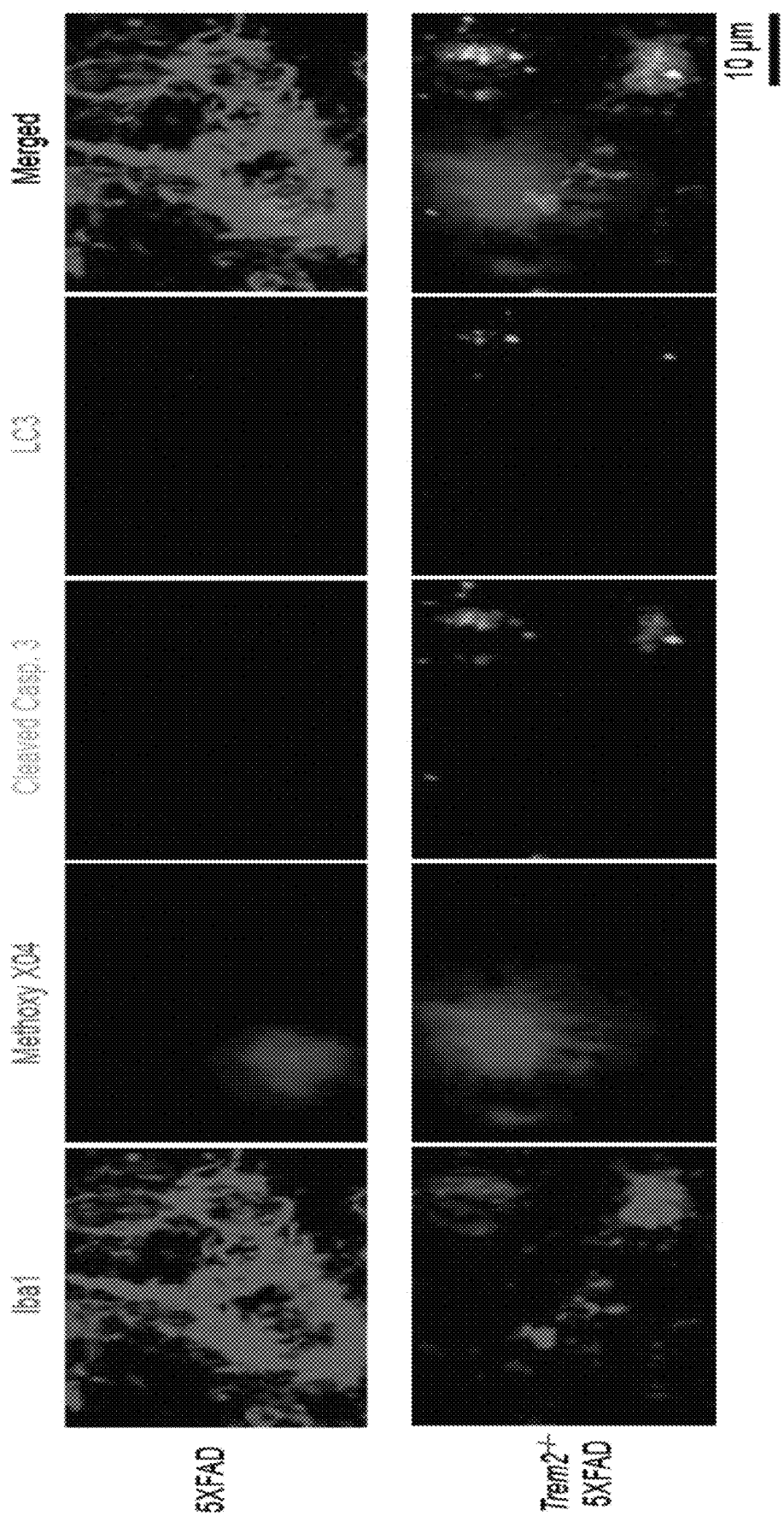
Figure 9I:
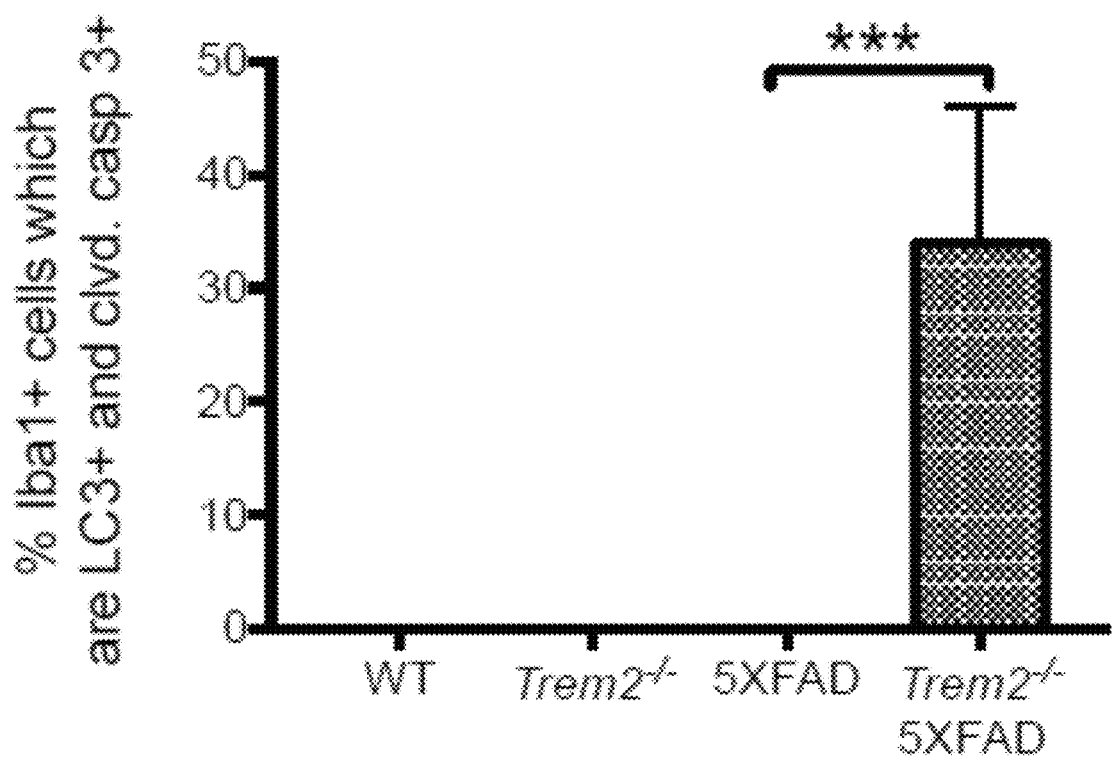

FIG. 9A, FIG. 9B, FIG. 9C, FIG. 9D, FIG. 9E, FIG. 9F, FIG. 9G, FIG. 9H, and FIG. 9I depict TREM2 deficiency in an AD model affects microglia expression of genes involved in metabolic pathways and microglia from Trem2$^{-/-}$ 5XFAD mice undergo more cell death. Related to FIG. 2. FIG. 9A Sqstm1 expression taken from microarrays of sorted microglia from 8 month old WT, Trem2$^{-/-}$, 5XFAD and Trem2$^{-/-}$ 5XFAD mice. FIG. 9B top 10 pathways in IPA analysis of differentially expressed genes from 5XFAD and Trem2$^{-/-}$ 5XFAD microglia. Negative log$_{10}$ p-values are shown. FIG. 9C gene enrichment plots for genes included in the eIF2, glycolysis, and mTOR signaling modules of IPA. Plots were generated utilizing gene-set enrichment analysis (GSEA) software. FIG. 9D-FIG. 9F heat maps comparing WT, 5XFAD, Trem2$^{-/-}$, and Trem2$^{-/-}$ 5XFAD microglia for expression of genes included in the eIF2, glycolysis and mTOR signaling pathways. FIG. 9G illustration of the glycolytic pathway: proteins indicated in red correspond to genes upregulated in 5XFAD but not Trem2$^{-/-}$ 5XFAD microglia compared to WT microglia. FIG. 9H mosaic of images depicting representative images of microglia (Iba1 red), plaques (methoxy-X04 blue), cleaved caspase-3 (aqua), LC3 (green), and total merged images from a 5XFAD and a Trem2$^{-/-}$ 5XFAD animal. FIG. 9I quantification of the percentage of microglia that are both LC3 and cleaved caspase-3 positive. Microarray data represents analyses of microglia sorted from 3 WT, 4 Trem2$^{-/-}$, 5 5XFAD, and 5 Trem2$^{-/-}$ 5XFAD mice (FIG. 9A-FIG. 9G). Confocal images are representative of 3 female mice per group (FIG. 9H). ***p<0.005 by One-way ANOVA with Holm-Sidak's multiple comparisons test (FIG. 9I).

Figure 10A:
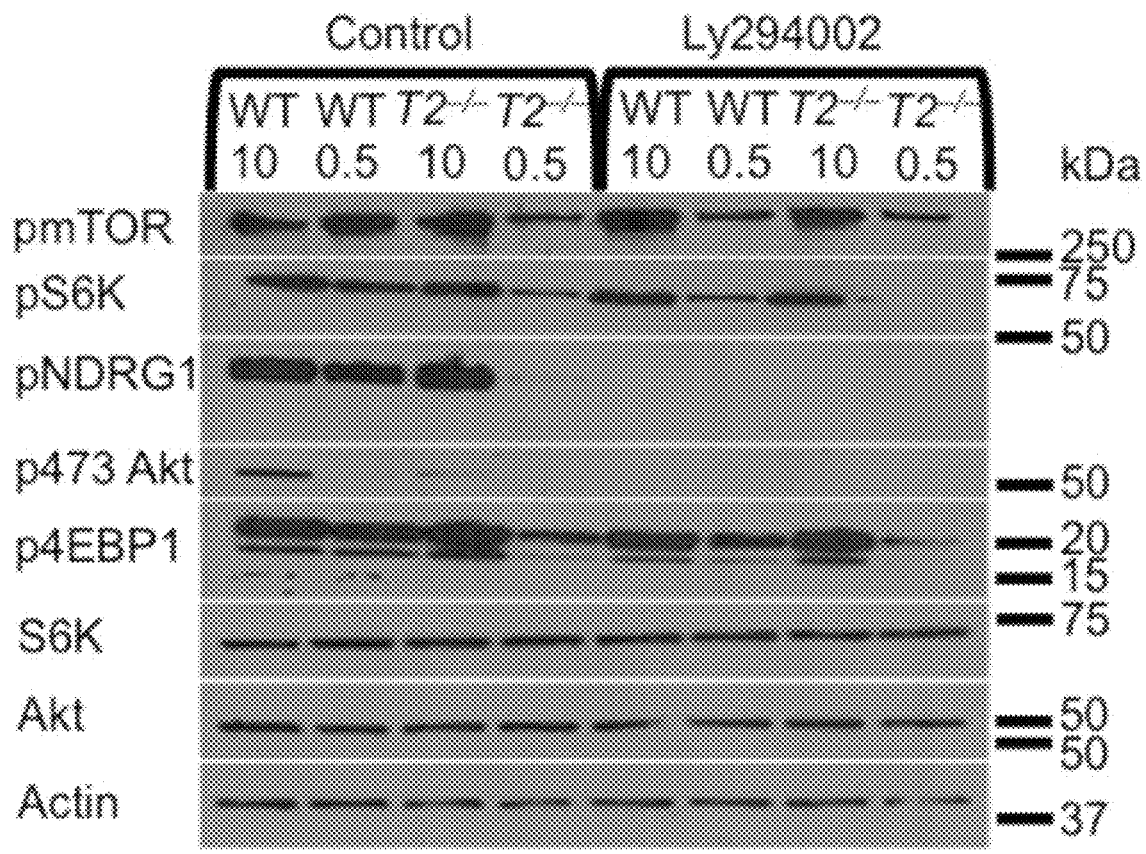
Figure 10B:
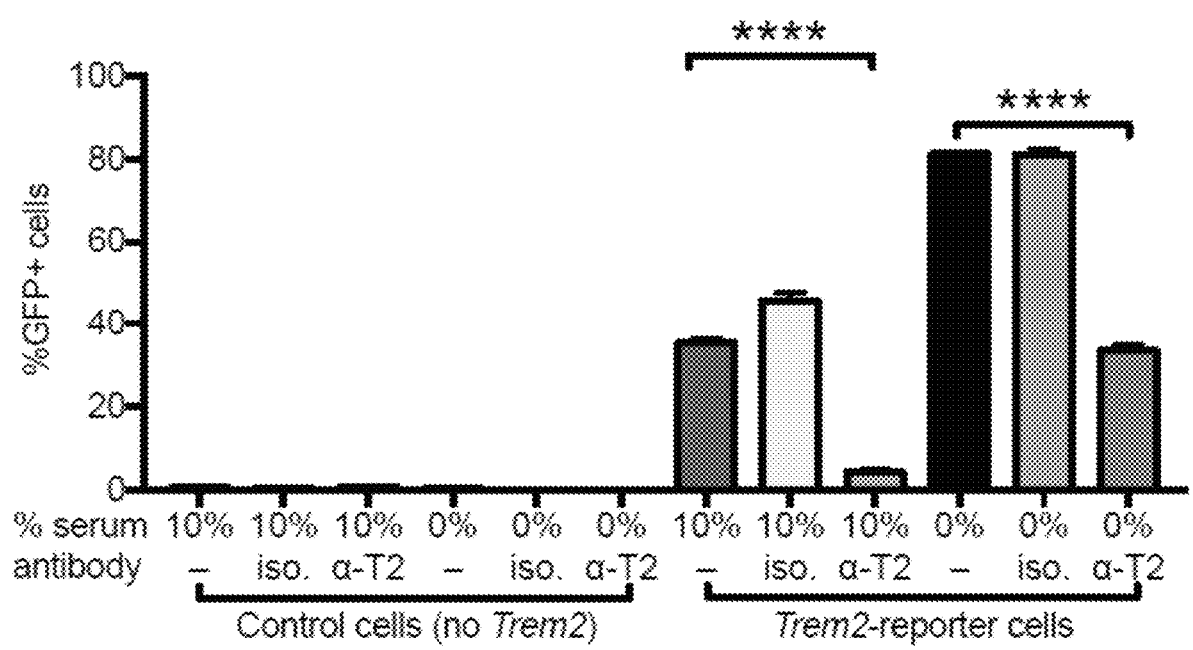

FIG. 10A and FIG. 10B depict Trem2 is activated in vitro and contributes to PI3K-dependent mTOR activation. Related to FIG. 3. FIG. 10A immunoblots for phosphorylated Akt, NDRG1, S6K, 4EBP1, mTOR, total S6K, Akt, and actin performed on lysates from WT and Trem2$^{-/-}$ BMDMs cultured overnight in 10% or 0.5% LCCM followed by the addition of Ly294002 for 3 hours prior to harvest. FIG. 10B reporter cell assay assessing TREM2 activation in reporter cell line incubated at optimal and low serum conditions with or with soluble anti-TREM2. N.S. indicates not significant and ****p<0.001 by One-way ANOVA with Holm-Sidak's multiple comparisons test (FIG. 10B). Results are representative of at least 3 independent experiments.

Figure 11A:
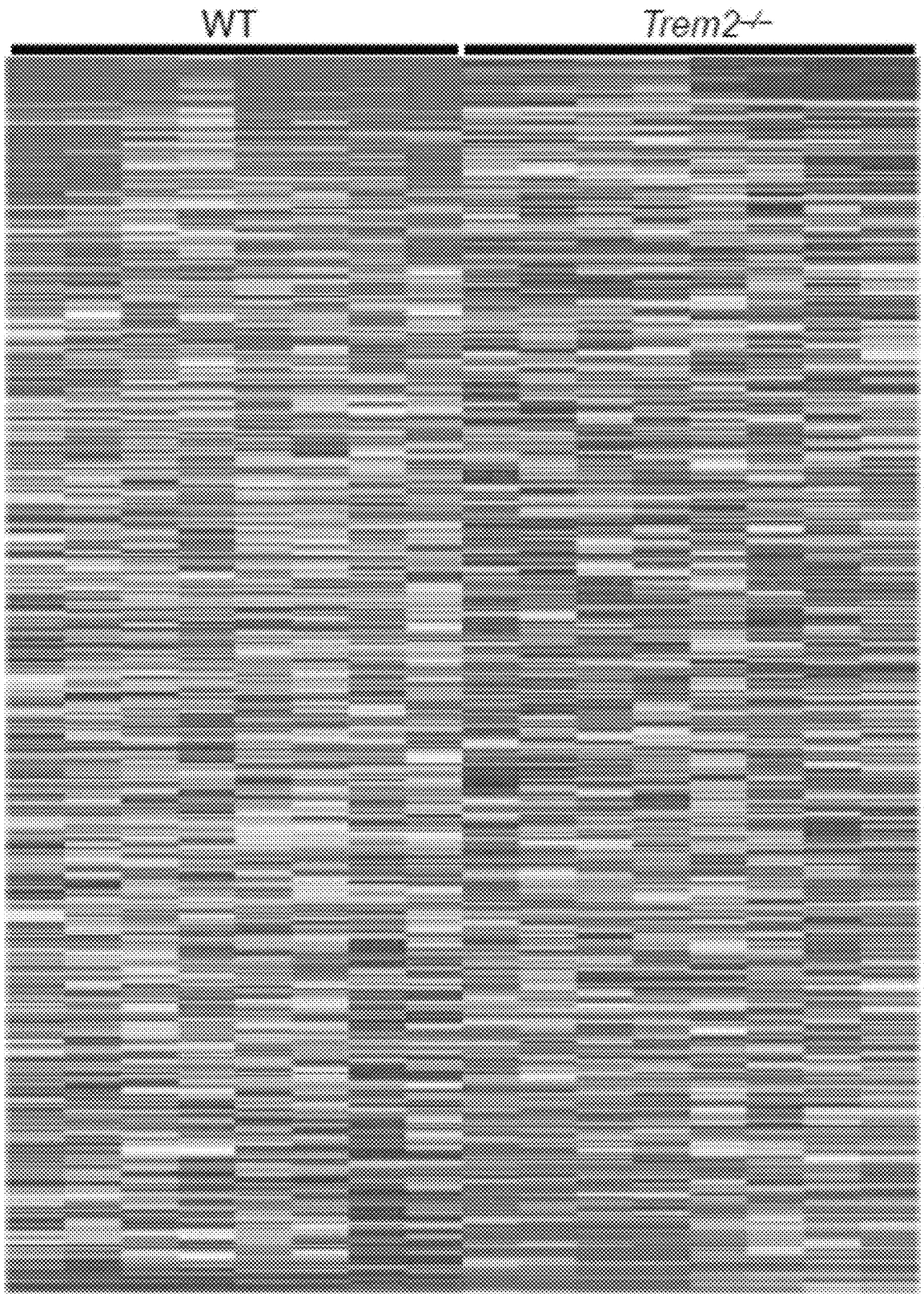
Figure 11B:
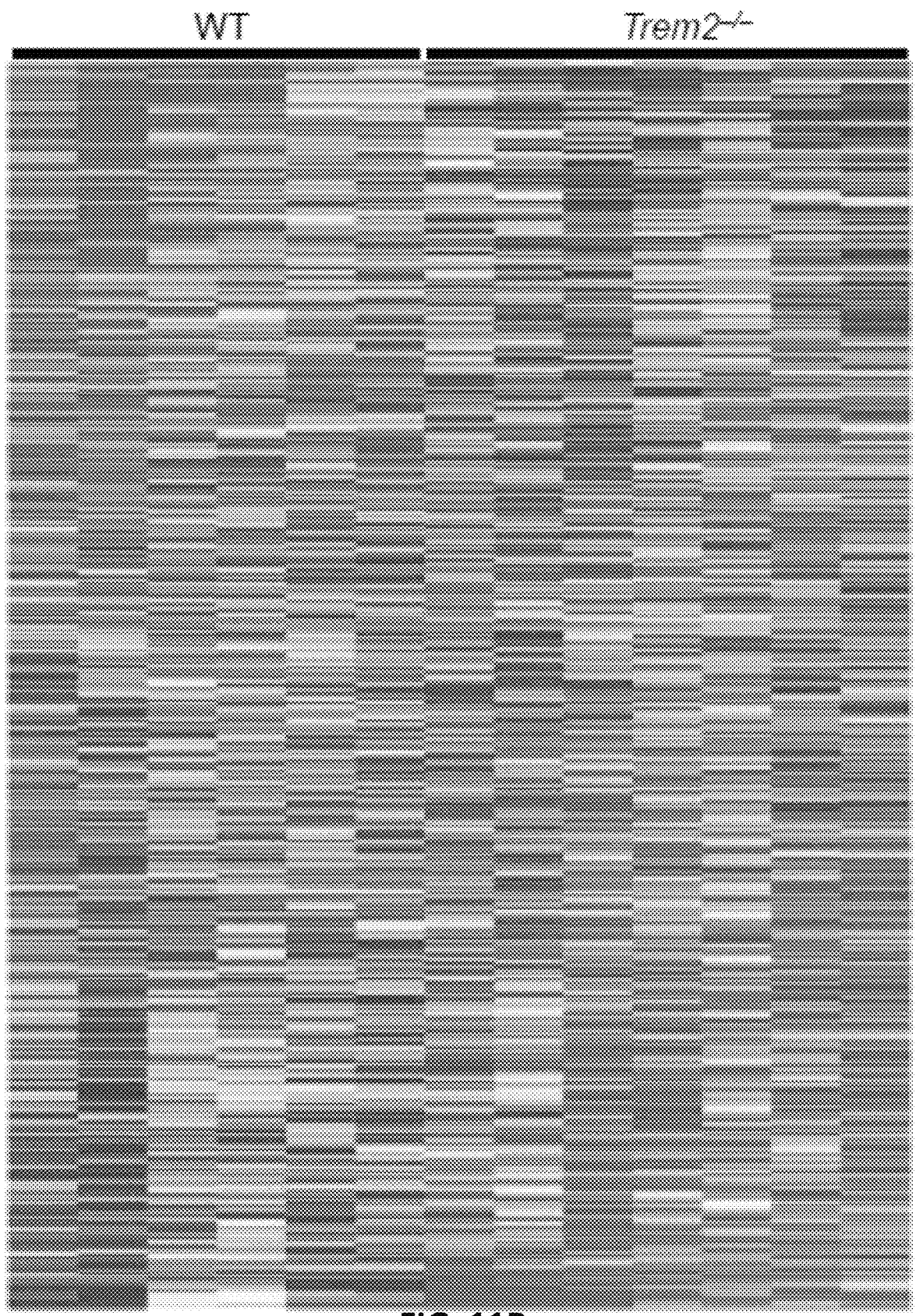
Figure 11C:
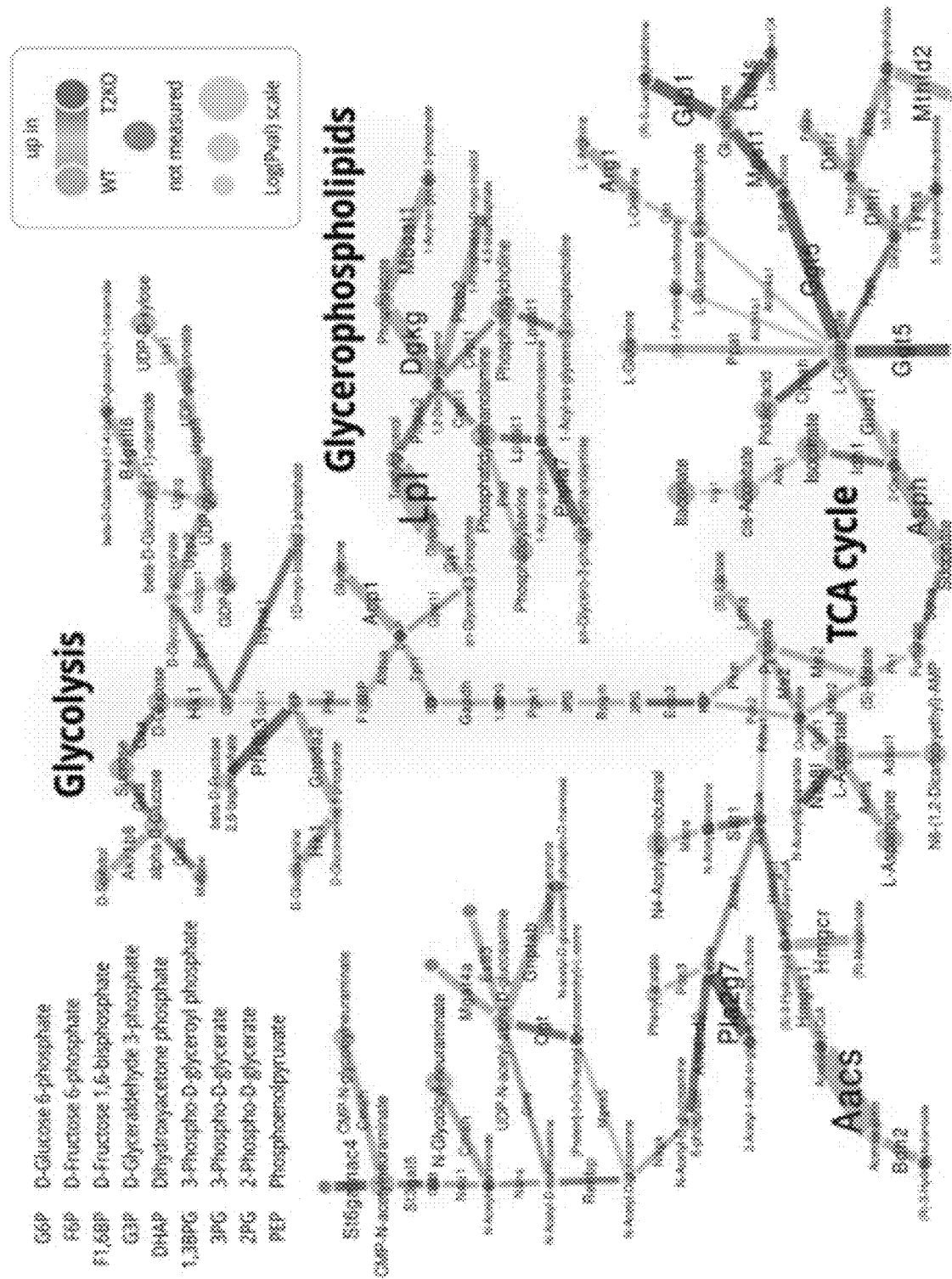
Figure 11D:
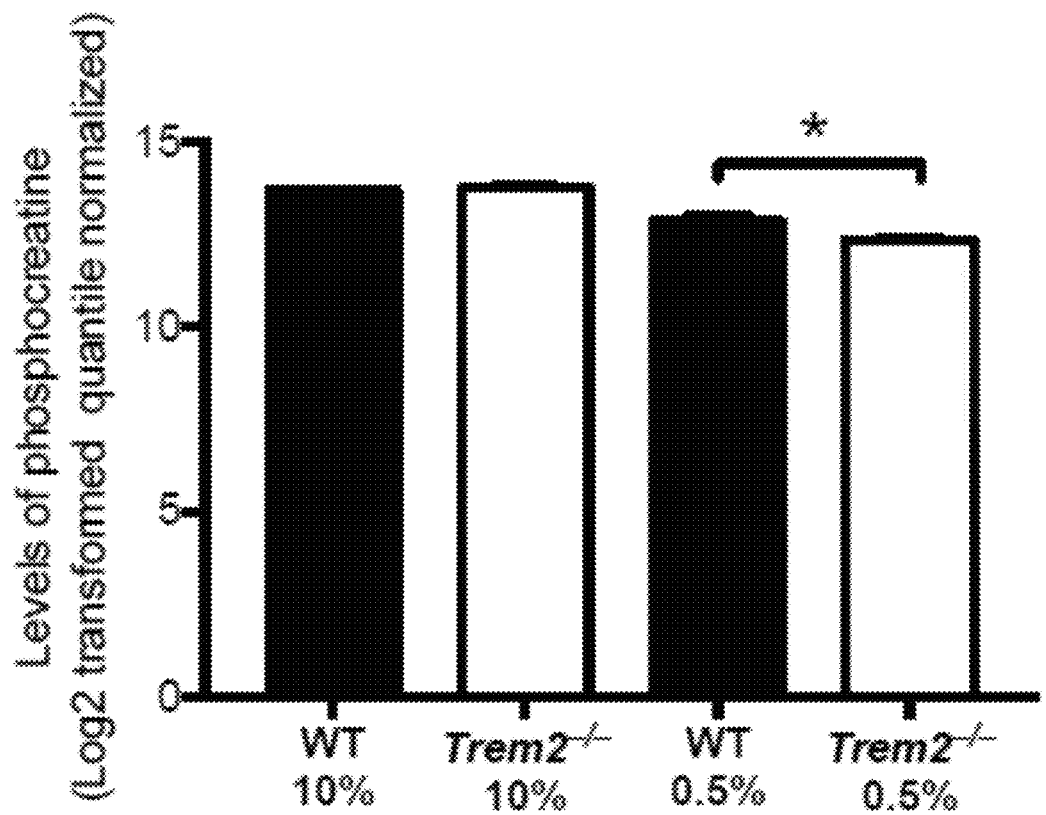
Figure 11E:
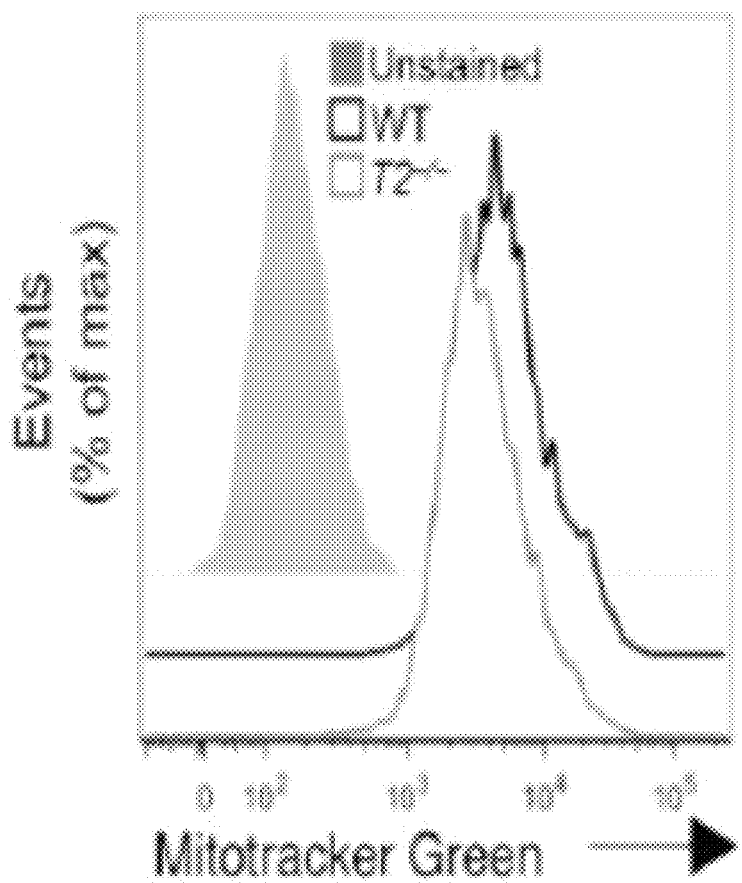
Figure 11F:
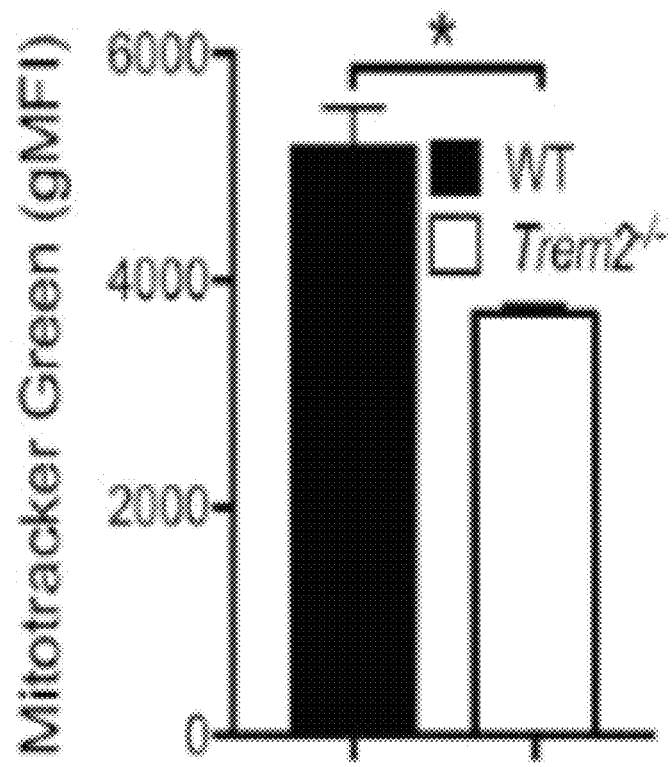
Figure 11G:
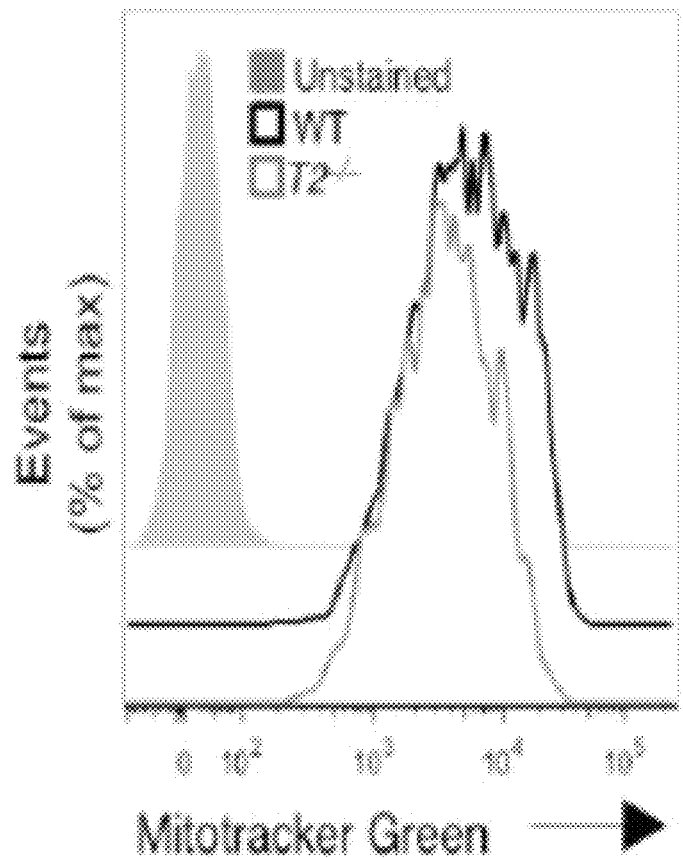
Figure 11H:
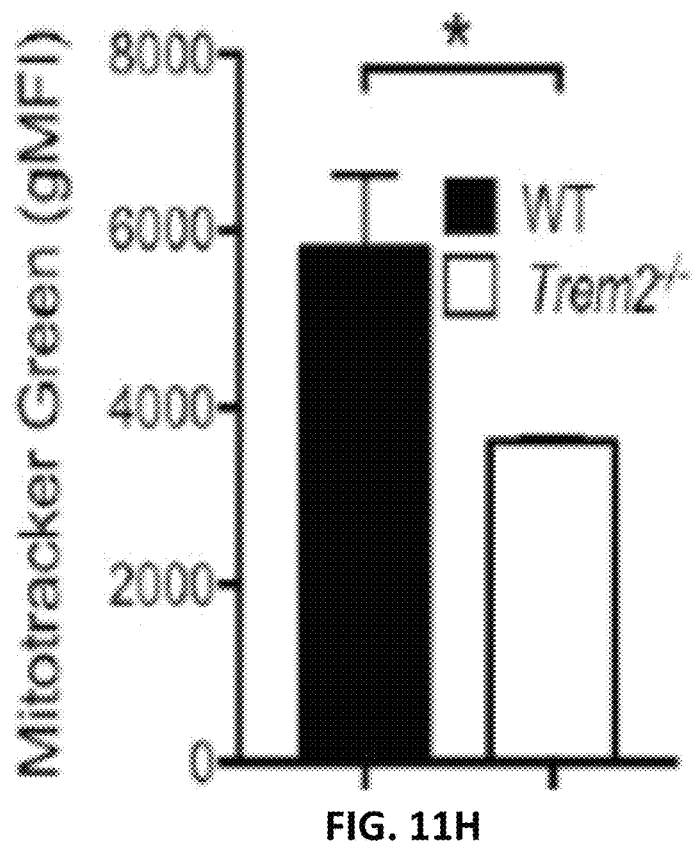
Figure 11I:
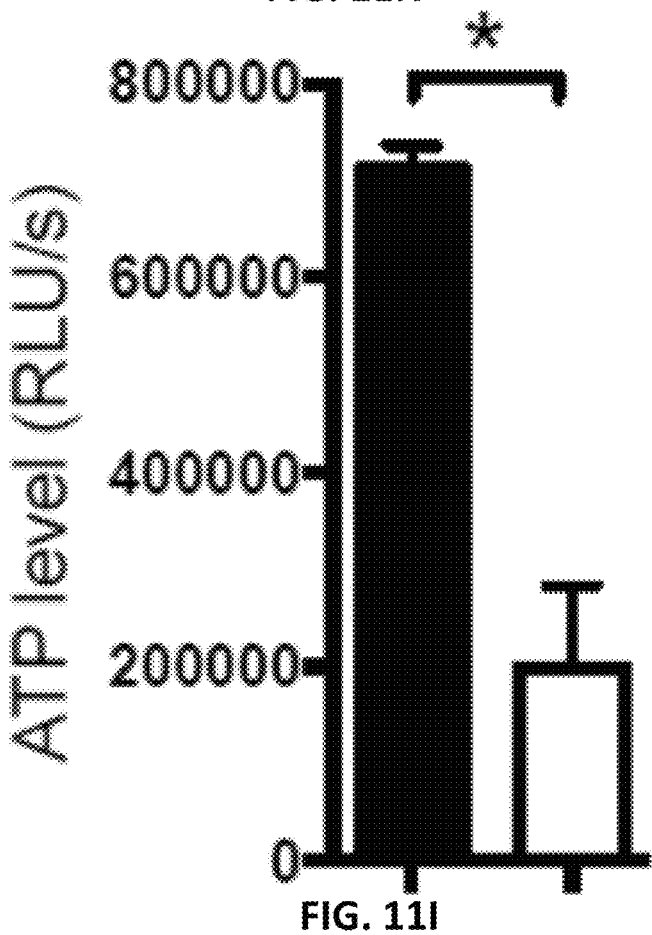
Figure 11J:
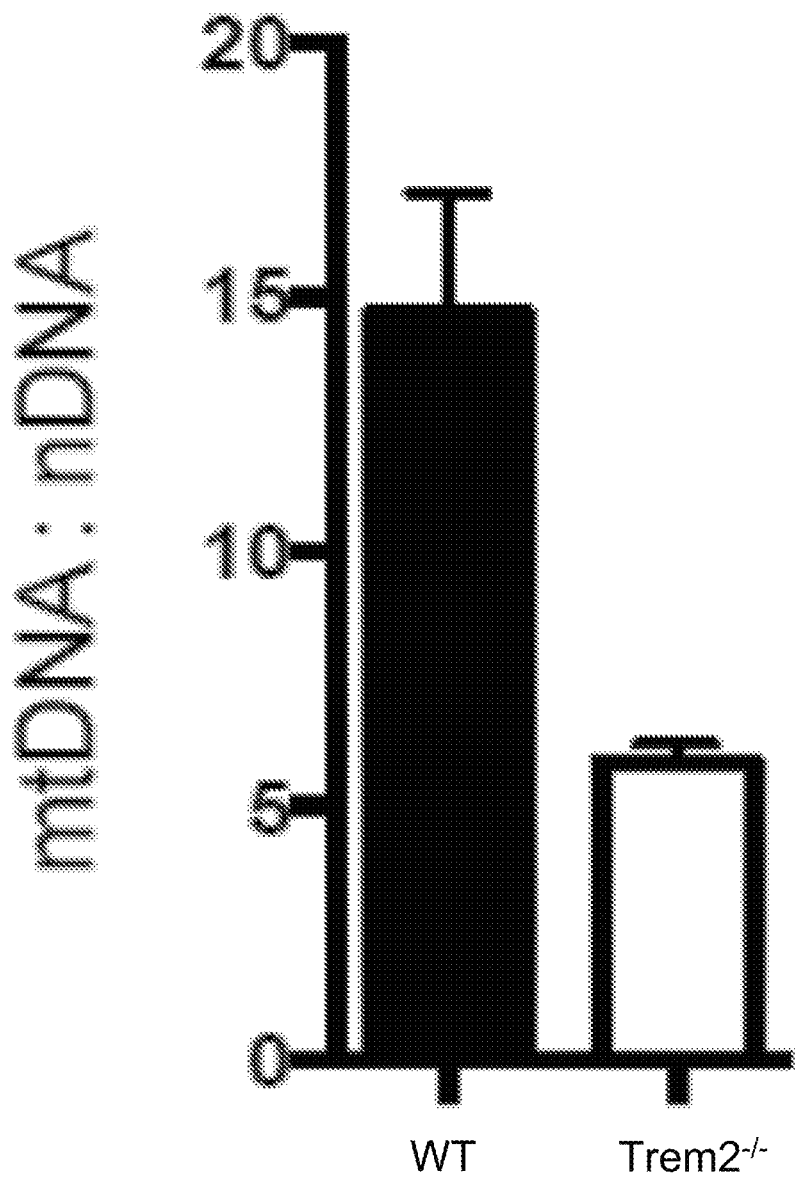
Figure 11K:
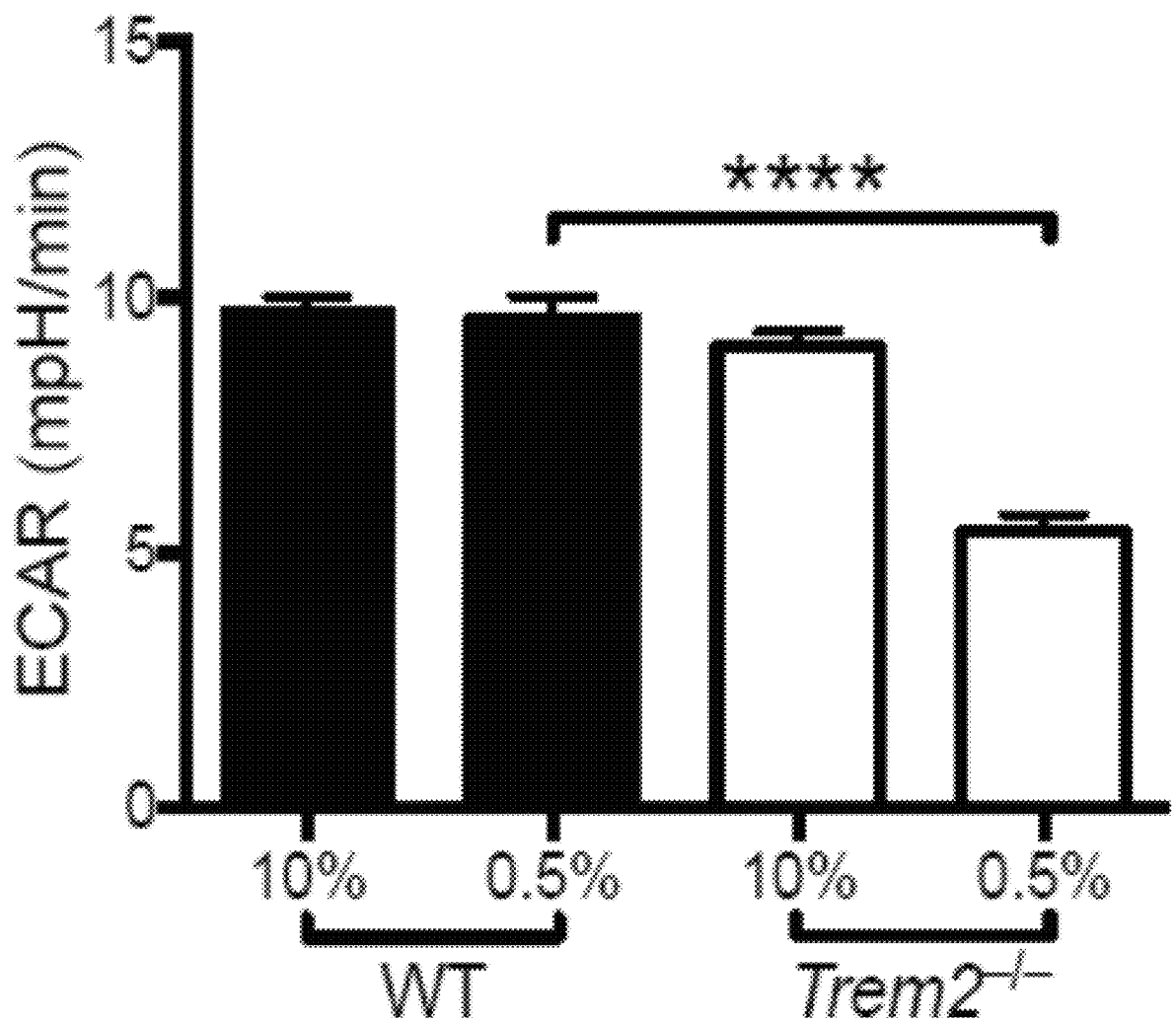
Figure 11L:
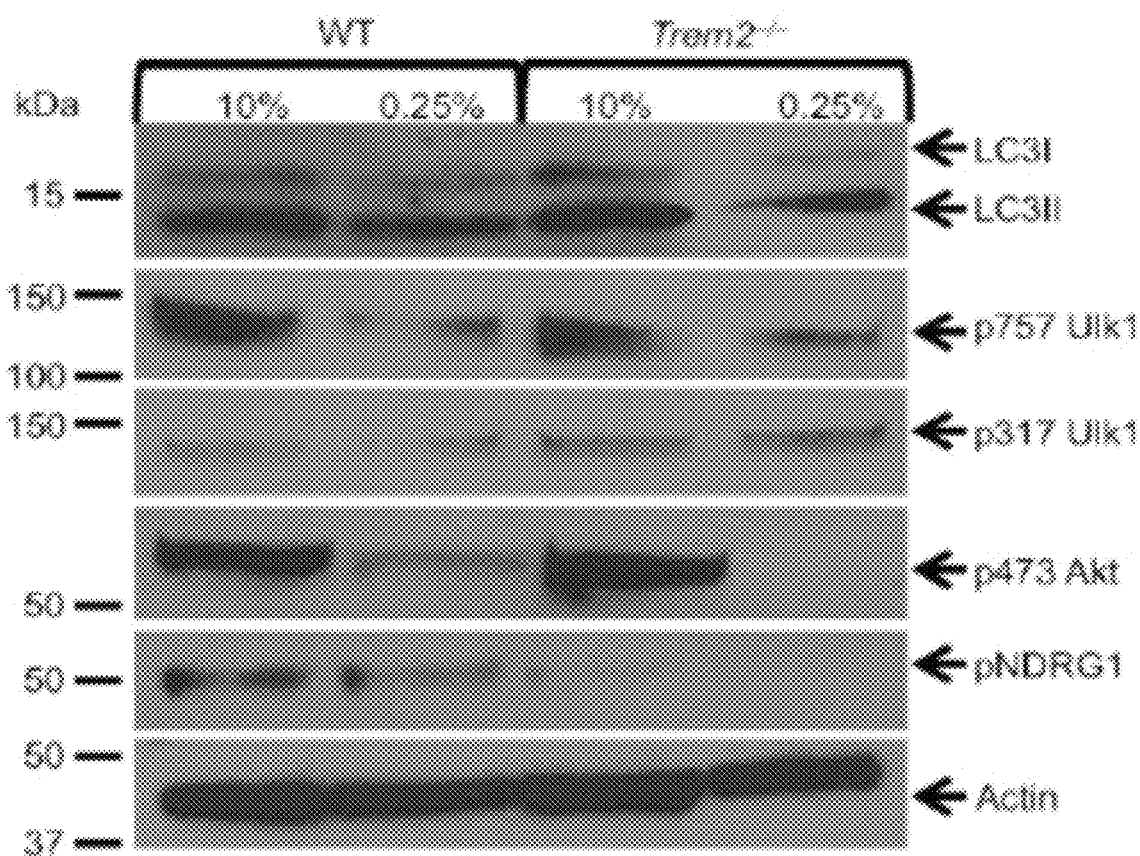
Figure 11M:
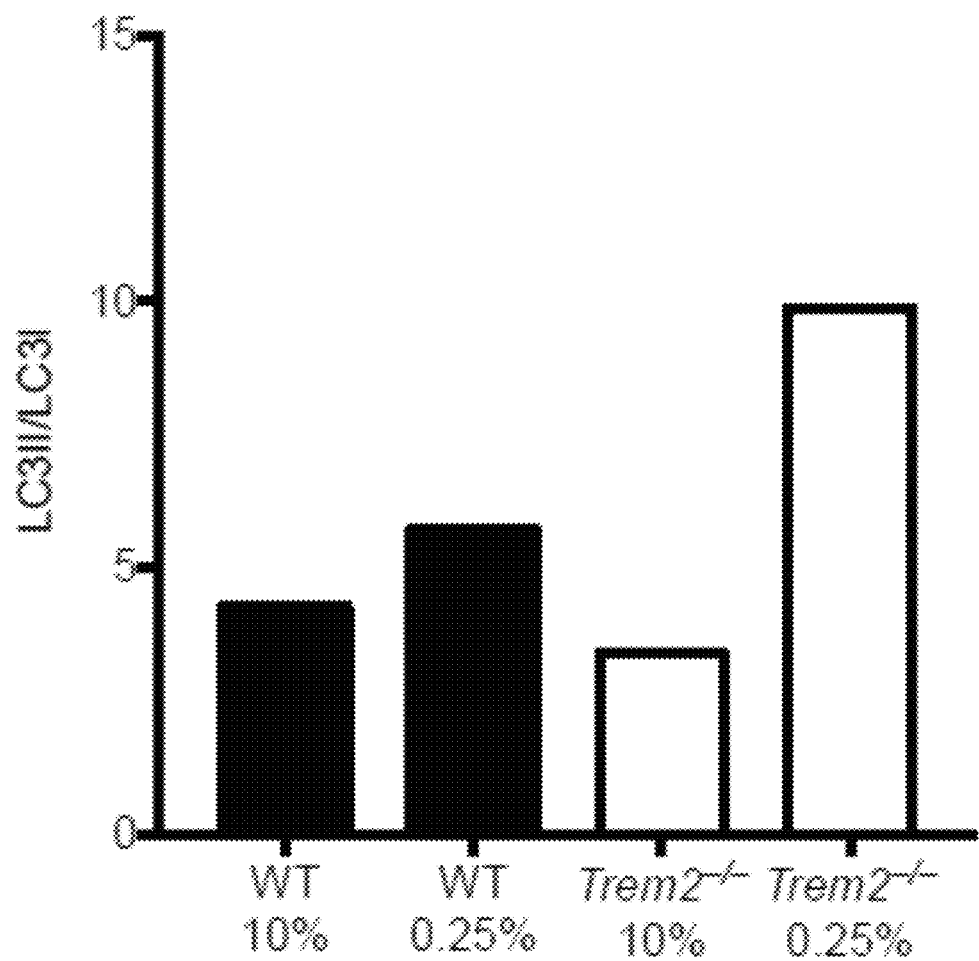

FIG. 11A, FIG. 11B, FIG. 11C, FIG. 11D, FIG. 11E, FIG. 11F, FIG. 11G, FIG. 11H, FIG. 11I, FIG. 11J, FIG. 11K, FIG. 11L and FIG. 11M show macrophages and microglia from Trem2$^{-/-}$ mice are less energetically active. Related to FIG. 4. FIG. 11A, FIG. 11B heatmaps representing the total metabolic profiles of WT compared to Trem2$^{-/-}$ BMDMs culture overnight in 10% LCCM (A) or 0.5% LCCM (FIG. 11B). FIG. 11C Shiny-GAM output for network analysis combining RNA-seq and mass spectrometry data highlights differences between WT and Trem2$^{-/-}$ BMDM cultured overnight in 0.5% LCCM. Enzymes-encoding mRNAs and metabolites that are downregulated or upregulated in Trem2$^{-/-}$ cells vs. WT cells are represented by green or red nodes and connecters, respectively. FIG. 11D quantification of phosphocreatine from WT and Trem2$^{-/-}$ BMDMs cultured in the indicated concentration of LCCM. FIG. 11E, FIG. 11F assessment and quantification of the mitochondrial mass of resident peritoneal macrophages from WT and Trem2$^{-/-}$ mice by MitoTraker Green incorporation. FIG. 11G, FIG. 11H assessment and quantification of the mitochondrial mass of thioglycolate elicited peritoneal macrophages from WT and Trem2$^{-/-}$ mice by MitoTracker Green incorporation. FIG. 11I ATP content of WT and Trem2$^{-/-}$ microglia cultured in 10% LCCM overnight. FIG. 11J mitochondrial content of WT and Trem2$^{-/-}$ microglia assessed by the ratio of mitochondrial-to-nuclear DNA. FIG. 11K extracellular acidification rate (ECAR) of WT and Trem2$^{-/-}$ microglia cultured overnight in 10% LCCM. FIG. 11L primary WT and Trem2$^{-/-}$ microglia were incubated overnight in the indicated concentration of LCCM. Immunoblots for LC3, p757 Ulk1, p317 Ulk1, p473 Akt, pNDRG1, and β actin were performed. FIG. 11M quantification of the LC3II/LC3I ratio from immunoblot performed on primary microglia shown in FIG. 11L. *p<0.05 or ****p<0.001 by One-way ANOVA with Holm-Sidak's multiple comparisons test (FIG. 11 FIG. 11, FIG. 11F, FIG. 11I, FIG. 11H, FIG. 11K). Results are representative of at least 3 independent experiments (FIG. 11E-FIG. 11K) or 2 independent experiments (FIG. 11L, FIG. 11M).

Figure 12A:
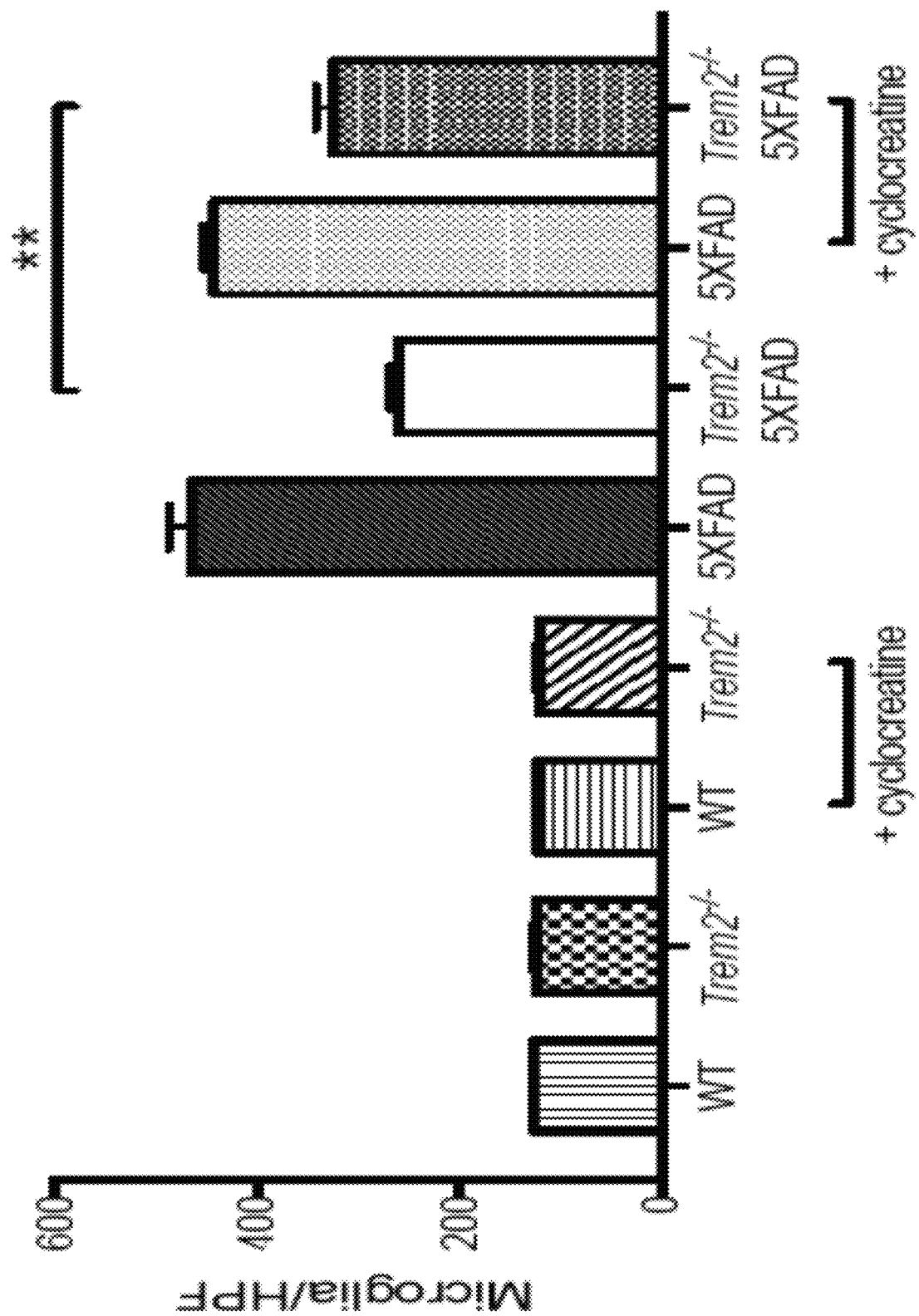
Figure 12B:
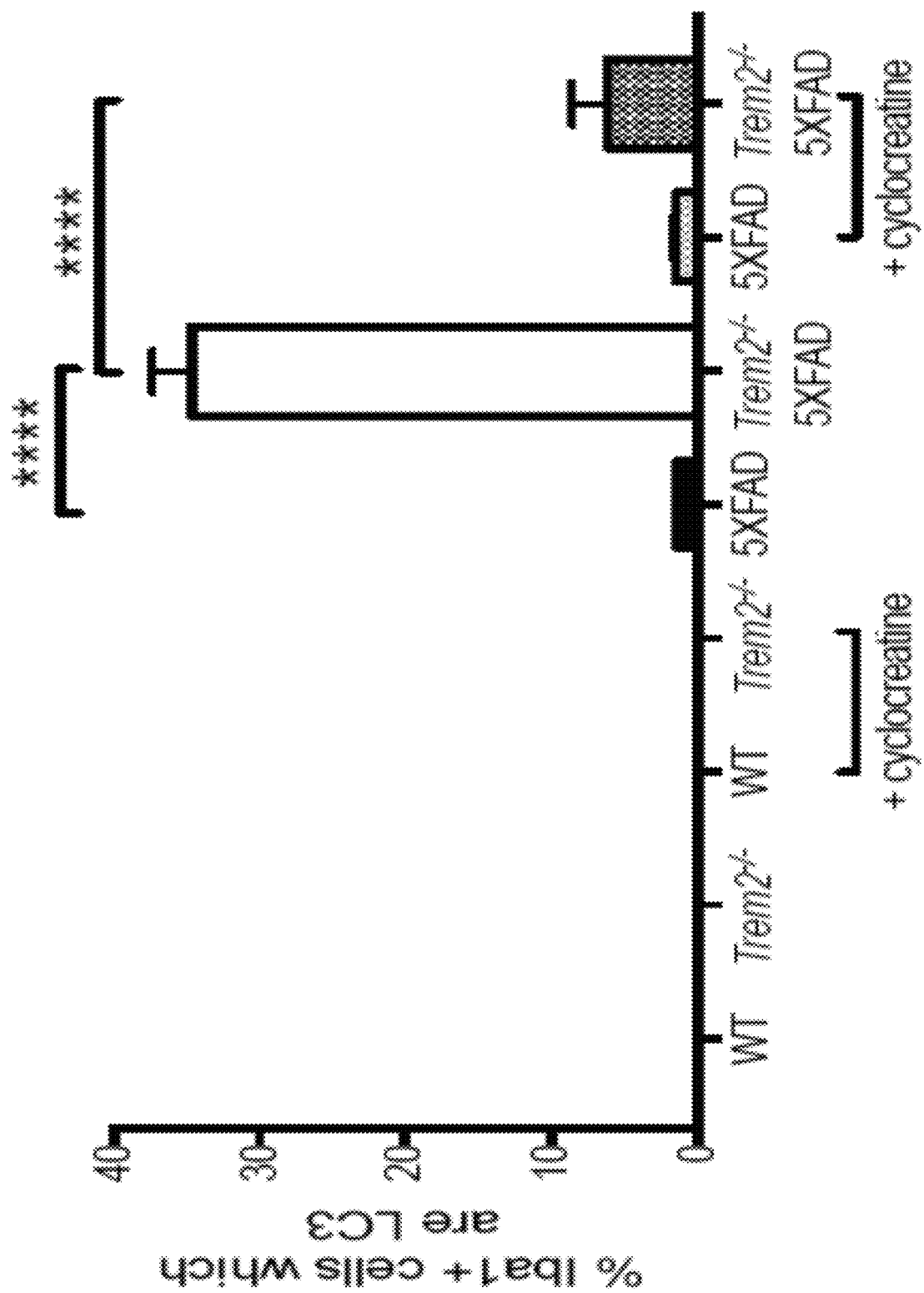
Figure 12C:
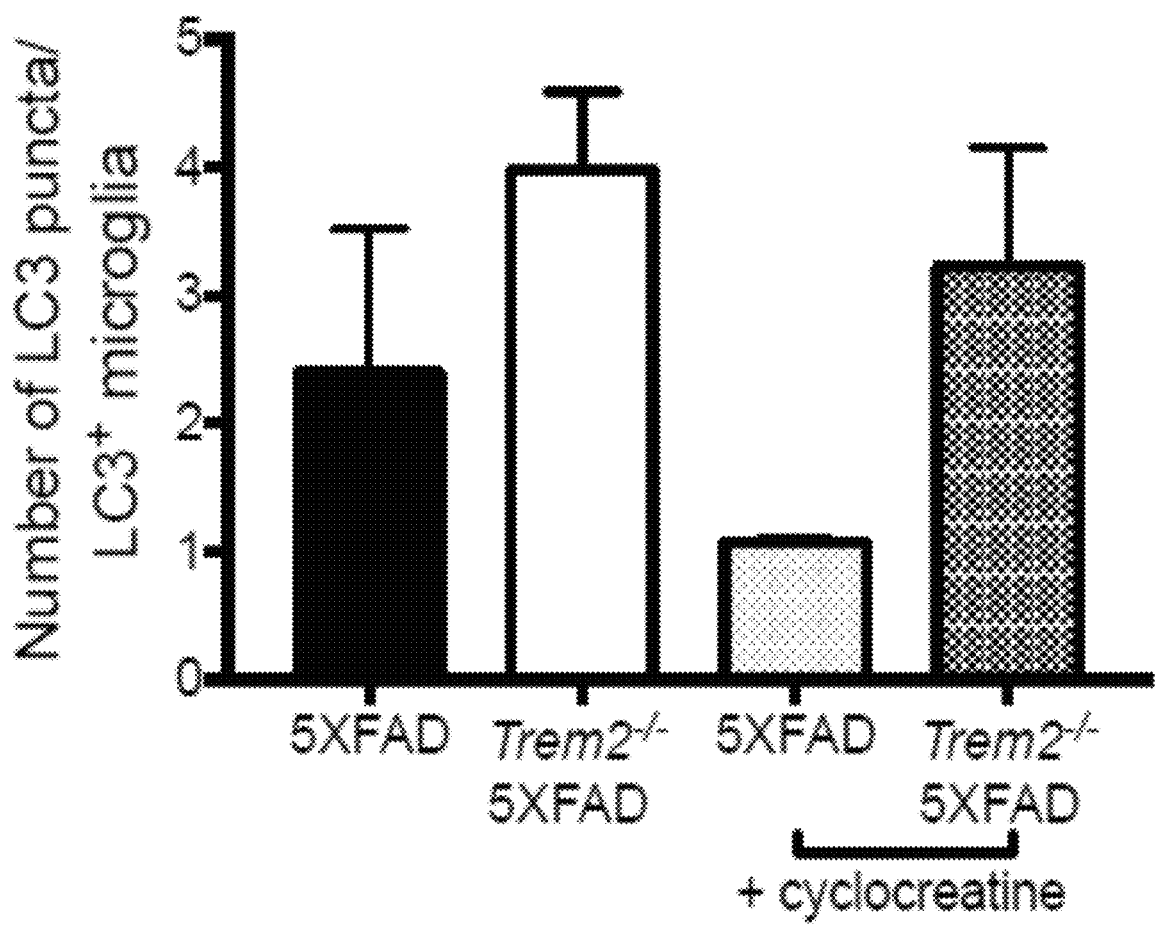
Figure 12D:
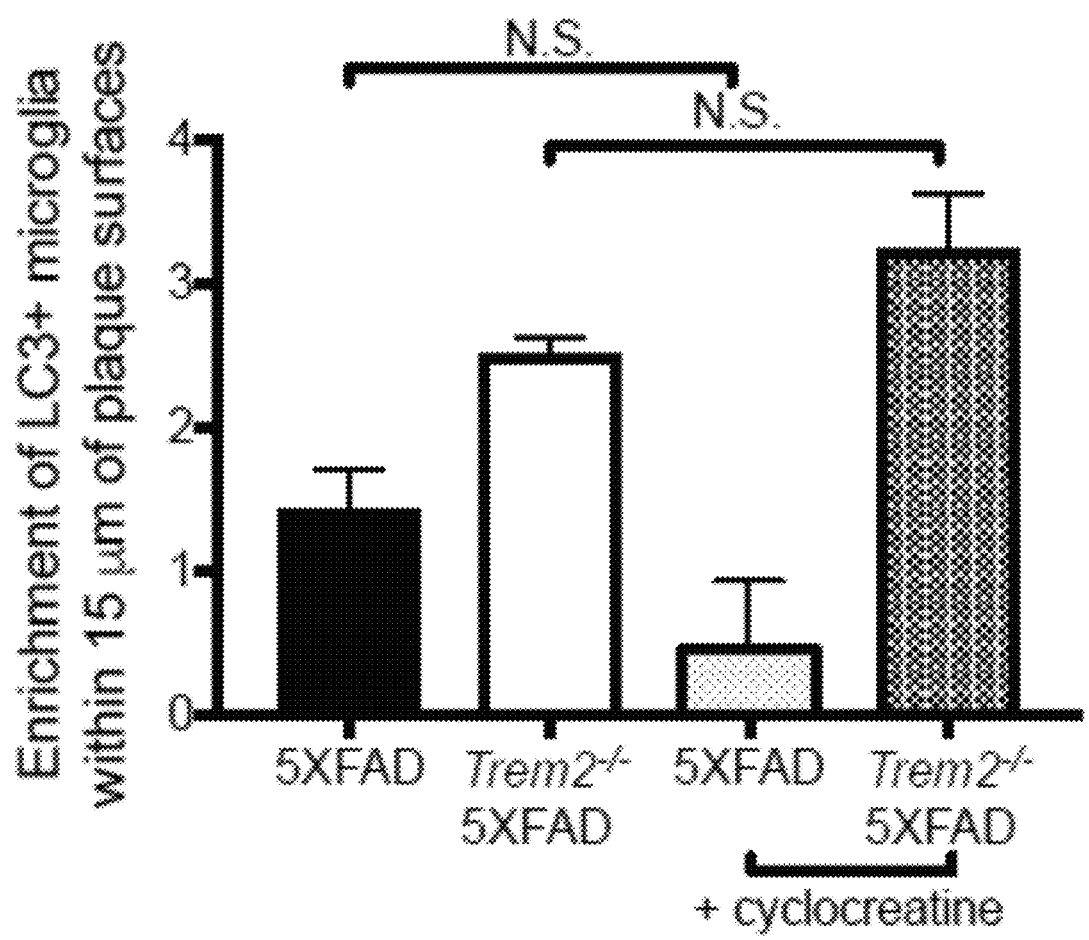
Figure 12E:
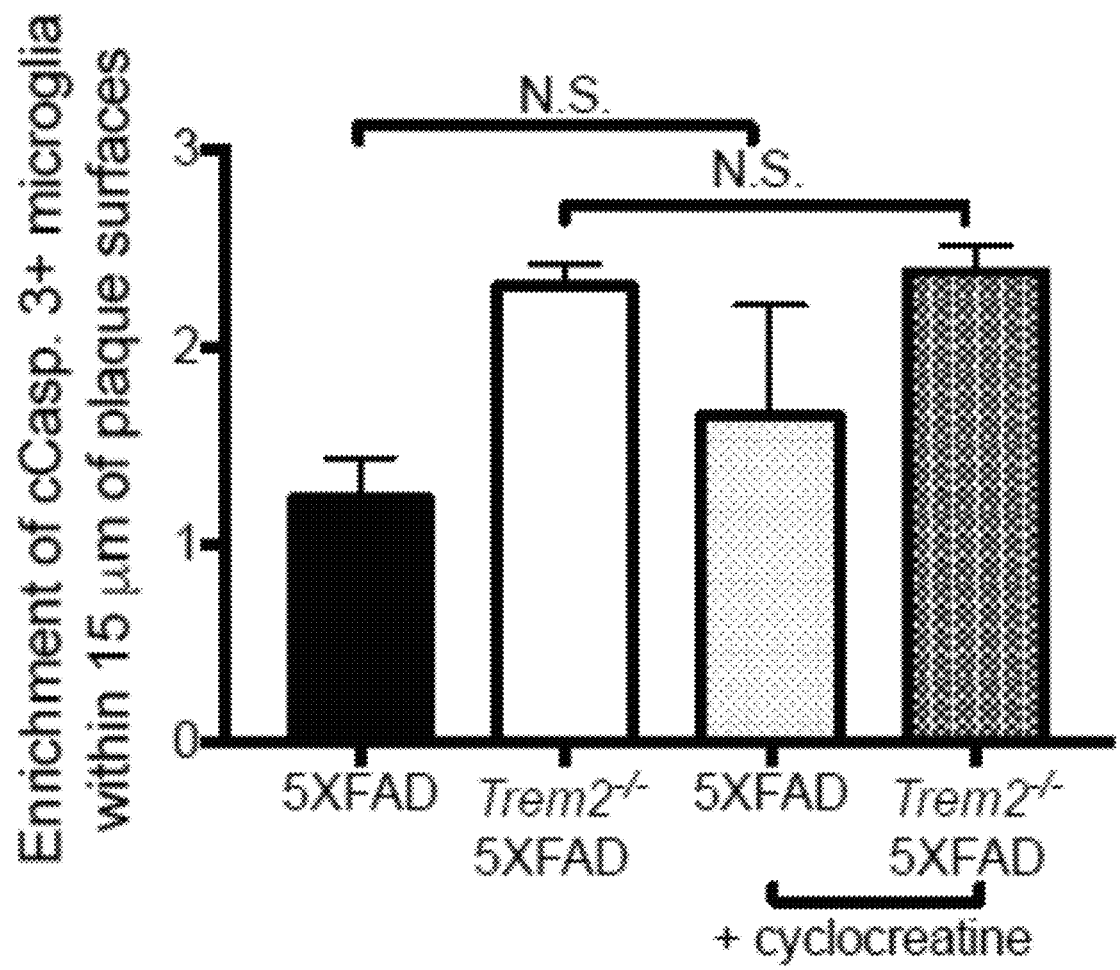
Figure 12F:
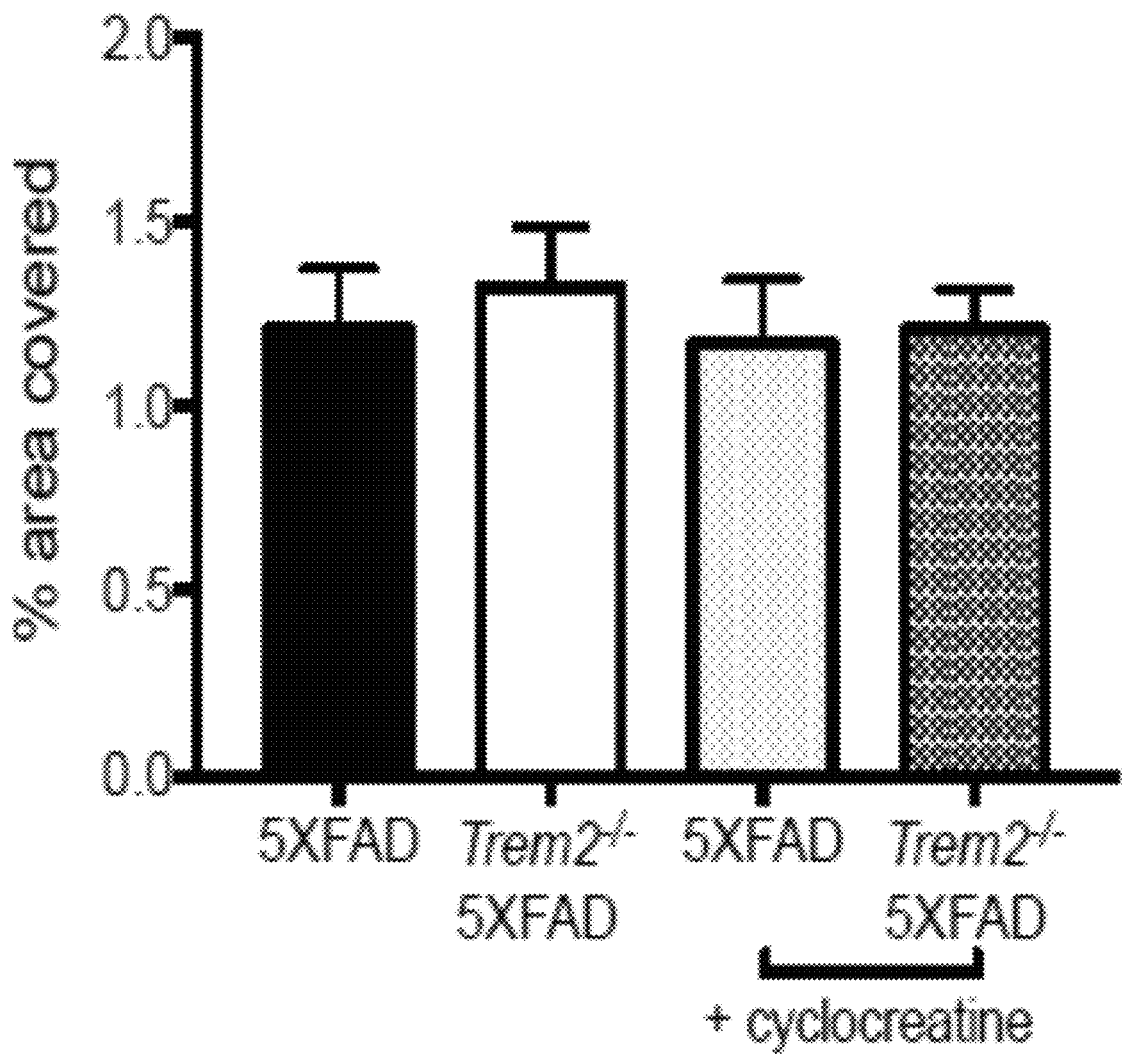
Figure 12G:
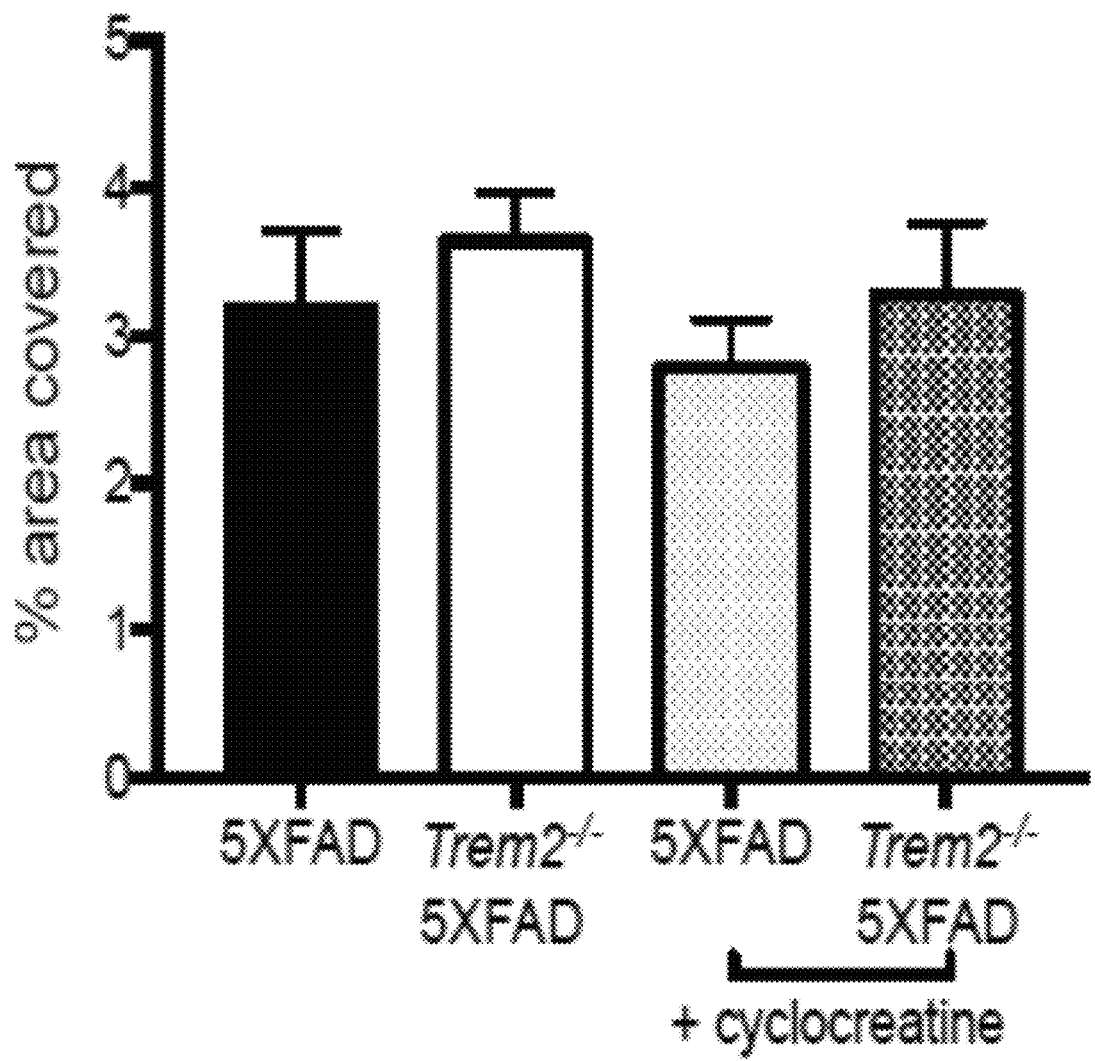
Figure 12H:
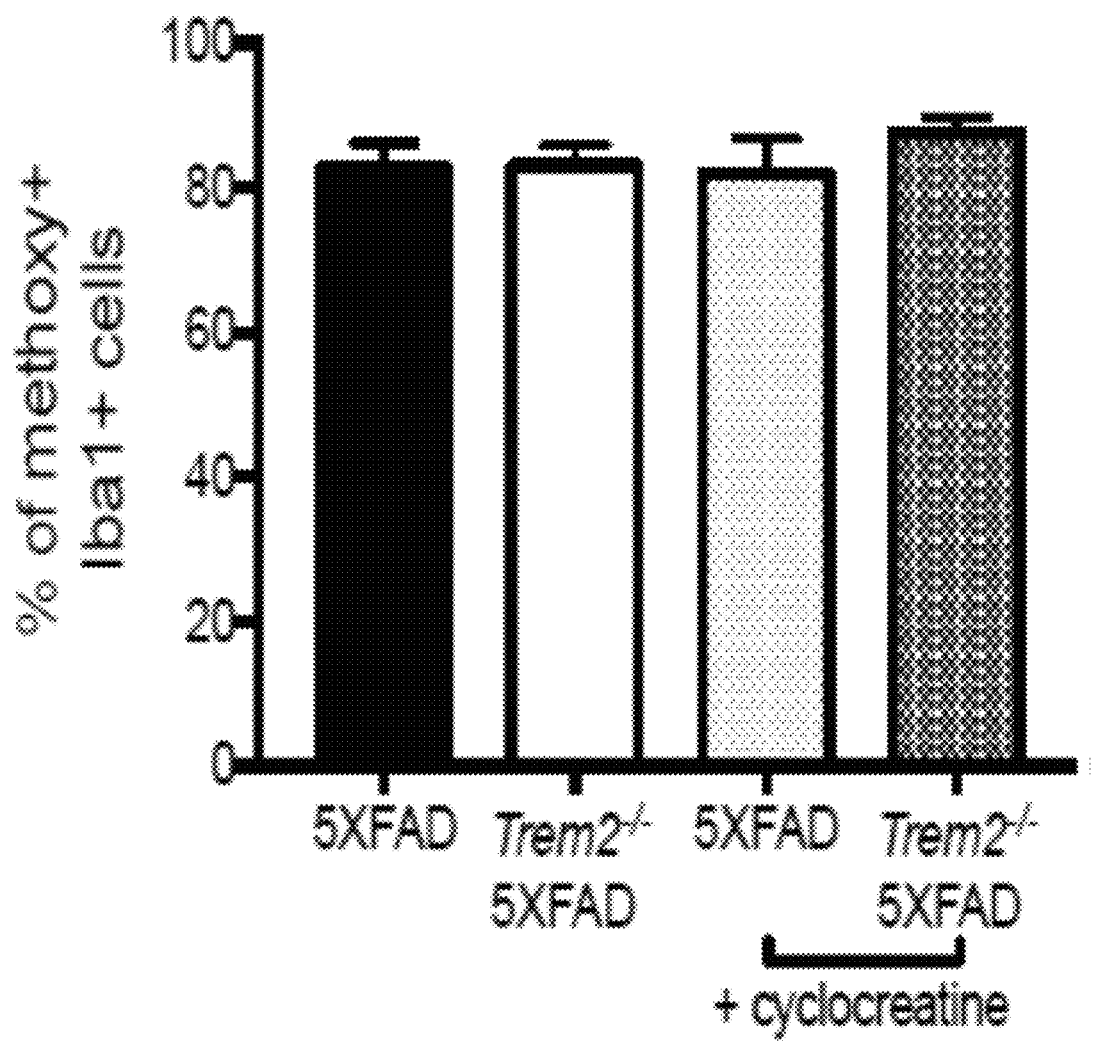
Figure 12I:
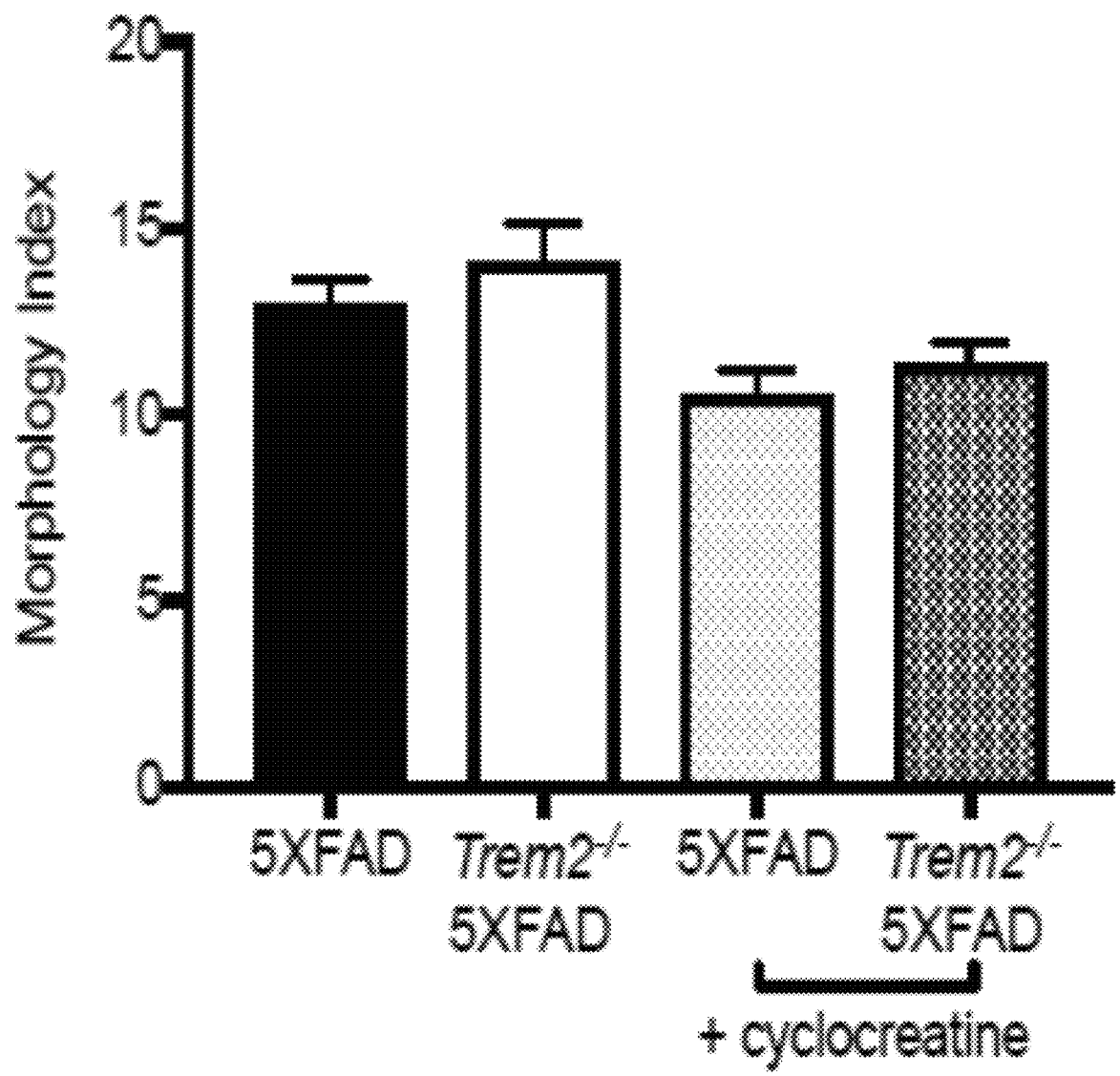

FIG. 12A, FIG. 12B, FIG. 12C, FIG. 12D, FIG. 12E, FIG. 12F, FIG. 12G, FIG. 12H, and FIG. 12I depict enhanced energy storage improves microglial response in Trem2$^{-/-}$ 5XFAD mice in vivo. Related to FIG. 6 and FIG. 7. FIG. 12A quantification of the number of microglia per high-powered field in the cortexes of brains from mice of the indicated genotype and treatment group. FIG. 12B quantification of the percentage of microglia that contain LC3 puncta in the cortexes of brains from mice of the indicated genotype and treatment group. FIG. 12C quantification of the number of LC3 puncta per LC3$^+$ microglia. FIG. 12D quantification of the relative enrichment of LC3$^+$ microglia within 15 µm of a plaque surface in the cortexes of brains from mice of the indicated genotype and treatment group. FIG. 12E quantification of the relative enrichment of cleaved caspase-3⁺ microglia within 15 µm of a plaque surface in the cortexes of brains from mice of the indicated genotype and treatment group. FIG. 12F and FIG. 12G the percent of the overall area of the cortex (FIG. 12F) and hippocampus (FIG. 12G) 1.5× brighter than the mean in methoxy-X04 stained sections from mice of the indicated genotype and treatment group. FIG. 12H quantification of the percentage of microglia containing methoxy-X04 in plaque bearing regions of the cortexes from mice of the indicated genotype and treatment group. FIG. 12I assessment of the complexity of plaques in the cortexes from mice of the indicated genotype and treatment group. N.S. indicates not significant, $p<0.01$ or **$p<0.001$ by One-way ANOVA with Holm-Sidak's multiple comparisons test (FIG. 12A, FIG. 12B, FIG. 12D, FIG. 12E). Results pooled from 2 independent experiments representing a total of 5-8 male and female mice per treatment group.

DETAILED DESCRIPTION

Applicants have discovered that the use of a microglial rescuing agent which supplements microglial energetic metabolism can be an effective treatment for subjects with microglial dysfunction-associated diseases, disorder, and conditions.

Disclosed herein are components used to prepare disclosed compositions as well as the compositions themselves, and methods of use thereof. It is understood that when combinations, subsets, interactions, groups, etc. of these materials are disclosed, that while specific reference to each various individual and collective combinations and permutation may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated, meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Additional aspects of the invention are described below.
(I) Compositions

One aspect of the present disclosure encompasses a microglial rescuing agent capable of mitigating one or more of the pathologies associated with microglial dysfunction. In some embodiments microglial dysfunction results from perturbations of cellular biosynthetic metabolism. In one aspect, microglial dysfunction results from impaired mTOR activation. In some embodiments, the present disclosure encompasses providing a therapeutically effective amount of one or more microglial rescuing agents, which results in improved metabolic activity, decreased autophagy, decreased cell death, improved microglia viability, improved microglia numbers or a combination thereof.

A composition of the invention may optionally comprise one or more additional drugs or therapeutically active agents in addition to the microglial rescuing agent. A composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

The compositions as disclosed herein comprise microglial rescuing agents such as creatine compounds, a creatine analogs, and pharmaceutically acceptable salts thereof. Additionally, the compositions as disclosed herein comprise activators of the dectin-1 pathway, such as dectin-1 ligands. The present disclosure also provides pharmaceutical compositions. The pharmaceutical composition comprises a microglial rescuing agent, as an active ingredient, and at least one pharmaceutically acceptable excipient.

Other aspects of the invention are described in further detail below.
(a) Creatine Compounds Creatine compounds useful in the present invention include compounds which modulate microglial metabolism. As described herein, creatine and derivatives/analogs thereof have been identified to rescue microglial function and treat microglial-dysfunction associated disease. Creatine and analogs thereof have been shown to supplement microglial energetic metabolism in subjects with microglial dysfunction, particularly those with a TREM2 or ApoE variant. Compounds which are effective for this purpose include creatine, creatine phosphate and analogs thereof, compounds which mimic their activity, and salts of these compounds as defined herein. Exemplary creatine compounds are described below.

Creatine (also known as N-(aminoiminomethyl)-N-methylglycine; methylglycosamine or N-methyl-guanido acetic acid) is a known substance. (See, The Merck Index, 60 Eleventh Edition, No. 2570 (1989).

Creatine is phosphorylated chemically or enzymatically by creatine kinase to generate creatine phosphate, which also is known (see, The Merck Index, No. 7315). Both creatine and creatine phosphate (phosphocreatine) can be extracted from animal tissue or synthesized chemically. Both are commercially available.

Cyclocreatine is an essentially planar cyclic analog of creatine. Although cyclocreatine is structurally similar to creatine, the two compounds are distinguishable both kinetically and thermodynamically. Cyclocreatine is phosphorylated efficiently by creatine kinase in the forward reaction both in vitro and in vivo. Rowley, G. L., J. Am. Chem. Soc. 93: 5542-5551 (1971); McLaughlin, A. C. et. al., J. Biol. Chem. 247, 4382-4388 (1972).

The phosphorylated compound phosphocyclocreatine is structurally similar to phosphocreatine; however, the phosphorous-nitrogen (P N) bond of cyclocreatine phosphate is more stable than that of phosphocreatine. LoPresti, P. and M. Cohn, Biochem. Biophys. Acta 998: 317-320 (1989); Annesley, T. M. and J. B. Walker, J. Biol. Chem. 253; 8120-8125, (1978); Annesley, T. M. and J. B. Walker, Biochem. Biophys. Res. Commun. 74: 185-190 (1977).

A creatine analog can be any creatine analog that targets the creatine kinase system or a creatine based composition. For example, a creatine analog can be cyclocreatine, phosphocreatine (aka creatine phosphate), nicotinamide mononucleotide (NMN), creatine ethyl ester, creatine nitrate, creatine gluconate, creation methyl ester, creatine riboside, creatine sulphate, serotonin creatine sulphate, creatine ethylester (HCl), creatine hydrochloride, creatine pyruvate, creatine citrate, creatine hemisulfate salt, creatine-(methyl-d3) monohydrate, creatine zinc chloride, creatine taurinate, 5,7-dihydroxytryptamine, L-arginine alpha-ketoglutarate, creatine pyroglutamate, creatine calcium, creatine magnesium, creation dextrose, creatine ethyl ester malate, or derivatives thereof. Exemplary compounds are shown below:

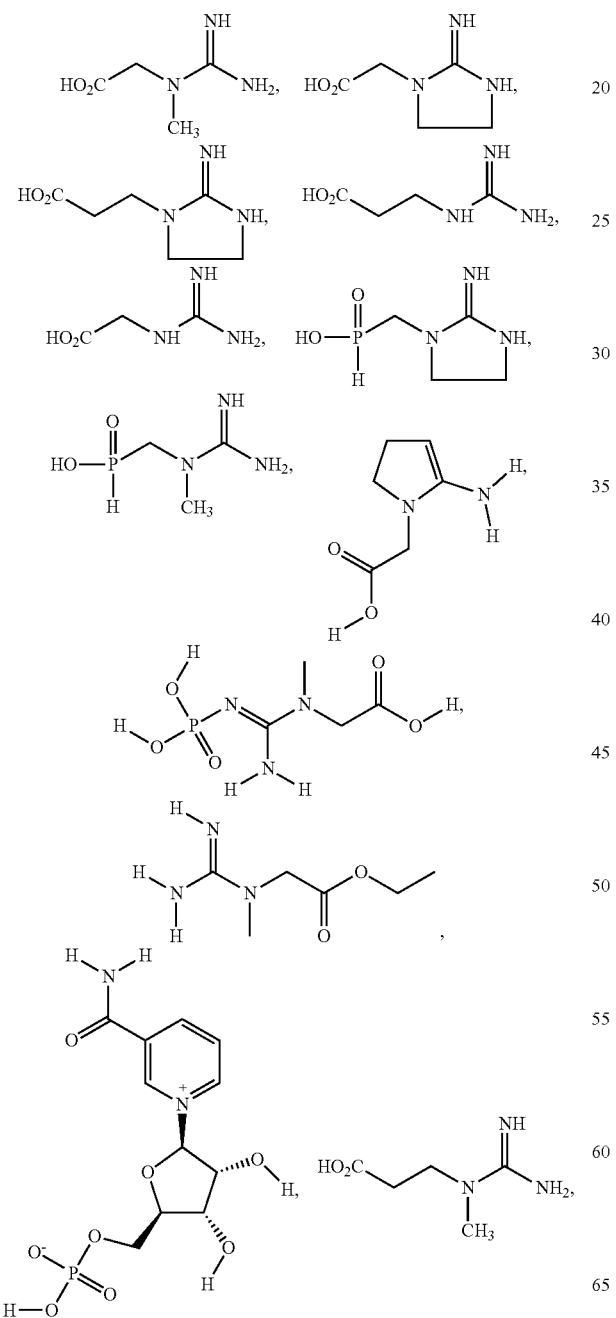

-continued

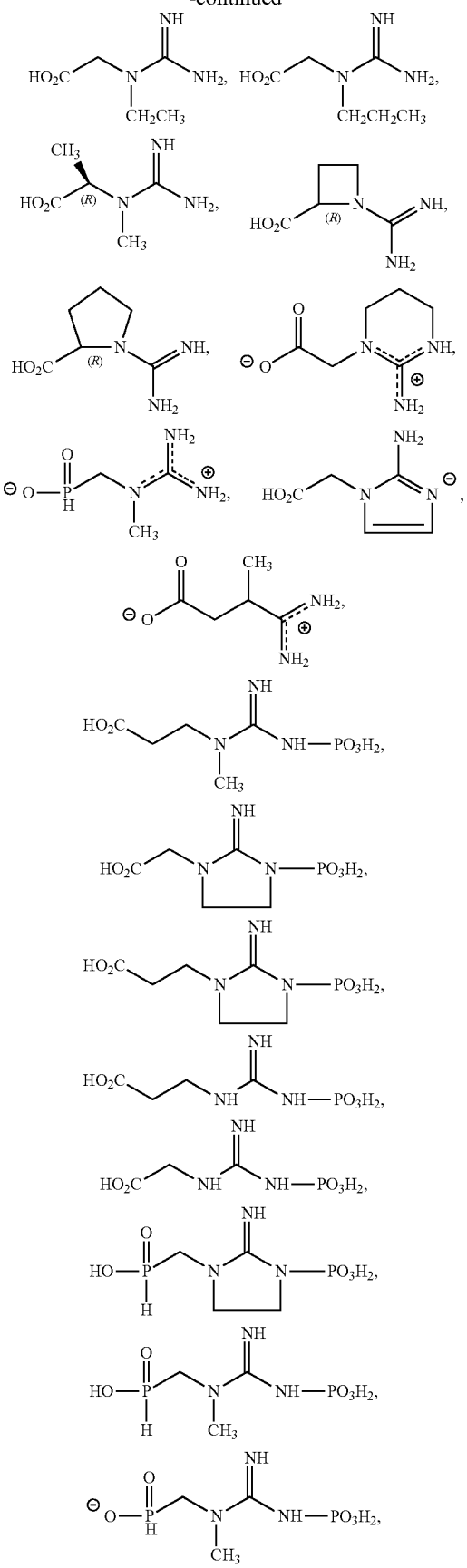

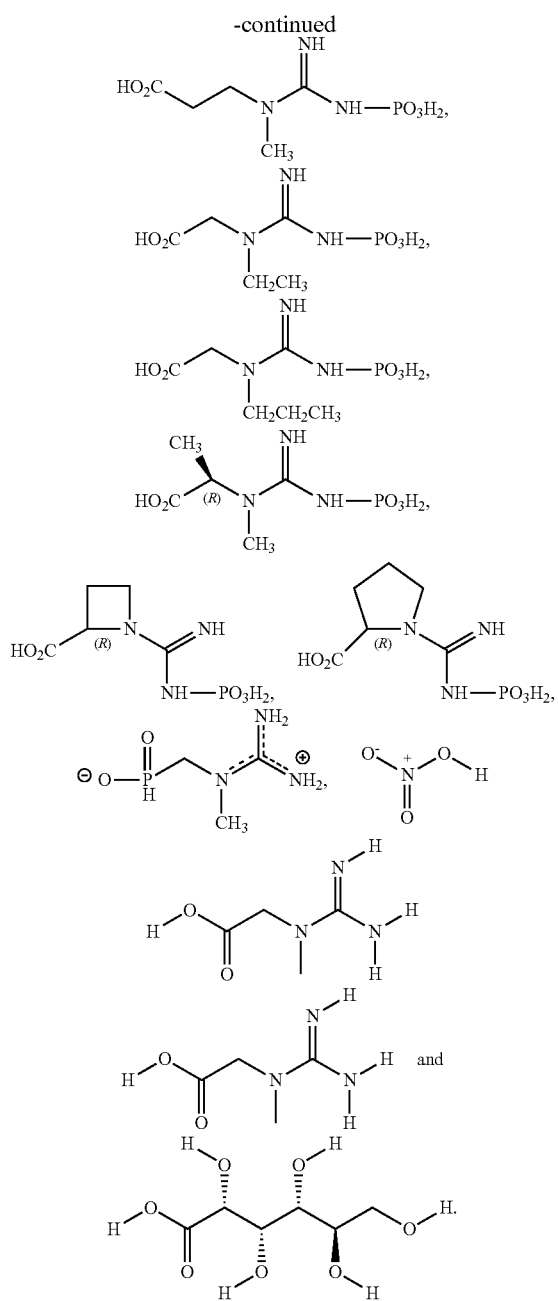

(b) Dectin-1 Agonist

Dectin-1 (aka C-type lectin domain family 7 member A; UniProt accession number Q9BXN2) is a protein that in humans is encoded by the CLEC7A gene. Dectin-1 is a member of the C-type lectin/C-type lectin-like domain (CTL/CTLD) superfamily. The encoded glycoprotein is a small type II membrane receptor with an extracellular C-type lectin-like domain fold and a cytoplasmic domain with a partial immunoreceptor tyrosine-based activation motif. It functions as a pattern-recognition receptor for a variety of β-1,3-linked and β-1,6-linked glucans from fungi and plants, and in this way plays a role in innate immune response. Expression is found on myeloid dendritic cells, monocytes, macrophages and B cells. Alternate transcriptional splice variants, encoding different isoforms, have been characterized. This gene is closely linked to other CTL/CTLD superfamily members on chromosome 12p13 in the natural killer gene complex region. Dectin-1 is a transmembrane protein containing an immunoreceptor tyrosine-based activation (ITAM)-like motif in its intracellular tail (which is involved in cellular activation) and one C-type lectin-like domain (carbohydrate-recognition domain, CRD) in the extracellular region (which recognizes β-glucans and endogenous ligands on T cells). The CRD is separated from the membrane by a stalk region. CLEC7A contains putative N-linked sites of glycosylation in the stalk region.

The C-type lectin receptors are class of signaling pattern recognition receptors which are involved in antifungal immunity, but also play important roles in immune responses to other pathogens such as bacteria, viruses and nematodes. As a member of this receptor family, Dectin-1 recognizes β-glucans and carbohydrates found in fungal cell walls, some bacteria and plants, but may also recognize other unidentified molecules (endogenous ligand on T-cells and ligand on mycobacteria). Ligand binding induces intracellular signaling via the ITAM-like motif. CLEC7A can induce both Syk dependent or Syk independent pathways. Dimerization of dectin-1 upon ligand binding leads to tyrosine phosphorylation by Src family kinases and recruitment of Syk. Syk activates transcription factor NFκB. This transcription factor is responsible for the production of numerous inflammatory cytokines and chemokines such as TNF, IL-23, IL-6, IL-2. Other responses include: respiratory burst, production of arachidonic acid metabolites, dendritic cell maturation, and phagocytosis of the ligand.

The term "Dectin-1 agonist", also referred to herein as "Dectin-1 ligand", refers to a molecule that specifically binds to Dectin-1 resulting in activation of the Dectin-1 pathway. Activators of Dectin-1 signaling may be used alone, with other agents with similar or different effects or with other modalities, including surgery and the like.

In one aspect, this disclosure provides a microglial rescuing agent capable of activating the Dectin-1 signaling pathway. A Dectin-1 agonist is also referred to herein as a ligand. In one embodiment, the Dectin-1 agonistic is an antibody or a fragment thereof. In another embodiment, the Dectin-1 agonistic is a small molecule. Non-limiting examples of Dectin-1 ligands include beta-glucan peptide (BGP), curdlan AL, heat-killed C. albicans, heat-killed S. cerevisiae, laminarin, lichenan, pustulan, schizophyllan, scleroglucan, WGP Dispersible, Zymosan, Zymosan Depleted. These agonists are commercially available (Invivogen). Another example of Dectin-1 activator is vimentin. Another example of Dectin-1 activator is an agonistic anti-Dectin-1 antibody, such as, for example, an antibody described in U.S. Pat. No. 9,045,542, the description of which antibody is incorporated herein by reference. In one embodiment, a microglial rescuing agent is one or more of Dectin-1 agonists or activators.

In one aspect, this disclosure provides methods for identifying activators of Dectin-1 pathway in microglial cells. In one embodiment, the activators of Dectin-1 pathway are Dectin-1 agonists. The activity of a test agent may be evaluated based on the effect on any step of the Dectin-1 pathway (as described in this disclosure). It can be compared to the effect in the absence of the test compound or may be compared to the effect of Dectin-1 or a known agonist thereof.

Assays to evaluate agents for binding to Dectin-1 may be carried out by in vitro using purified or recombinant Dectin-1. Assays can also be carried out in vitro using cells which express Dectin-1—such as liver leukocytes or hepatic stellate cells. Further, screening test may be carried out in vivo using animal models. The cells in culture may be primary cells or may be secondary cells or cell lines. Examples of suitable cells include liver leukocytes (such as dendritic cells, macrophages, $CD14^+$ monocytic cells and the like), and hepatic stellate cells. The cells may be enriched from sources such as whole blood. For example, whole blood may be obtained from an individual and desired types of leukocytes may be isolated using well known techniques or using commercially available kits (such as kits from Miltenyi Biotec). In one embodiment, the cells may be modified cells. For example, the cells may be engineered to express or overexpress Dectin-1. The cells in culture can be maintained by using routine cell culture reagents and procedures. In one embodiment, the assays may be carried out in animals including mice after administration of Thioacetamide (TAA) or Carbon tetrachloride.

The compounds for testing may be part of a library or may be newly synthesized. Further, the compounds may be purified, partially purified or may be present as cell extracts, crude mixtures and the like—i.e., unpurified. While it is ideal to test each compound separately, a combination of compounds may also be tested.

Dosages of a microglial rescuing agent can vary between wide limits, depending upon the disease or disorder to be treated, the age and condition of the subject to be treated. In an embodiment where a composition comprising a microglial rescuing agent is contacted with a sample, the concentration of a microglial rescuing agent may be from about 0.1 µM to about 40 µM. Alternatively, the concentration of a microglial rescuing agent may be from about 5 µM to about 25 µM. For example, the concentration of a microglial rescuing agent may be about 0.1, about 0.25, about 0.5, about 0.6, about 0.7, about 0.8, about 0.9, about 1, about 2.5, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 35, or about 40 µM. Additionally, the concentration of a microglial rescuing agent may be greater than 40 µM. For example, the concentration of a microglial rescuing agent may be about 40, about 45, about 50, about 55, about 60, about 65, about 70, about 75, about 80, about 85, about 90, about 95, or about 100 µM.

In an embodiment where the composition comprising a microglial rescuing agent is administered to a subject, the dose of a microglial rescuing agent may be from about 0.1 mg/kg to about 500 mg/kg. For example, the dose of a microglial rescuing agent may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of a microglial rescuing agent may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of a microglial rescuing agent may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the LD50 (the dose lethal to 50% of the population) and the ED50, (the dose therapeutically effective in 50% of the population). The dose ratio between toxic and therapeutic effects is the therapeutic index that can be expressed as the ratio LD50/ED50, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Shargel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

(c) Components of the Composition

The present disclosure also provides pharmaceutical compositions. The pharmaceutical composition comprises a microglial rescuing agent, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In each of the embodiments described herein, a composition of the invention may optionally comprise one or more additional drug or therapeutically active agent in addition to the microglial rescuing agent. In some embodiments, the additional drug or therapeutically active agent is used to treat central nervous system diseases, or disorders. Other active agents which can be administered together with a microglial rescuing agent include but are not limited to neurotransmitters, neurotransmitter agonists or antagonists, steroids, corticosteroids (such as prednisone or methyl prednisone) immunomodulating agents (such as beta-interferon), immunosuppressive agents (such as cyclophosphamide or azathioprine), nucleotide analogs, endogenous opioids, or other currently clinically used drugs. In some embodiments, the secondary agent is selected from a corticosteroid, a non-steroidal anti-inflammatory drug (NSAID), an intravenous immunoglobulin, a tyrosine kinase inhibitor, a fusion protein, a monoclonal antibody directed against one or more pro-inflammatory cytokines, a chemotherapeutic agent and a combination thereof. In some embodiments, the secondary agent may be a glucocorticoid, a corticosteroid, a non-steroidal anti-inflammatory drug (NSAID), a phenolic antioxidant, an anti-proliferative drug, a tyrosine kinase inhibitor, an anti IL-5 or an IL5 receptor monoclonal antibody, an anti IL-13 or an anti IL-13 receptor monoclonal antibody, an IL-4 or an IL-4 receptor monoclonal antibody, an anti IgE monoclonal antibody, a monoclonal antibody directed against one or more pro-inflammatory cytokines, a TNF-α inhibitor, a fusion protein, a chemotherapeutic agent or a combination thereof. In some embodiments, the secondary agent is an anti-inflammatory drug. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, curcumin, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen picnol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, lysofylline, meclofenamate sodium, meclofenamic acid, meclorisone dibutyrate, mefenamic acid, mesalamine, meseclazone, methylprednisolone suleptanate, mom iflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, mepolizumab, prodrugs thereof, and a combination thereof.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylam ides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palm itate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

(d) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a microglial rescuing agent is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a microglial rescuing agent in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the microglial rescuing agent may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palm itate), n-octadecanoate (stearate), n-eicosanoate (arachidate), n-docosanoate (behenate), n-tetracosanoate (lignocerate), cis-9-hexadecenoate (palm itoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a microglial rescuing agent may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of the microglial rescuing agent, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The microglial rescuing agent may be encapsulated in a microemulsion by any method generally known in the art.

In yet another embodiment, a microglial rescuing agent may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(II) Methods

The present disclosure encompasses a method of modulating microglial activity in a subject or in a sample, the method generally comprising contacting the subject or sample with a composition comprising an effective amount of a microglial rescuing agent. In another aspect, the present disclosure encompasses a method of modulating microglial metabolism in a subject in need thereof, the method generally comprising administering to the subject a composition comprising a therapeutically effective amount of a microglial rescuing agent. In yet another aspect, the present disclosure provides a composition comprising of a microglial rescuing agent for use in vitro, in vivo, or ex vivo. In some embodiments, the present invention provides a method of treating microglial dysfunction in a subject having a microglial dysfunction-associated neurodegenerative disease comprising administering to a subject a therapeutically effective amount of a microglial rescuing agent. One aspect of the present disclosure provides for a treatment of a subject with a neurodegenerative disease (e.g., AD) with creatine, a creatine analog, or Dectin-1 agonist as a treatment to enhance microglial responses by sustaining cell metabolism in individuals with single nucleotide polymorphisms (SNPs) or other mutations affecting microglial functions. Suitable compositions comprising a microglial rescuing agent are disclosed herein, for instance those described in Section I.

Provided is a process of treating a neurological disease, disorder, or condition associated with microglial dysfunction in a subject in need administration of a therapeutically effective amount of a microglial rescuing agent, so as to enhance microglial function, inhibit a neurological disease, disorder, or condition associated with microglial dysfunction, slow the progress of a neurological disease, disorder, or condition associated with microglial dysfunction, or limit the development of a neurological disease, disorder, or condition associated with microglial dysfunction.

There has been an every growing expansion of understanding of the involvement of microglia in central nervous system (CNS) disorders. A host of new molecular tools and mouse models of disease are increasingly implicating this enigmatic type of nervous system cell as a key player in conditions ranging from neurodevelopmental disorders such as autism to neurodegenerative disorders such as Alzheimer's disease and chronic pain. Contemporaneously, diverse roles are emerging for microglia in the healthy brain, from sculpting developing neuronal circuits to guiding learning-associated plasticity. The term "glial cell", as used herein, refers to connective tissue cells of the central nervous system providing structural and functional support to the neuronal cells of the central nervous system, including, for example, in the form of providing nutrition and homeostasis and/or by participation in signal transmission in the nervous system. Glial cells include, but are not limited to, astrocytes (also referred to herein as astroglial cells), microglia, and oligodendrocytes.

The term "microglial cell" or "microglia", as used herein, refers to a class of glial cells involved in the mediation of an immune response within the central nervous system by acting as macrophages. Microglial cells are capable of producing exosomes, and further include different forms of microglial cells, including amoeboid microglial cells, ramified microglial cells and reactive microglial cells. Microglial cells include reactive microglia, which are defined as quiescent ramified microglia that transform into a reactive, macrophage-like state and accumulate at sites of brain injury and inflammation to assist in tissue repair and neural regeneration.

One aspect of the present disclosure provides for a treatment of a subject with a microglial-dysfunction associated disease or disorder. The microglial-dysfunction associated disease or disorder may be any central nervous system disease or disorder in which disrupted microglial function contributes to pathology or symptoms. In non-limiting examples, microglial-dysfunction associated diseases and disorders include Alzheimer's disease, Parkinson's disease, Nasu-Hakola disease, prion diseases, multiple sclerosis, HIV-dementia, amyotrophic lateral sclerosis (ALS), frontal temporal dementia, neuropathic pain, and autism spectrum disorders. For example, microglial-dysfunction associated diseases and disorders include those described in Salter and Stevens, Nature Medicine volume 23, pages 1018-1027 (2017), the description of which is incorporated herein by reference. In some embodiments, the microglial-dysfunction associated disease or disorder is AD. In one aspect, the microglial-dysfunction associated disease or disorder is associated with mutations in TREM2 or ApoE.

As shown herein, a subject with a neurodegenerative disease (e.g., AD) or a microglial-dysfunction associated disease in a subject with ApoE or TREM2 variants can be treated with a microglial rescuing agent (optionally in combination with conventional treatments). It has been shown that creatine and analogs can provide improved neuroprotection in subjects with ApoE or TREM2 variant compared to a subject with the same disease without the ApoE or TREM2 variant.

Surprisingly, the present disclosure provides for the identification of a specific subset of patients with mutations in ApoE or TREM2 as having an improved response to a microglial rescuing agent. For example, FIG. 6 presents data showing that the creatine treatment in TREM2 knock out AD mouse model works surprisingly or unexpectedly better than in the AD mouse model without the TREM2 knock out.

Elevated risk of developing Alzheimer's disease (AD) is associated with hypomorphic variants of TREM2, a surface receptor required for microglial responses to neurodegeneration, including proliferation, survival, clustering and phagocytosis. How TREM2 promotes such diverse responses is unknown. Here, we find that microglia in AD patients carrying TREM2 risk variants and TREM2-deficient mice with AD-like pathology have abundant autophagic vesicles, as do TREM2-deficient macrophages under growth factor limitation or ER stress. Combined metabolomics and RNA-seq linked this anomalous autophagy to defective mTOR signaling, which affects ATP levels and biosynthetic pathways. Metabolic derailment and autophagy were offset in vitro through Dectin-1, a receptor that elicits TREM2-like intracellular signals, and cyclocreatine, a creatine analog that can supply ATP. Dietary cyclocreatine markedly tempered autophagy, restored microglial clustering around plaques, and decreased plaque-adjacent neuronal dystrophy in TREM2-deficient mice with amyloid-β pathology. Thus, TREM2 enables microglial responses during AD by sustaining cellular energetic and biosynthetic metabolism.

Several creatine analogs have been used in vitro and in vivo to supplement deficiency in TREM2, which can play an anti-inflammatory role in the pathogenesis of Alzheimer's. Microglia of mice and humans deficient in Trem-2 undergo increased autophagy in response to stresses such as plaques associated with AD. Treatment of Trem-2 deficient macrophages with nicotinamide mononucleotide, cyclocreatine, and phosphocreatine was able to rescue metabolic activity and prevent autophagy and cell death. In addition, excessive neuronal damage was reversed in vivo when the compounds were administered to Trem-2 deficient 5XFAD mice. The invention can be utilized to decrease the risk/severity of AD in patients carrying mutations in ApoE or Trem2 that limit the function of microglial cells.

According to an aspect of the invention a pharmaceutical composition comprising a microglial rescuing agent is used for modulating microglial activity. The method generally comprises contacting a microglia with a pharmaceutical composition comprising a microglial rescuing agent. In some embodiments, the method comprising contacting a microglia in vivo by administering a pharmaceutical composition comprising a microglial rescuing agent. Microglial activity can be measured by cell viability, mTOR signaling, presence/absence of autophagy, Syk signaling, PI3-K signaling, microgliosis, microglial clustering, neurite dystrophy, and microglial metabolism. Standard techniques and assays may be used to measure microglial activity including those described in the examples below. In some embodiments, microglial activity is measured by cell viability, wherein increased cell viability indicates increased microglial activity. In some embodiments, microglial activity is measured by mTOR signaling, wherein increased mTOR signaling indicates increased microglial activity. In some embodiments, microglial activity is measured by the presence of autophagy, wherein decreased autophagy indicates increased microglial activity. In some embodiments, contacting a microglia with a pharmaceutical composition comprising a microglial rescuing agent results in increased microglial activity relative to an untreated control.

In certain aspects, a therapeutically effective amount of a composition of the invention may be administered to a subject. Methods described herein are generally performed on a subject in need thereof. A subject in need of the therapeutic methods described herein can be a subject having, diagnosed with, suspected of having, or at risk for developing a neurological disease, disorder, or condition associated with microglial dysfunction. A determination of the need for treatment will typically be assessed by a history and physical exam consistent with the disease or condition at issue. Diagnosis of the various conditions treatable by the methods described herein is within the skill of the art. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. For example, if the disease or condition is COPD or IPF, the composition may be administered via inhalation. Alternatively, is the disease or condition is osteoarthritis, the composition may be administered via intra-articular invention. It is within the skill of one in the art, to determine the route of administration based on the disease or condition to be treated. In a specific embodiment, a composition of the invention is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents, and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response. In various embodiments, an effective amount of a microglial rescuing agent described herein can substantially enhance microglial function, inhibit a neurological disease, disorder, or condition associated with microglial dysfunction, slow the progress of a neurological disease, disorder, or condition associated with microglial dysfunction, or limit the development of a neurological disease, disorder, or condition associated with microglial dysfunction. Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the age-related disease or condition, the degenerative disease, the function-decreasing disorder, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times, or more per day, per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments mof the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction

As shown herein, the present disclosure provides for the use of a microglial rescuing agent that can increase microglial energetic metabolism in patients with mutations in genes which increase the odds for the development of Alzheimer's disease by effecting microglial function i.e. ApoE, Trem2. Microglial rescuing agents such as NMN, cyclocreatine, and phosphocreatine have been used in vitro and in the case of cyclocreatine in vivo to supplement Trem2-deficient cells or mice with AD-like pathology (5XFAD mice).

As shown herein, microglia in Trem2-deficient mice and humans carrying disease associated SNPs in TREM2 are less energetically competent and exhibit increased autophagy in response to stress such as the pathologic state associated with Alzheimer's disease. Supplementation of media with wild-type and Trem2-deficient bone marrow derived macrophages with NMN, cyclocreatine, and phosphocreatine were able to rescue Trem2-deficient cells metabolic capacity and prevent autophagy and cell death. In in vivo studies in 5XFAD and Trem2-deficient 5XFAD mice we show that we can increase microgliosis, microglial clustering around plaques, decrease microglial autophagy, decrease microglial cell death, and subsequently decrease neuronal dystrophy around plaques.

As shown herein, LC3 positive puncta was observed in microglia in individuals carrying disease associated SNPs in TREM2 and that these puncta are reminiscent of the LC3 puncta in microglia in 5XFAD mice. Trem2-deficient and ApoE-deficient mice have similar microglial response to plaque deposition. Cyclocreatine treatment of Trem2-deficient 5XFAD prevented the formation of autophagic vesicles and cell death while reversing excessive neuronal damage. This invention could treat and potentially normalize the risk for the development of Alzheimer's disease and limit disease severity in individuals carrying mutations which compromise microglial responsiveness to amyloid β plaques in Alzheimer's. Such genes include ApoE and Trem2.

Electron and confocal microscopy was used to analyze microglia from 5XFAD mice, which develop Aβ accumulation that mimics AD pathology due to the expression of mutant APP and PS1 under neural-specific elements of the mouse Thy1 promoter. Microglia from 5XFAD mice lacking TREM2 had many more autophagic vesicles than did microglia in 5XFAD mice. This observation was replicated in humans, as microglia in AD patients carrying TREM2 risk variants also had more autophagic vesicles than did microglia in AD patients with the common TREM2 variant. Autophagy is an intracellular degradation pathway essential for cellular and energy homeostasis (Galluzzi et al., 2014). It provides a mechanism for the elimination of misfolded proteins and damaged organelles and compensates for nutrient deprivation during cell starvation through recycling of cytosolic components. Because autophagy is partially regulated by mammalian target of rapamycin (mTOR)-dependent pathways (Saxton and Sabatini, 2017), the impact of TREM2-deficiency on mTOR activation was assessed and found that, indeed, anomalous autophagy reflected defective activation of mTOR signaling. Similarly, enhanced autophagy was observed in TREM2-deficient macrophages in vitro, which was further amplified by growth-factor limitation or endoplasmic reticulum (ER) stress; this provided a model system for probing biochemical and metabolic pathways in microglia during Aβ accumulation. Combined metabolomics, RNA sequencing (RNA-seq), and system analyses of TREM2-deficient macrophages confirmed the impairment of mTOR activation, energetic pathways, ATP levels, and biosynthetic pathways. Thus, TREM2 sustains cell energetic and biosynthetic metabolism through mTOR signaling. Metabolic derailment and autophagy were offset in vitro through activation of Dectin-1, a surface receptor that triggers a signaling pathway similar to that of TREM2-DAP12 (Dambuza and Brown, 2015). Metabolic abnormalities were also rescued by incubating cells with the creatine analog 1-carboxymethyl-2-iminoimidazolidine (cyclocreatine), which can passively cross membranes and, upon phosphorylation by creatine kinase, generate a supply of ATP for energy demands independent of the TREM2-mTOR axis (Kurosawa et al. 2012). Remarkably, dietary administration of cyclocreatine in 5XFAD mice lacking TREM2 prevented microglial autophagy, enhanced microglia numbers and clustering around Aβ plaques, and mitigated plaque-associated neurite dystrophy. This provides proof of principle that strategies aimed at sustaining basic microglial metabolism may be promising for treatment of AD and other neurodegenerative diseases associated with microglial dysfunction.

Example 1

Figure 1A:
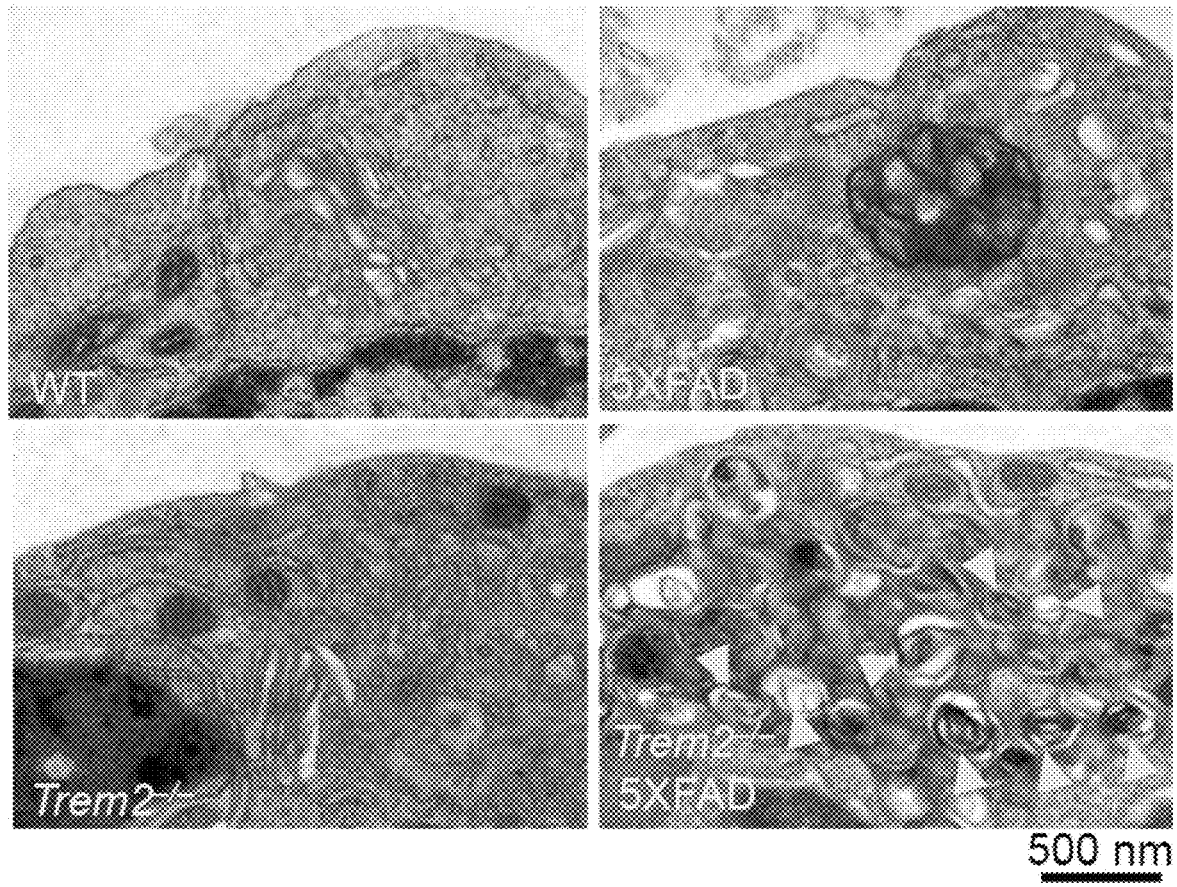
FIG. 1A, FIG. 1B, FIG. 1C, FIG. 1D, FIG. 1E and FIG. 1F depict a defect in TREM2 enhances autophagy in vivo in the 5XFAD mouse model and in AD patients.
Figure 1B:
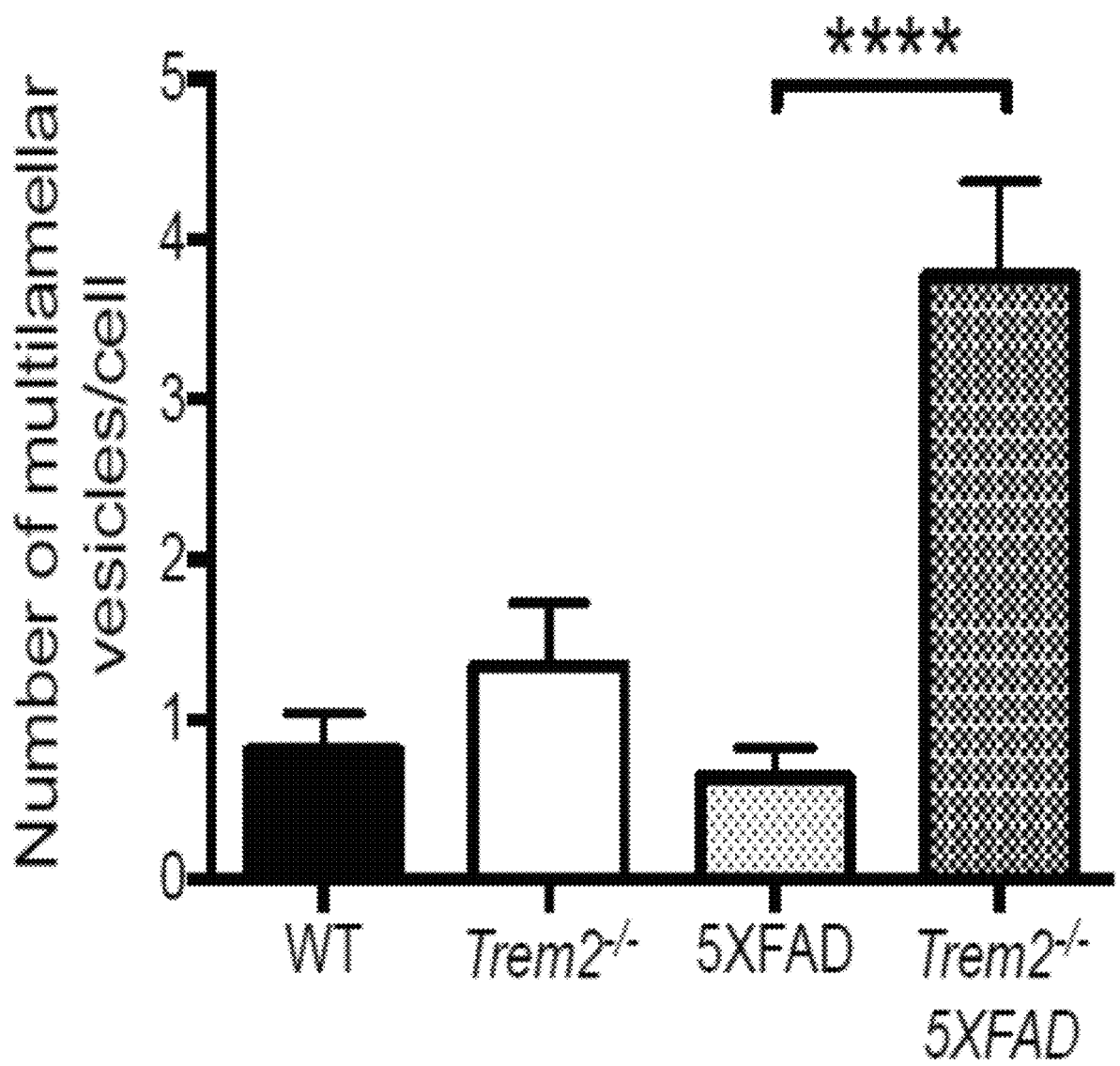
Figure 1C:
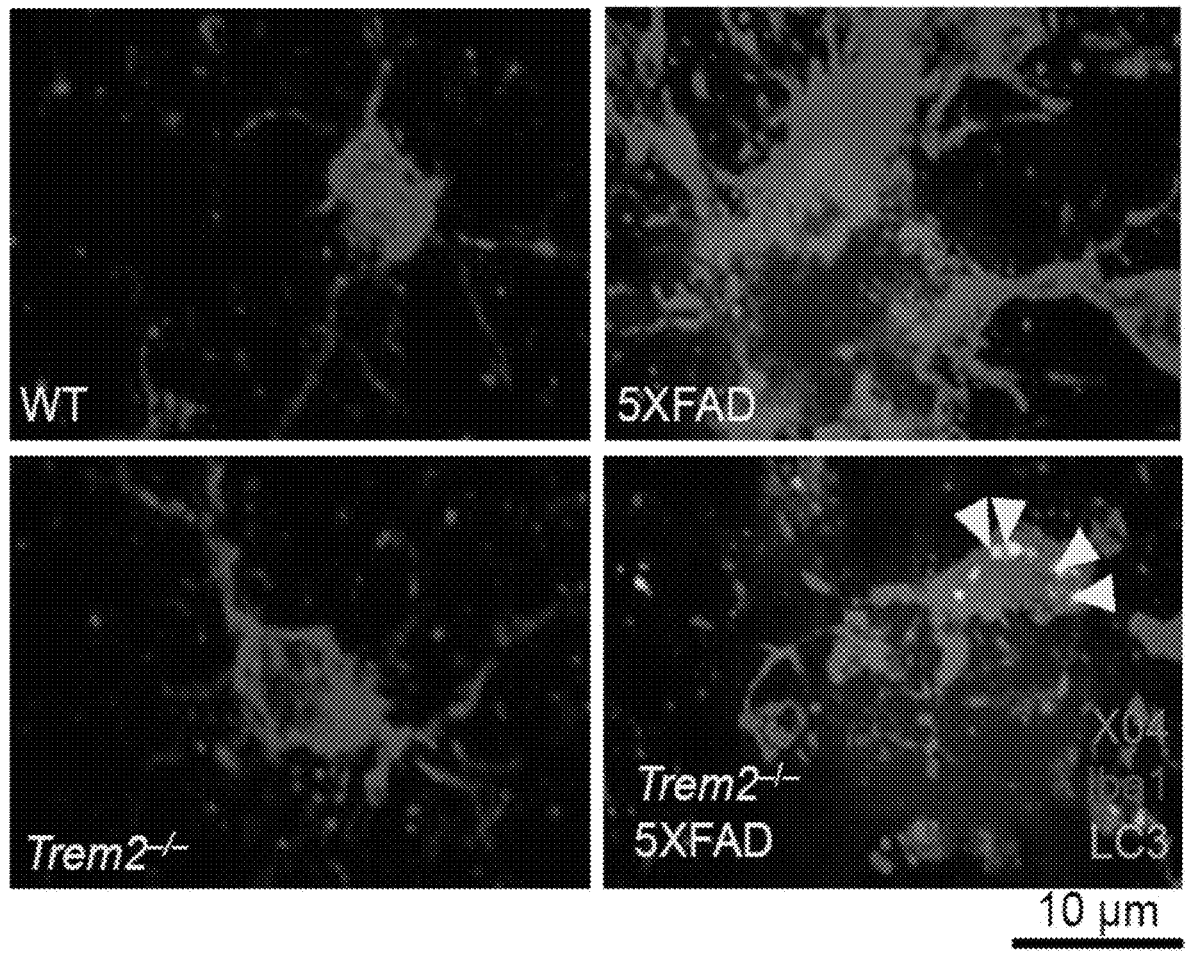
Figure 1D:
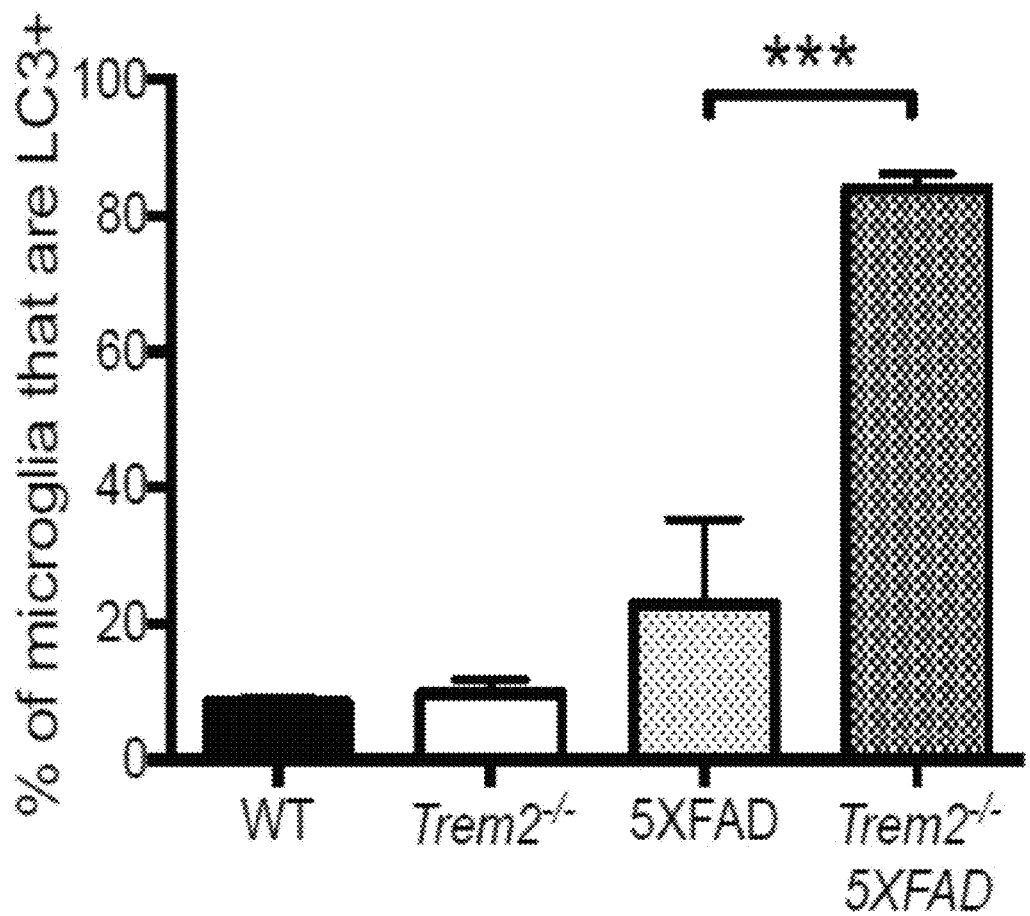
Figure 1E:
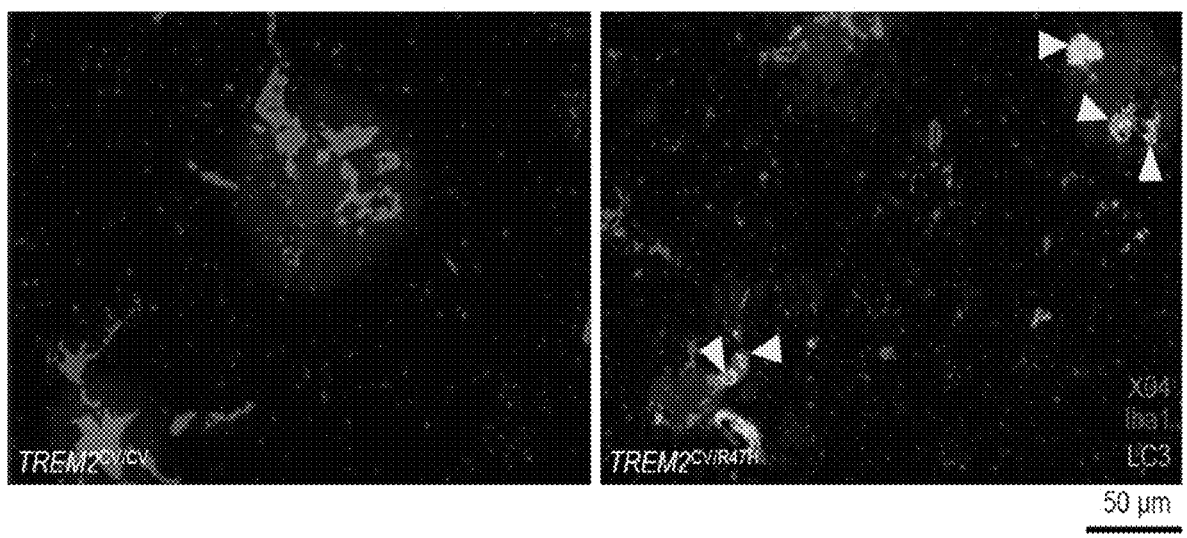
Figure 1F:
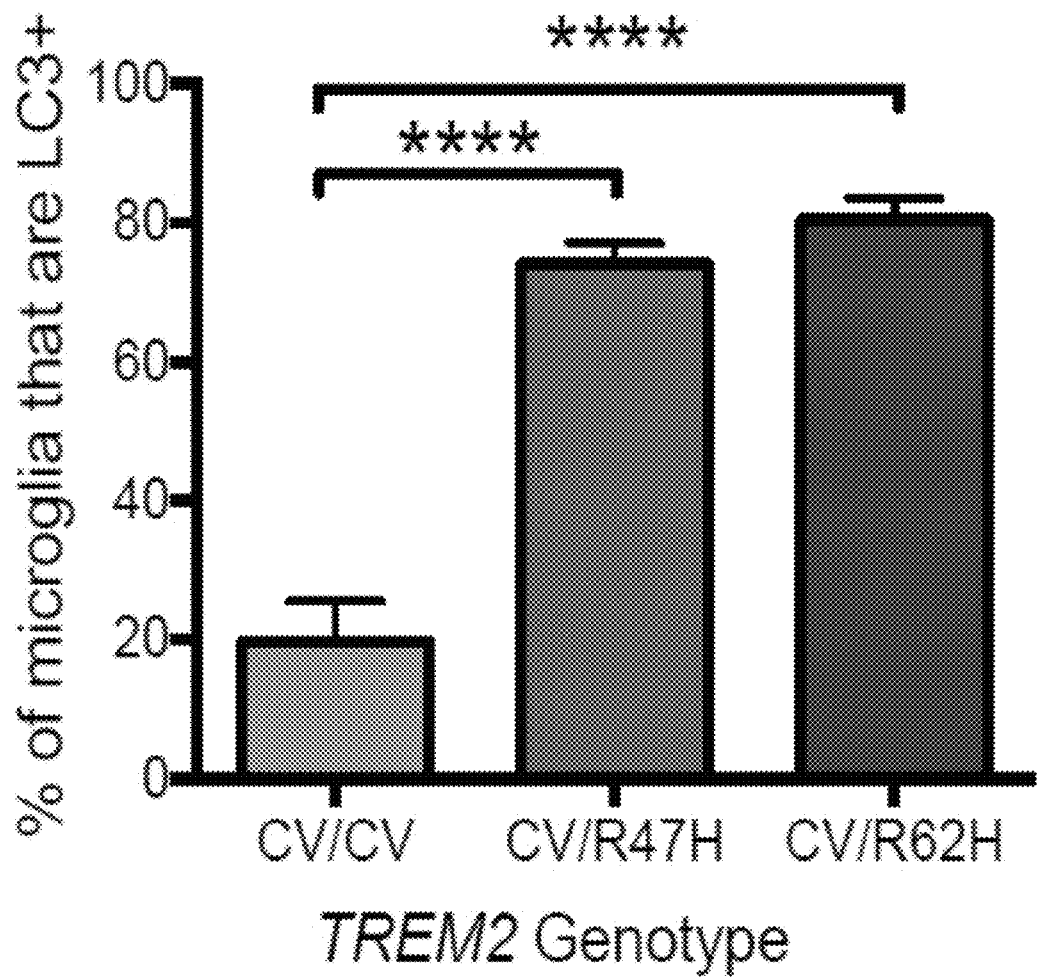

Defect in TREM2 Elicits Autophagy In Vivo in the 5XFAD Mouse Model and AD Patients To determine the impact of TREM2 deficiency on microglia function, we directly examined the structure of microglia from the 5XFAD mouse model of AD by transmission electron microscopy (TEM). Strikingly, microglia from Trem2$^{-/-}$ 5XFAD mice contained abundant multivesicular/multilamellar structures suggestive of autophagosomes, which were largely absent in microglia from 5XFAD, Trem2$^{-/-}$ or wild-type (WT) mice (FIG. 1A, FIG. 1B). To determine whether these structures reflected ongoing autophagy in situ, we examined brain sections by confocal microscopy for the presence of LC3$^+$ puncta, which denote autophagosomes decorated by lipidated LC3II (Klionsky et al., 2016). Many large LC3$^+$ puncta were evident in microglia in Trem2$^{-/-}$ 5XFAD mice, whereas LC3$^+$ puncta were sparse in microglia in WT, Trem2$^{-/-}$, and 5XFAD mice (FIG. 1C, FIG. 1D and FIG. 8). Remarkably, these observations were translatable to human disease. We observed dramatically more LC3$^+$ microglia in post-mortem brain sections from both R47H and R62H heterozygous AD patients than in those from case-matched AD patients homozygous for the common TREM2 variant (FIG. 1E, FIG. 1F, Table 1). Taken together, these data suggest that autophagic-like vesicles accumulate in the microglia of TREM2-deficient mice and humans with TREM2 risk alleles during the development of AD.

TABLE 1

Characteristics of Human Tissue Donors (Related to FIG. 1)

| Sex | Age (yrs) | Braak Stage | CDR (Est. at TOD) | CERAD | TREM2 Status |
|---|---|---|---|---|---|
| TREM2 Variant Carrier | | | | | |
| Female | 93.98 | N.A. | 3 | N.D. | R47H/CV |
| Male | 74.85 | V | 2 | Definite | R47H/CV |
| Male | 83.75 | N.A. | 3 | N.D. | R47H/CV |
| Male | 90.64 | V | 3 | Definite | R47H/CV |
| Female | 88.22 | IV | 3 | Definite | R47H/CV |
| Male | 85.64 | V | 3 | Definite | R47H/CV |
| Male | 78.23 | V | 3 | Definite | R47H/CV |
| Female | 83.16 | N.A. | 3 | N.D. | R62H/CV |
| Female | 89.31 | VI | 3 | Definite | R62H/CV |
| Female | 89.37 | N.A. | 3 | N.D. | R62H/CV |
| Female | 78.98 | N.A. | 3 | N.D. | R62H/CV |
| Case-Matched Control | | | | | |
| Female | 95.73 | VI | 3 | Definite | CV/CV |
| Male | 71.6 | VI | 3 | Definite | CV/CV |
| Male | 87.57 | V | 3 | Definite | CV/CV |
| Male | 91.08 | V | 1 | Definite | CV/CV |
| Female | 84.47 | V | 3 | Definite | CV/CV |
| Male | 80.97 | VI | 3 | Definite | CV/CV |
| Female | 85.43 | N.A. | 3 | N.D. | CV/CV |
| Female | 81.26 | VI | 3 | Definite | CV/CV |

Example 2

Figure 2A:
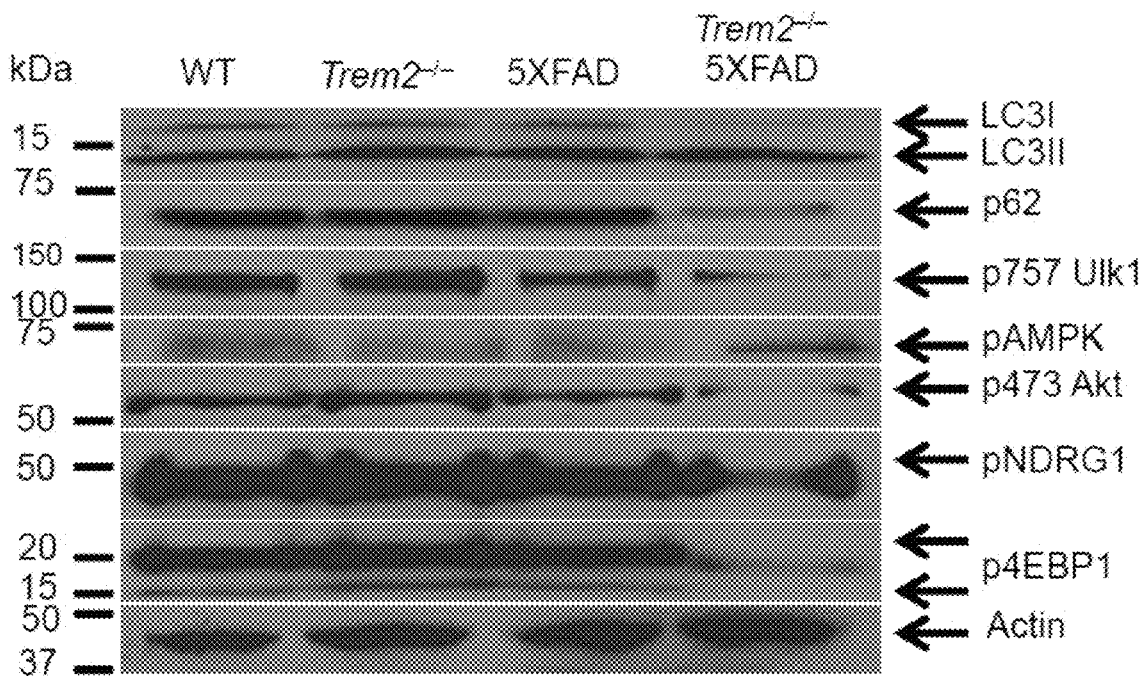
FIG. 2A, FIG. 2B, FIG. 2C, FIG. 2D, FIG. 2E and FIG. 2F depict a defect in TREM2 impairs mTOR activation and elicits AMPK activation, autophagy and cell death in microglia from 5XFAD mice.
Figure 2B:
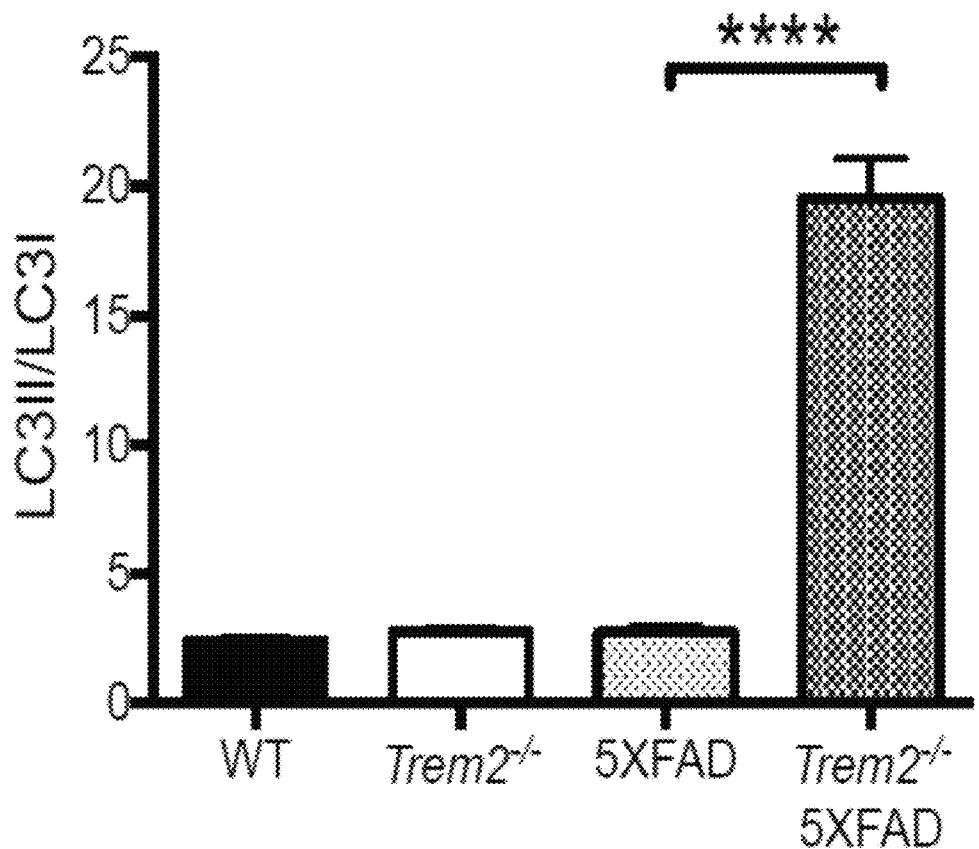

TREM 2 Deficiency Impairs mTOR Signaling and Enhances AMPK Activation in Microglia To corroborate the association between TREM2 deficiency and increased autophagy, we performed biochemical analyses on sorted microglia ex vivo. The ratio of lipidated LC3II to non-lipidated LC3I was markedly higher in microglia from Trem2$^{-/-}$ 5XFAD mice than in microglia from 5XFAD mice, consistent with the increased number of autophagic vesicles in TREM2-deficient microglia. To determine whether the increase in autophagosomes was due to activation of autophagy or blockade of lysosomal degradation, we measured protein and mRNA levels of p62, an autophagy cargo protein that is digested by lysosomal enzymes. The amount of p62 protein was lower in microglia from Trem2$^{-/-}$ 5XFAD mice than in microglia from 5XFAD mice. This difference was unrelated to transcription, as p62 (Sqstm1) mRNA levels were similar. Thus, TREM2 deficiency results in bona fide autophagy (FIG. 2A, FIG. 2B and FIG. 9A).

Why is autophagic flux amplified in 5XFAD mice lacking TREM2? Autophagy often reflects an adaptive response to stress that can occur when cells cannot satisfy increased demands for energy and protein synthesis (Kroemer et al., 2010). Since the serine/threonine kinase target of rapamycin (mTOR) has a crucial role in stimulating both energetic and anabolic metabolism, cell growth and proliferation (Laplante and Sabatini, 2012), we hypothesized that the autophagy observed in microglia in Trem2$^{-/-}$ 5XFAD mice might result from a defect in mTOR signaling. mTOR signals through two distinct complexes, mTORC1 and mTORC2. Immunoblotting of sorted microglia from Trem2$^{-/-}$ 5XFAD and 5XFAD mice revealed decreased phosphorylation of 4EBP1, an mTORC1 effector, as well as AKT at serine 473 and NDRG1, both mTORC2 effectors, in the TREM2-deficient microglia (FIG. 2A). Ulk1, a key inducer of autophagy, which is inhibited by mTOR signaling through phosphorylation at serine 757 (Kim et al., 2011), was less phosphorylated in microglia from Trem2$^{-/-}$ 5XFAD mice, consistent with reduced mTOR activation and increased autophagy. Impaired mTOR signaling was associated with phosphorylation of AMP-activated protein kinase (AMPK), a sensor of low energy states (FIG. 2A).

Figure 2C:
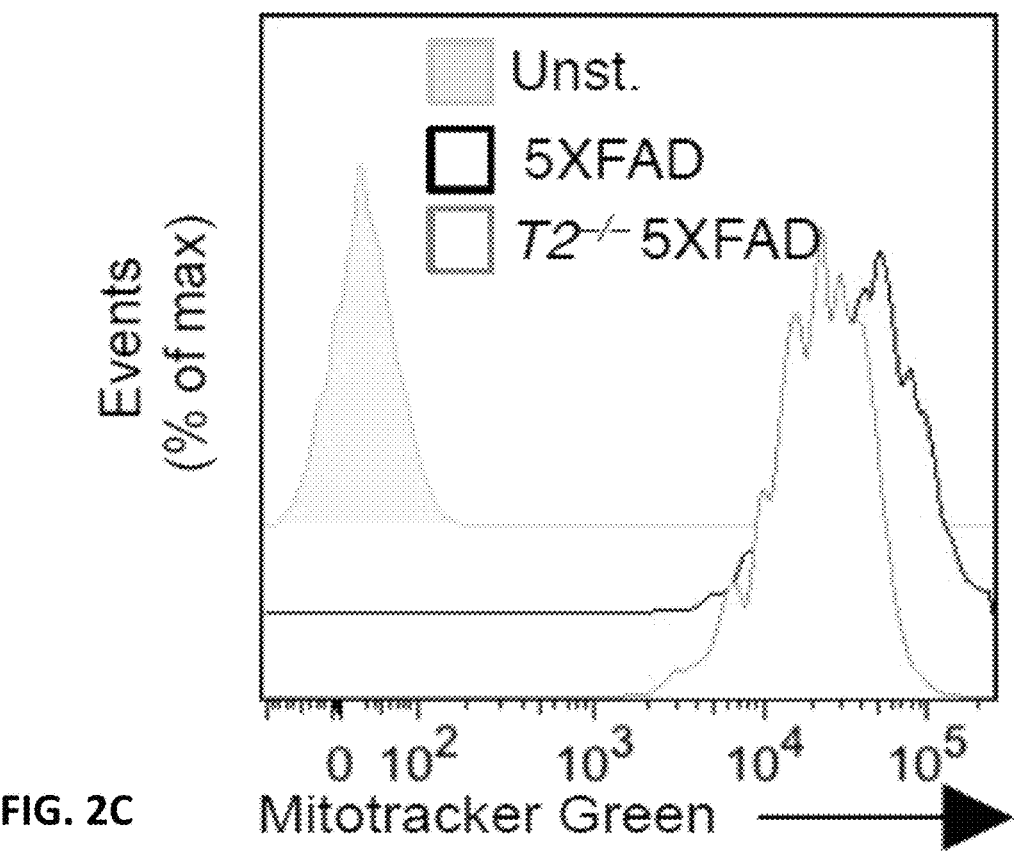
Figure 2D:
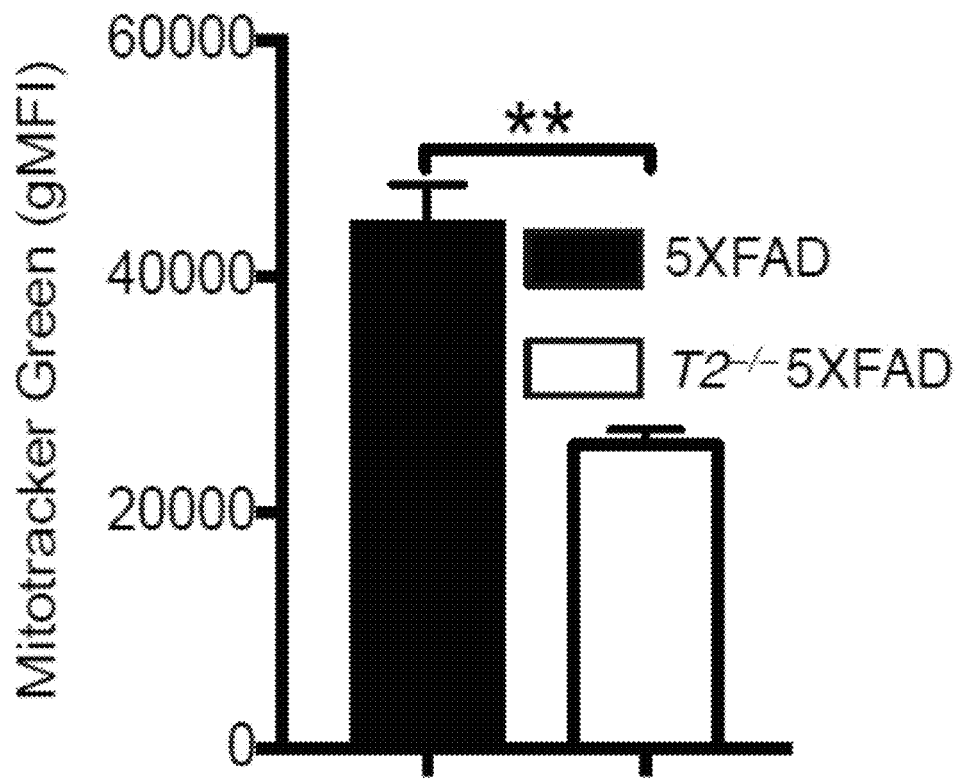

Providing further evidence for defective energetic and anabolic metabolism associated with TREM2 deficiency, microglia from Trem2$^{-/-}$ 5XFAD mice had a lower mitochondrial mass than did microglia from 5XFAD mice (FIG. 2C, FIG. 2D). Furthermore, gene expression microarray analyses of sorted microglia from Trem2$^{-/-}$ 5XFAD and 5XFAD mice revealed decreased expression of genes encoding translation initiation factors, ribosomal proteins, glucose transporters, glycolytic enzymes, as well as the transcription factor HIF1α that controls glycolysis in TREM2-deficient microglia (FIG. 9B-FIG. 9G). Taken together, these data demonstrate that during the development of AD, TREM2 deficiency derails the mTOR pathway, anabolic and energetic metabolism in microglia, which induces compensatory autophagy in both mice and humans.

Figure 2E:
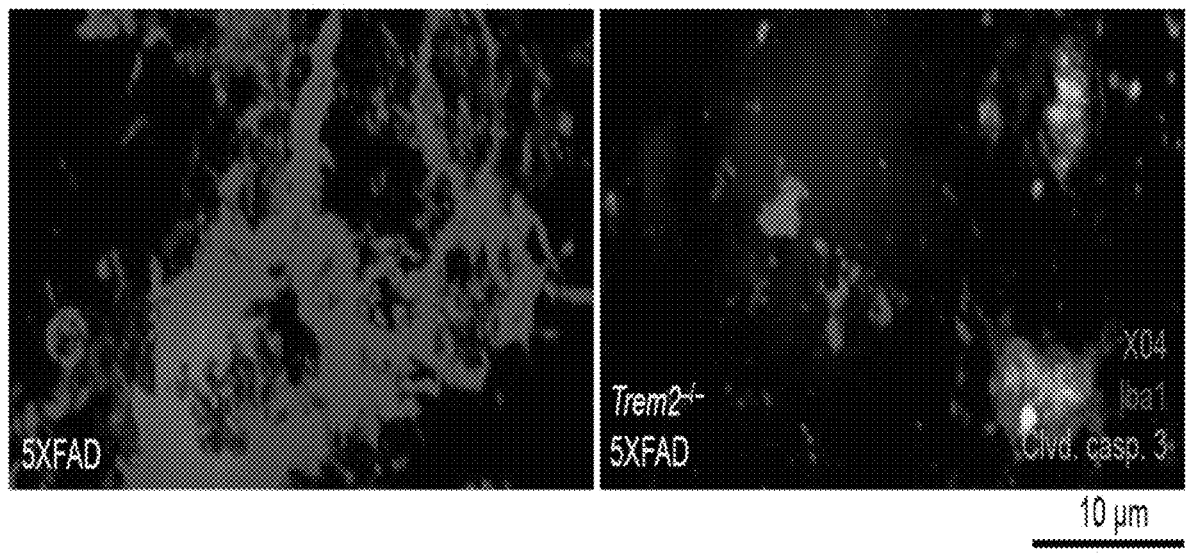
Figure 2F:
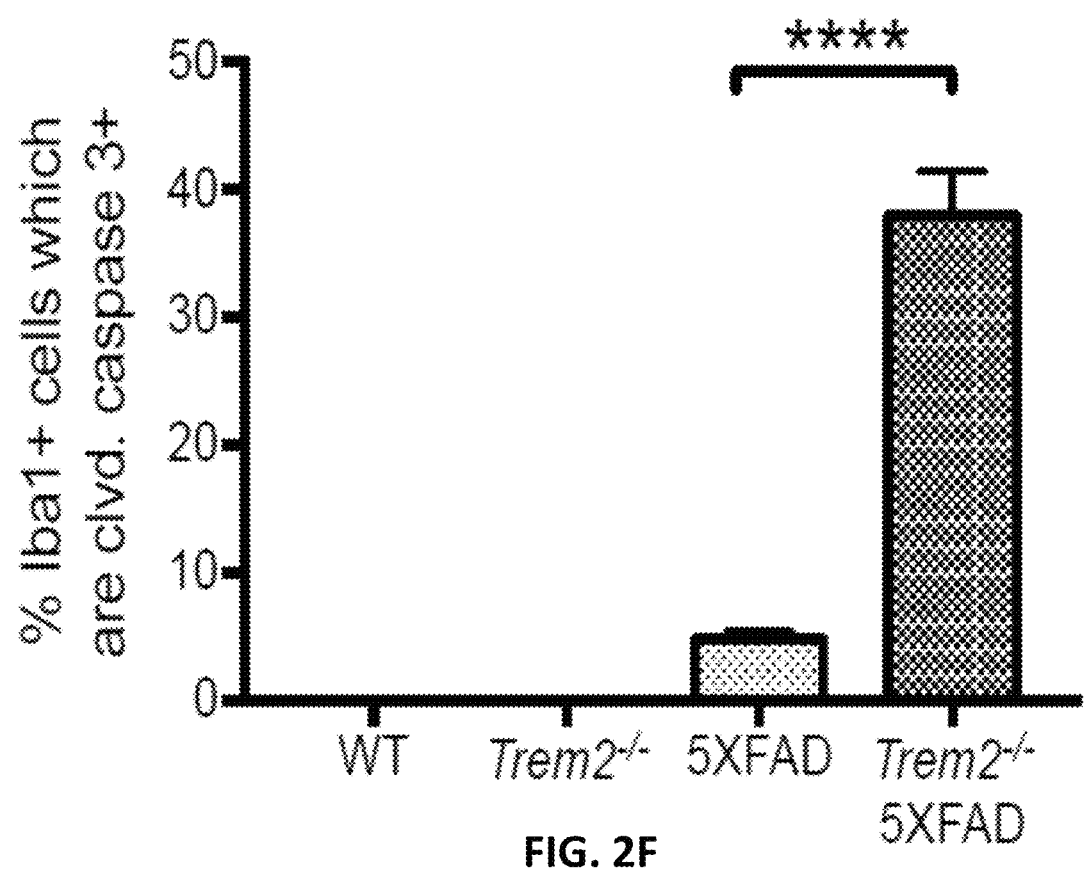

To determine whether autophagy in TREM2-deficient microglia can effectively compensate for the metabolic defects in vivo and prevent apoptosis, we examined brain sections by confocal microscopy for the presence of cleaved caspase-3, an indicator of apoptosis. We found that cleaved caspase-3 was much more abundant in microglia in Trem2$^{-/-}$ 5XFAD mice than in microglia in 5XFAD mice (FIG. 2E, FIG. 2F). Additionally, the percentage of microglia with colocalization of cleaved caspase-3 and LC3$^+$ puncta was higher in Trem2$^{-/-}$ 5XFAD mice than in 5XFAD mice (FIG. 9H, FIG. 9I). Thus, autophagy may not be sufficient to sustain the microglial response to stress, at least at the late time point of disease progression analyzed.

Example 3

Figure 3A:
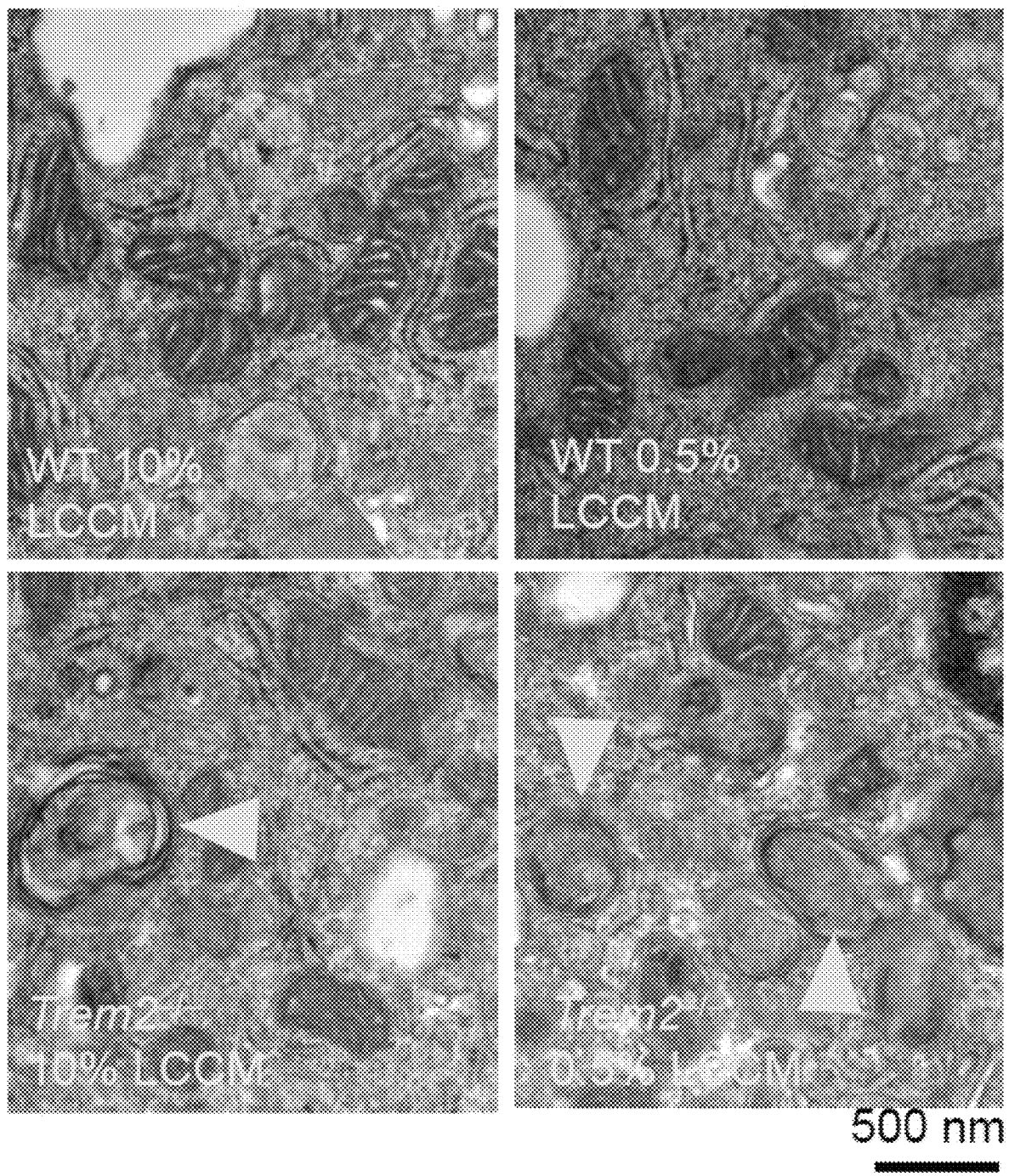
FIG. 3A, FIG. 3B, FIG. 3C, FIG. 3D, FIG. 3E, FIG. 3F, FIG. 3G, FIG. 3H, FIG. 3I, FIG. 3J and FIG. 3K depict TREM2 deficiency affects mTOR signaling and induces autophagy in BMDM.
Figure 3B:
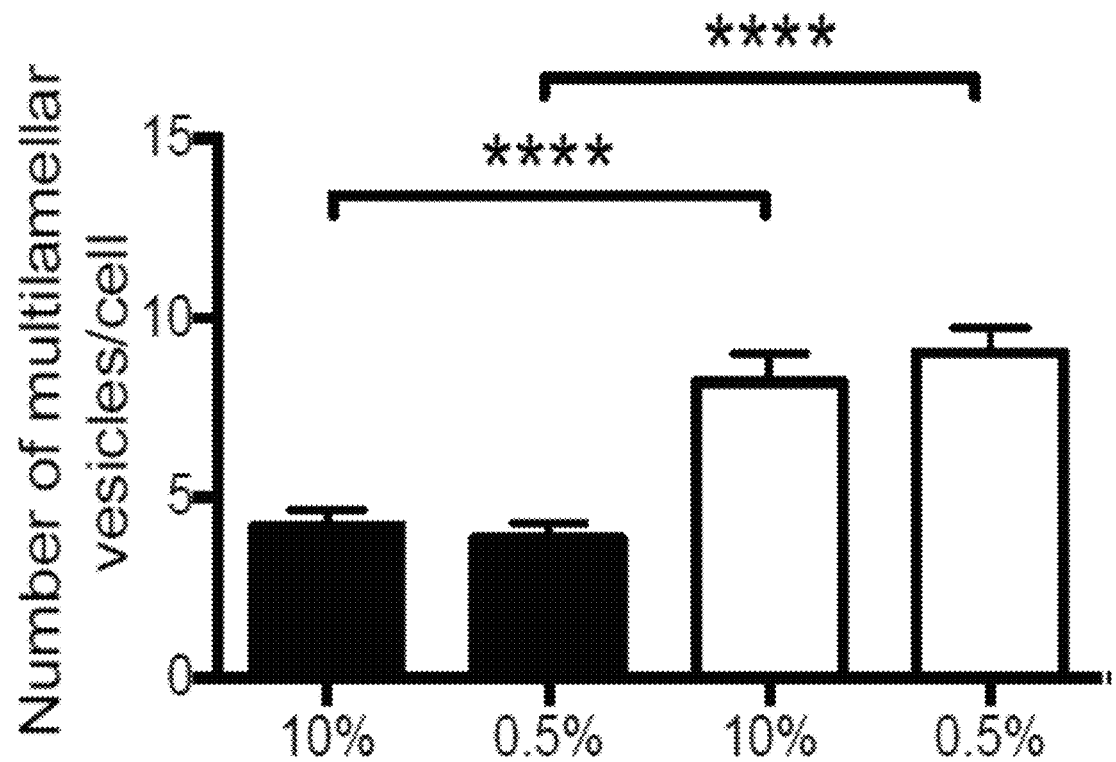
Figure 3C:
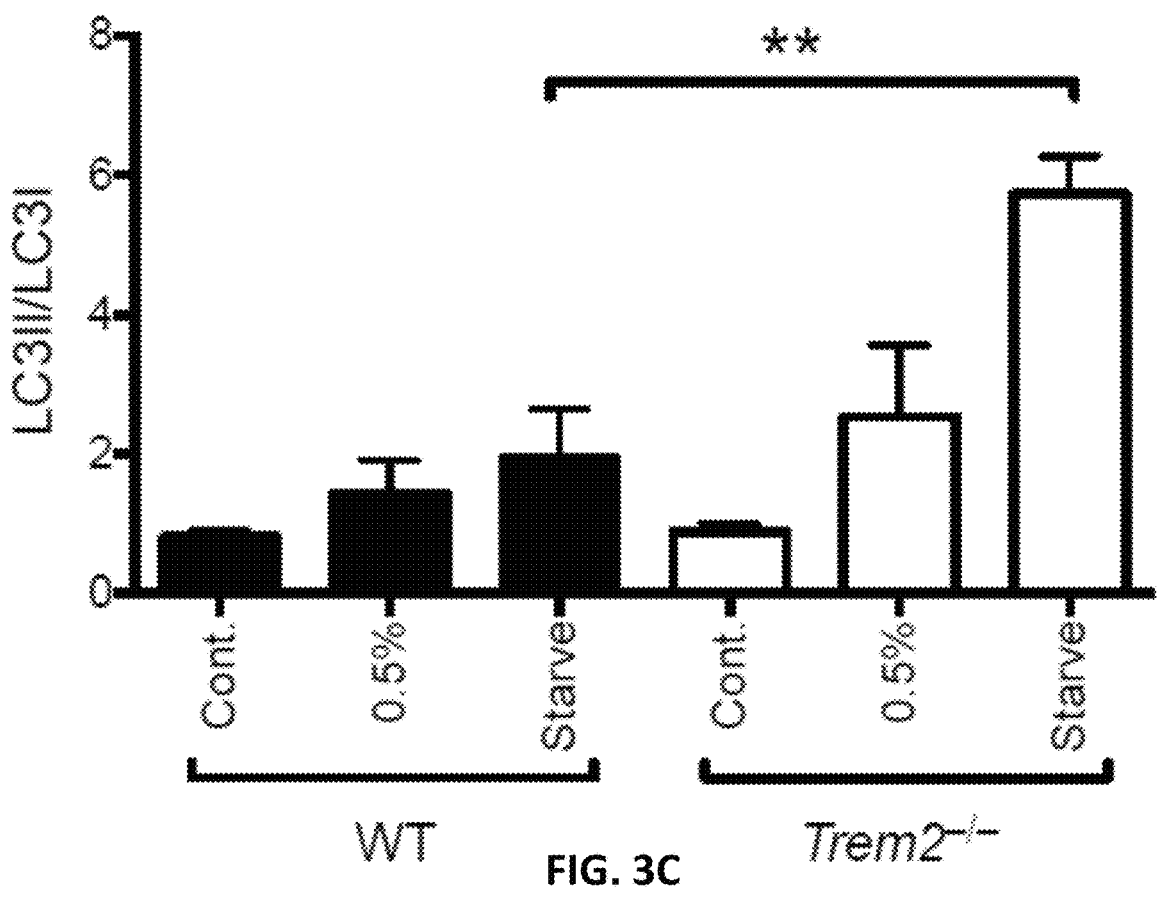
Figure 3D:
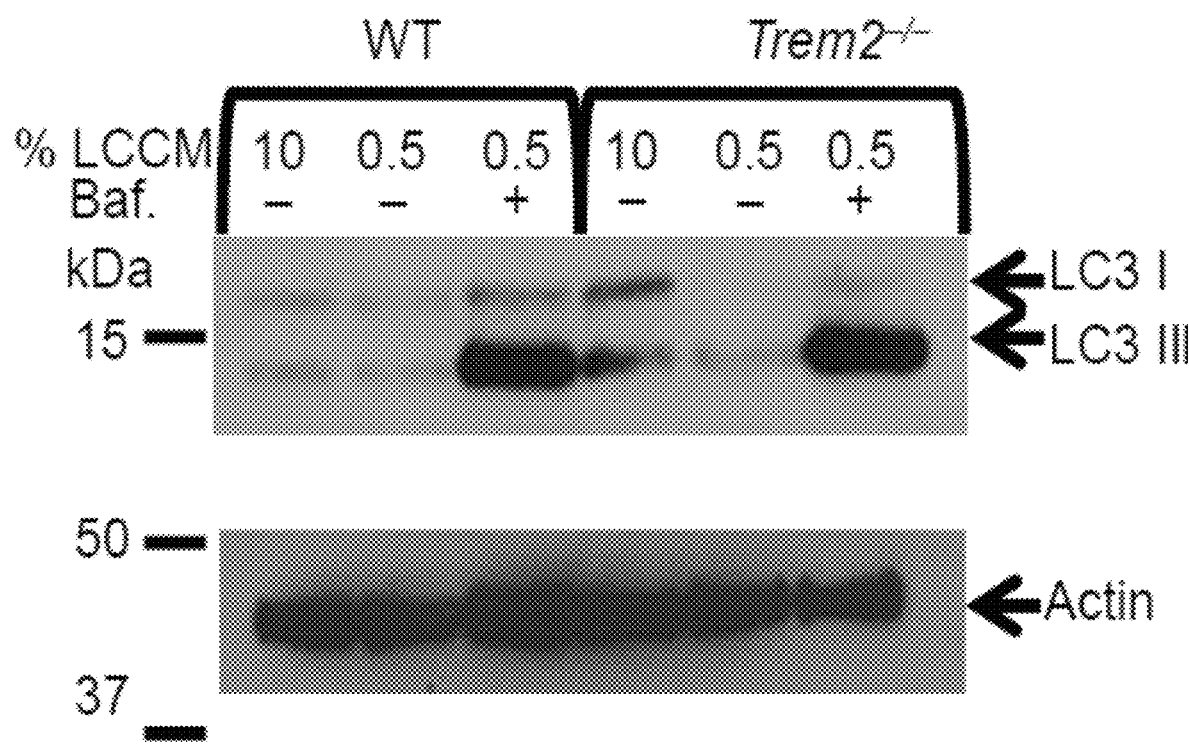
Figure 3E:
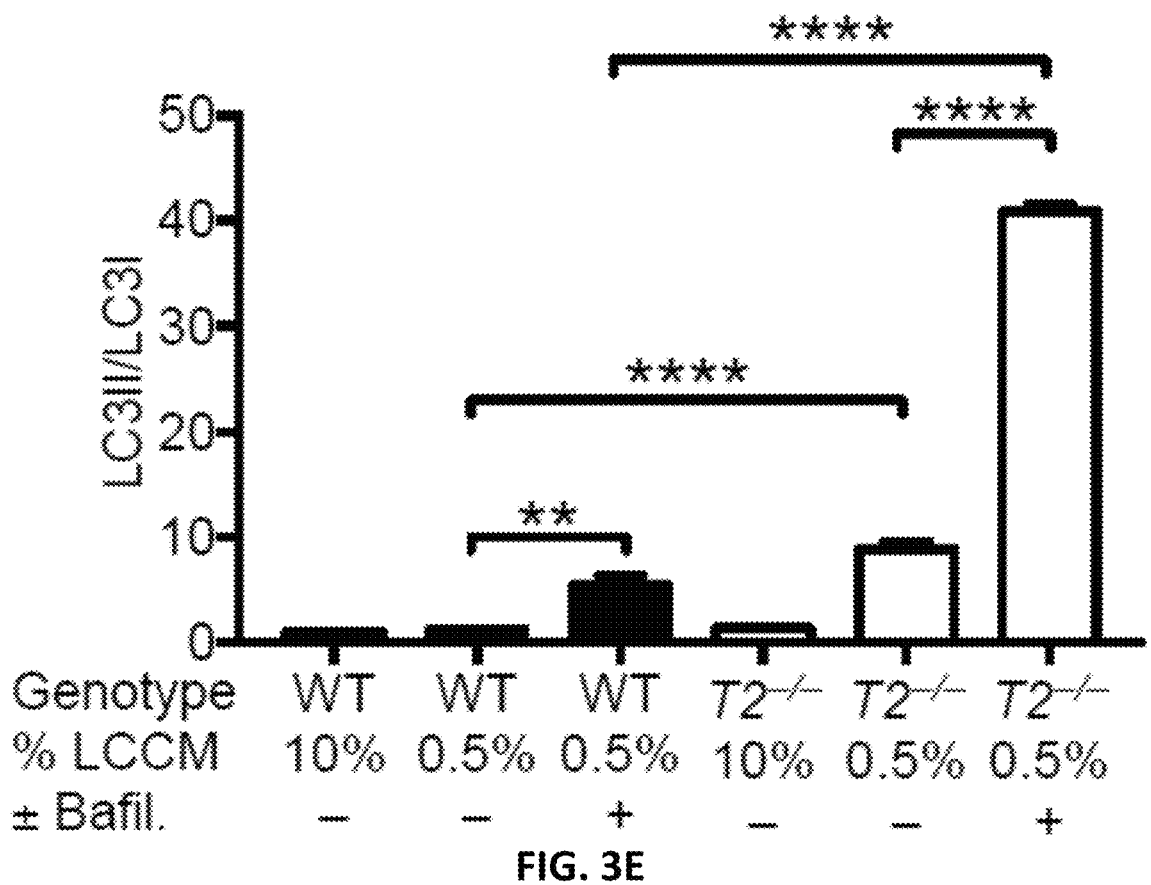
Figure 3F:
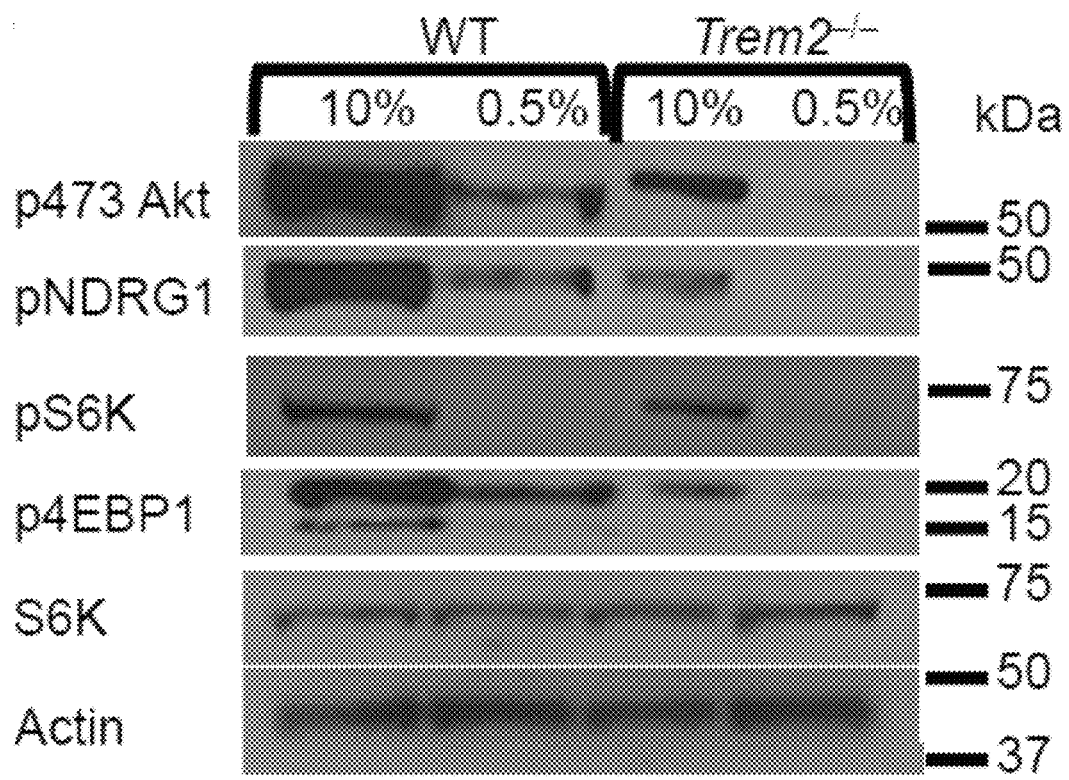
Figure 3G:
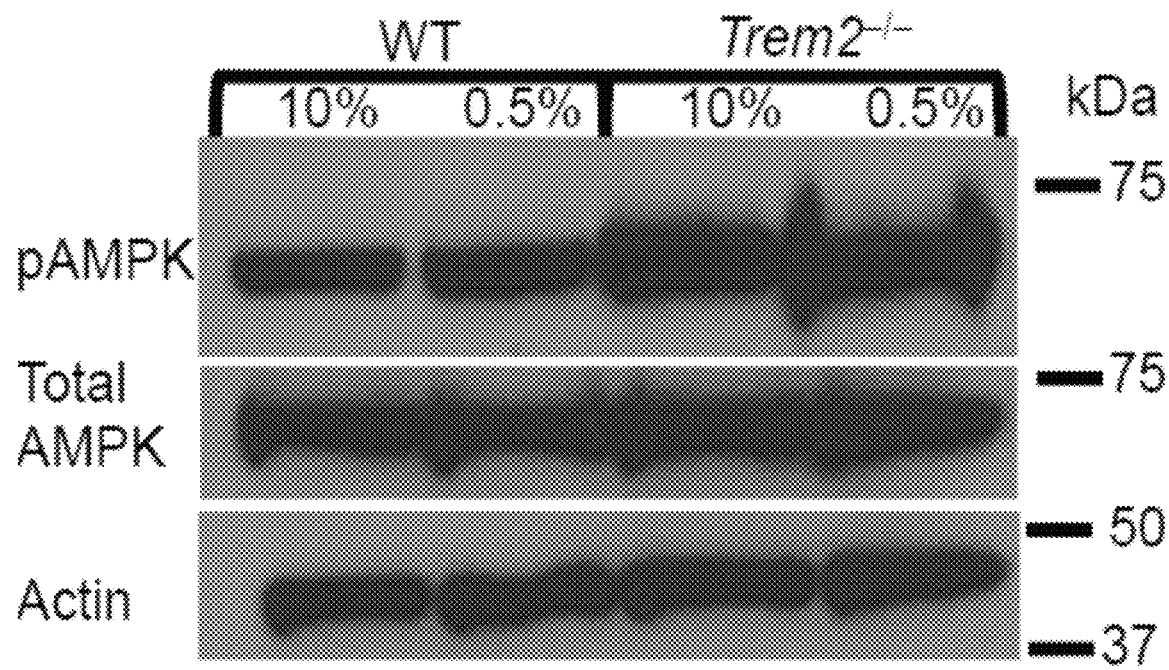

Macrophages Lacking TREM2 Inadequately Signal through mTOR and Undergo More Autophagy We then asked whether TREM2-deficiency could derail mTOR signaling in bone marrow-derived macrophages (BMDMs) from WT and Trem2$^{-/-}$ mice in vitro. To mimic the metabolic stress that occurs during disease, we used growth factor deprivation. BMDMs were cultured overnight in concentrations of CSF1-containing L cell-conditioned medium (LCCM) ranging from optimal to limiting (10% to 0.5%). Trem2$^{-/-}$ BMDMs contained more autophagic vesicles (FIG. 3A, FIG. 3B) and had a higher LC3II/LC3I ratio than did WT cells when CSF-1 was limiting (FIG. 3C). Addition of the lysosomal inhibitor bafilomycin greatly increased LC3II in Trem2$^{-/-}$ BMDMs, confirming that the increase in autophagosomes was due to increased autophagic flux rather than reduced autophagosome degradation (FIG. 3D, FIG. 3E).

Figure 3H:
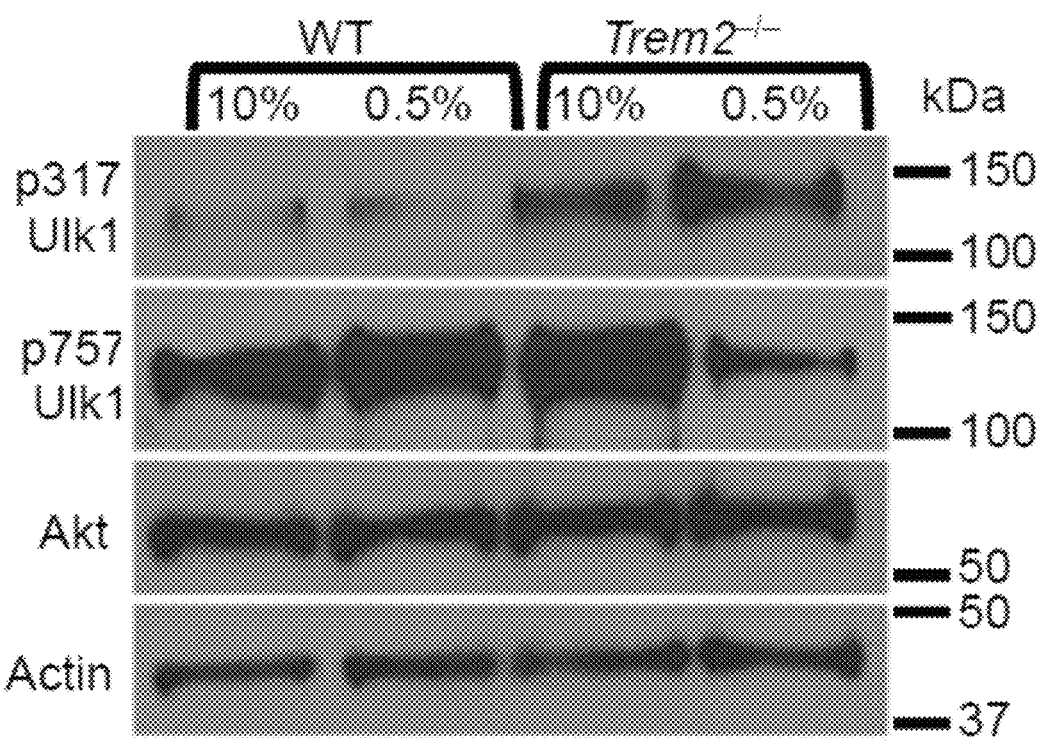

As observed in sorted microglia, autophagy in BMDMs was linked to impaired mTOR signaling. Trem2$^{-/-}$ BMDMs had less phosphorylated 4EBP1, 473S AKT and NDRG1 (FIG. 3F) and more phosphorylated AMPK (FIG. 3G) in both optimal CSF1 and limiting CSF1 than did WT BMDMs. In limiting CSF1, Trem2$^{-/-}$ BMDMs had decreased inhibitory phosphorylation of Ulk1 at serine 757, while activating phosphorylation of Ulk1 at serine 317 increased (FIG. 3H). Thus, lack of TREM2 suppressed mTOR activation and elicited compensatory AMPK and Ulk1 activation and autophagy in BMDMs in response to metabolic stress, very similar to our observations of microglia in 5XFAD mice.

Figure 3I:
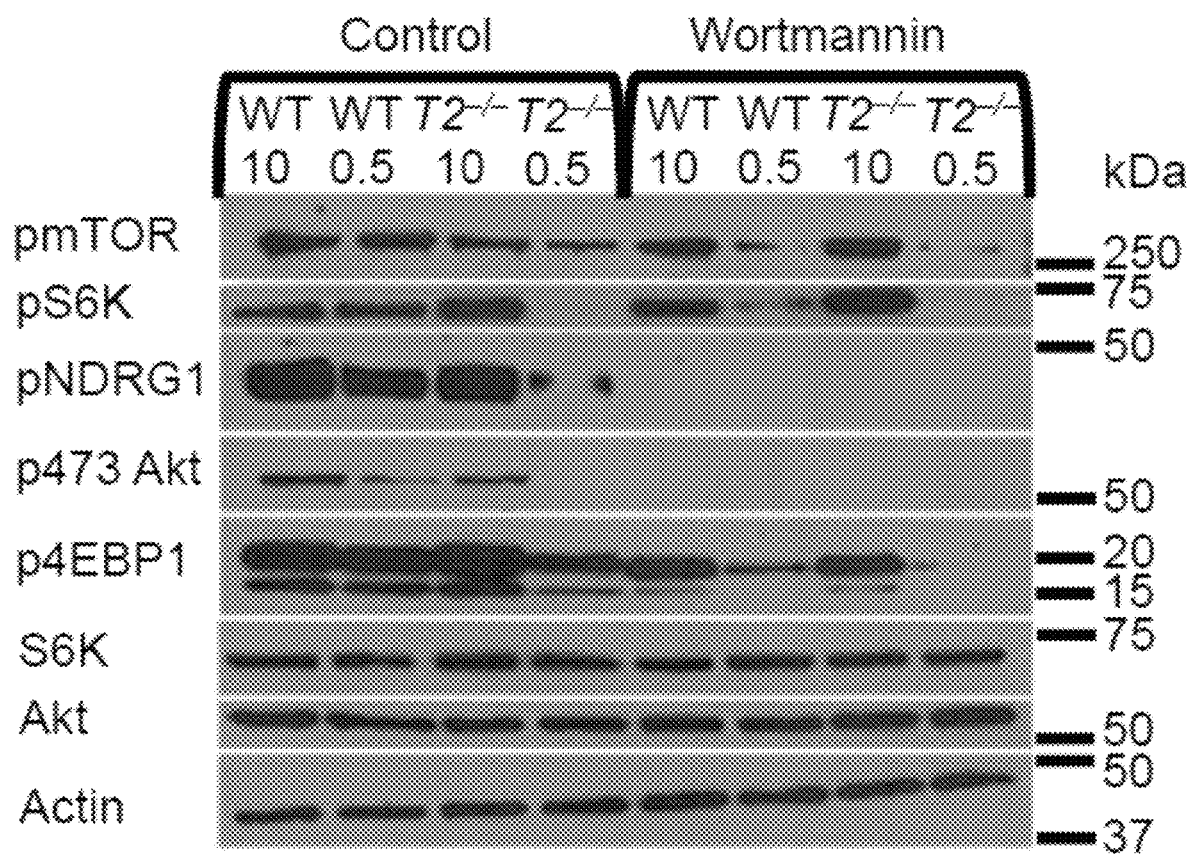
Figure 3J:
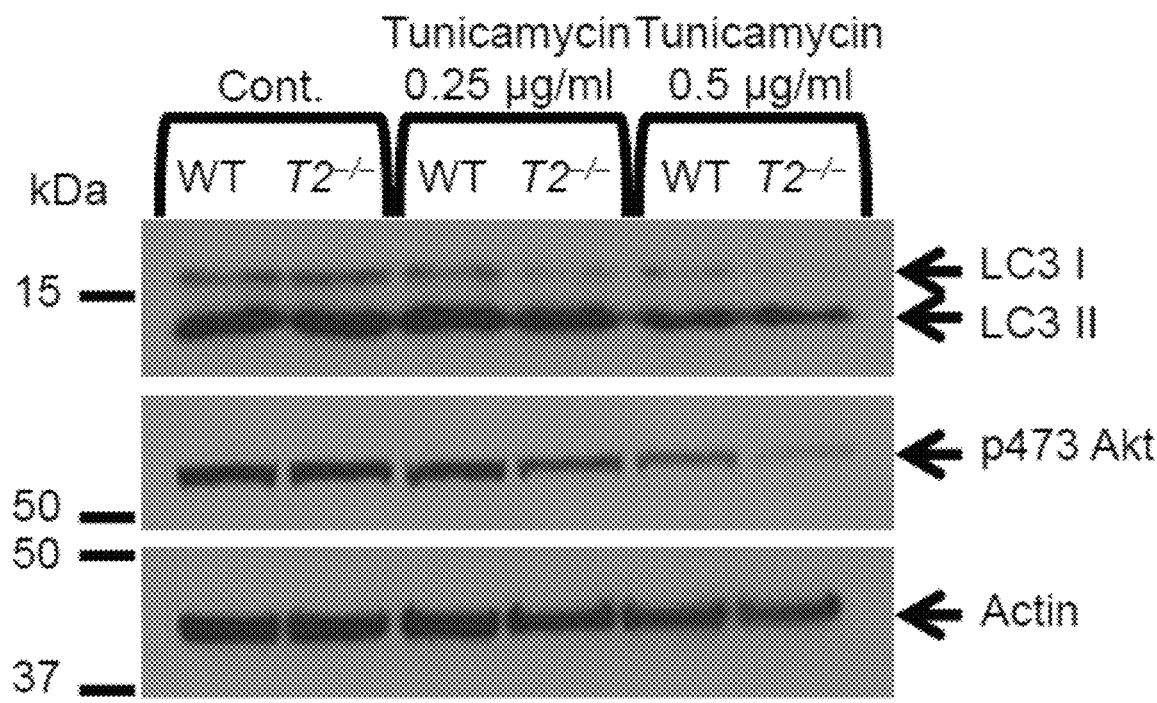
Figure 3K:
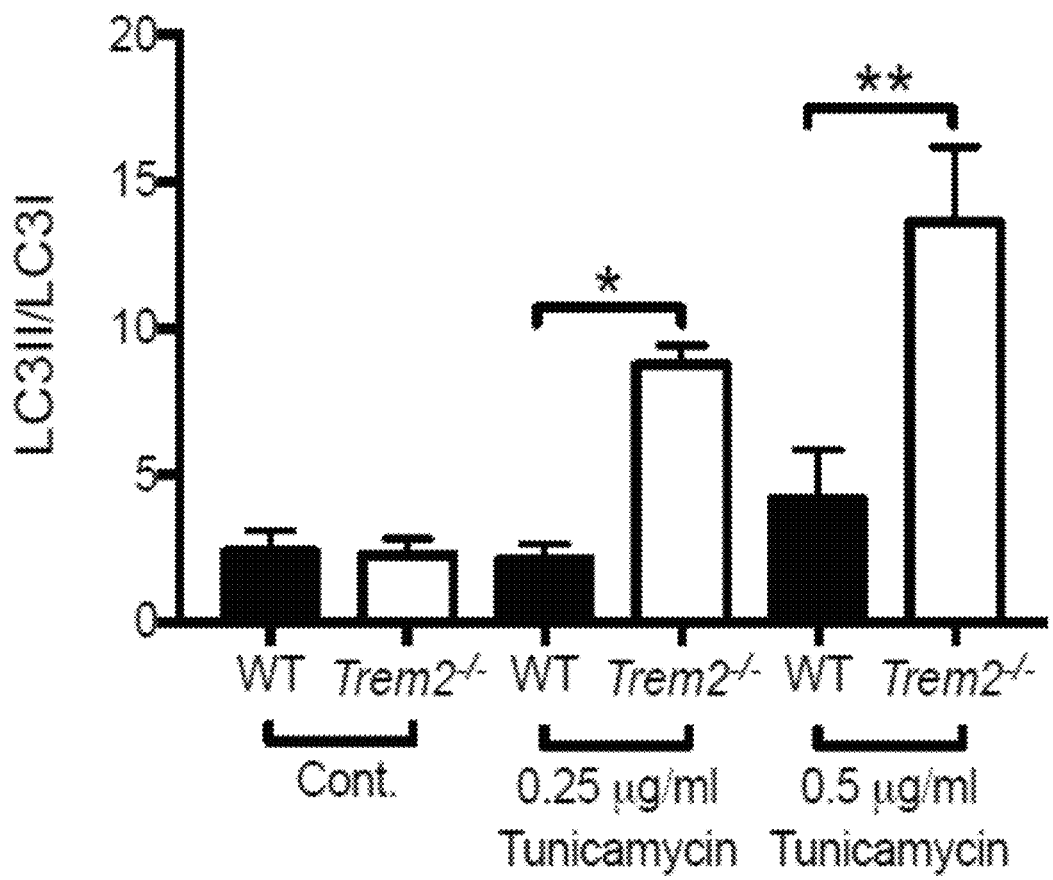

As TREM2 signaling adapters DAP12 and DAP10 have been shown to activate P I3-K, which in turn can activate mTOR, we asked whether enhanced mTOR signaling in WT BMDM compared to Trem2$^{-/-}$ BMDM was dependent on PI3-K. Inhibition of PI3-K with wortmannin or LY294002 caused a major reduction in phosphorylation of mTOR and its downstream targets in WT BMDMs; the residual amount of phosphorylation was similar to that seen in Trem2$^{-/-}$ BMDMs (FIG. 3I and FIG. 10A). In addition to limiting CSF1, other stressors may differentially modulate mTOR signaling and autophagy in WT and Trem2$^{-/-}$ BMDMs. Treatment with tunicamycin, which provokes endoplasmic reticulum (ER) stress, the unfolded protein response and autophagy, induced greater LC3II/LC3I ratios and less Akt S473 phosphorylation in Trem2$^{-/-}$ BMDMs than in WT BMDMs (FIG. 3J, FIG. 3K). Thus, TREM2 deficiency affects cell responses to multiple stressors.

TREM2 signaling may not just have a more pronounced effect on cells under stress conditions, but may actually increase under such conditions. When cultured in media containing 10% FBS, TREM2 reporter cells, which express GFP upon TREM2 engagement, showed some activation (FIG. 10B) (Wang et al., 2015). However, upon serum starvation, a significantly higher proportion of reporter cells became activated, possibly due to exposure of the TREM2 ligand phosphatidylserine on the outer leaflet of stressed cells. This activation could be blocked by inclusion of an anti-TREM2 antibody. Thus, in multiple in vitro settings of stress, TREM2-expressing cells are more able to sustain mTOR activation and suppress autophagy in a PI3K-dependent manner than are cells lacking TREM2.

Example 4

TREM2 Deficiency Curtails Anabolic and Energetic Metabolism in BMDMs

Figure 4A:
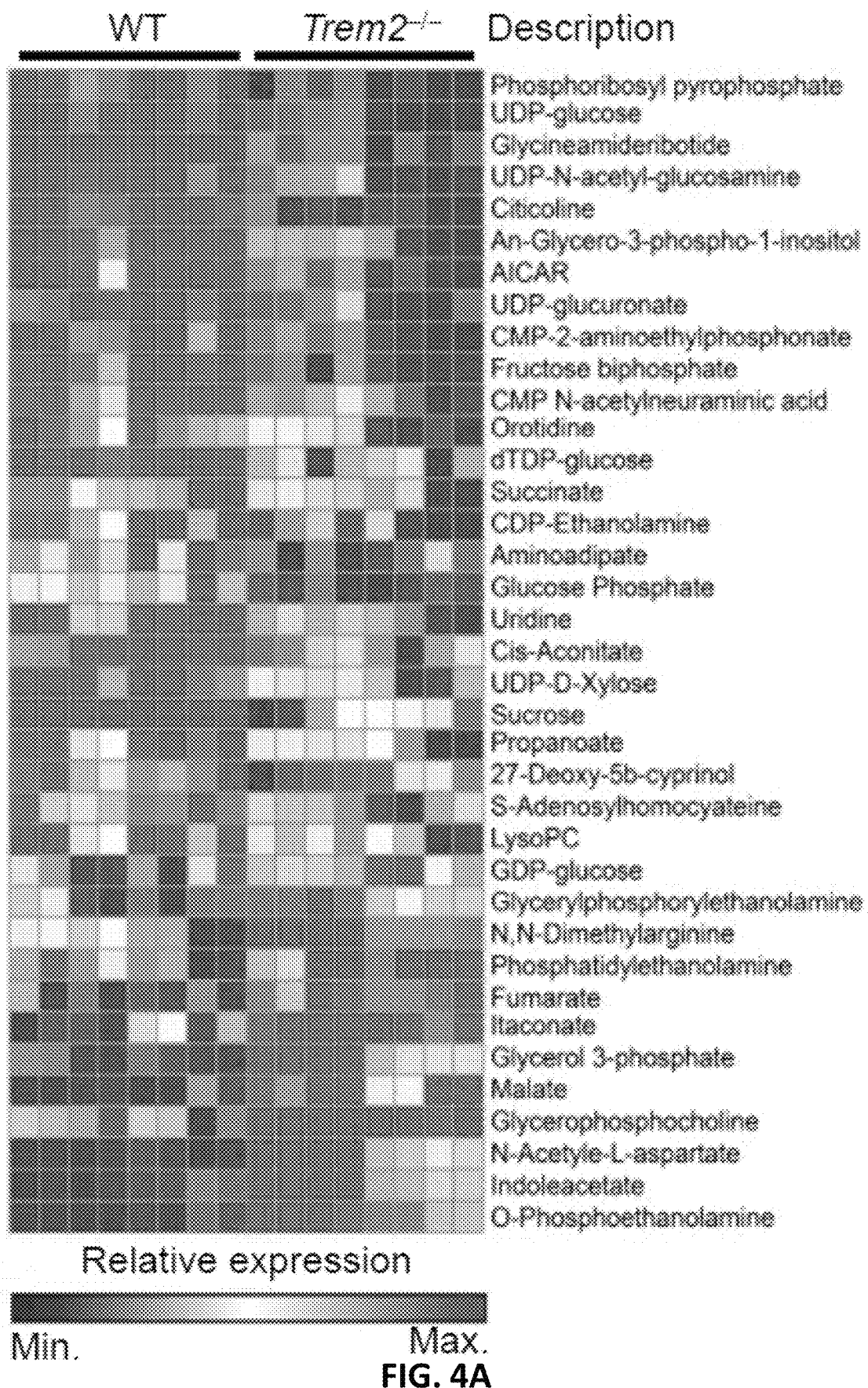
FIG. 4A, FIG. 4B, FIG. 4C, FIG. 4D, FIG. 4E, FIG. 4F and FIG. 4G depict TREM2 deficiency reduces anabolic and energetic metabolism in BMDM.
Figure 4B:
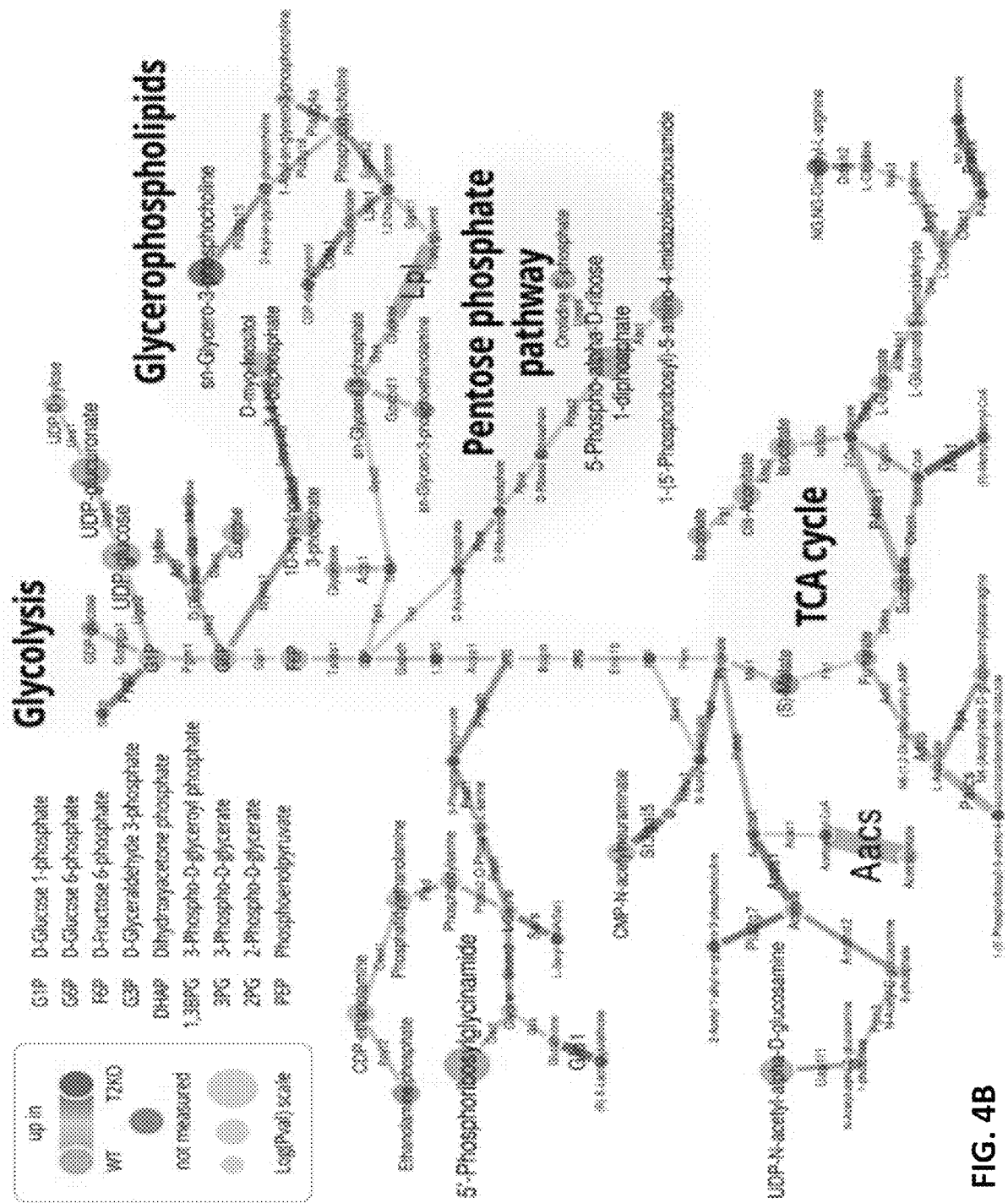

To directly demonstrate the impact of TREM2 deficiency on energetic and anabolic pathways in BMDMs, we performed mass spectrometry to quantify cellular metabolites and RNA sequencing (RNA-seq) to quantify mRNA levels of metabolic enzymes. Analysis of metabolite data alone, or in combination with RNA-Seq data by a systems-based algorithm, revealed widespread differences between WT and Trem2$^{-/-}$ BMDMs in various metabolic pathways (Sergushichev et al., 2016). Compared to WT BMDMs in optimal CSF-1, Trem2$^{-/-}$ BMDMs cultured under the same conditions exhibited: 1) a marked decrease of key intermediates in the synthesis of nucleotides (e.g. phosphoribosyl pyrophosphate), N-glycosylated proteins (e.g. UDP-glucose), and phospholipids (e.g. CDP-ethanolamine); 2) a decrease in glycolytic metabolites (e.g. glucose 6-phosphate and fructose bisphosphate) and tricarboxylic acid (TCA) cycle intermediates (citrate and succinate); and 3) an increase in catabolic products of amino acids (e.g. indolacetate) and phospholipid precursors (e.g. glycerol 3-phosphate) (FIG. 4A, FIG. 11A). Moreover, a selective increase in malate and fumarate suggested an enhanced malate-aspartate shuttle to sustain defective NADH oxidation and NAD regeneration (FIG. 4A). Unbiased network analysis combining metabolic and RNA-seq data highlighted defects in metabolites and enzymes involved in glycolysis, TCA cycle and pentose phosphate pathway in Trem2$^{-/-}$ BMDMs (FIG. 4B).

Figure 4C:
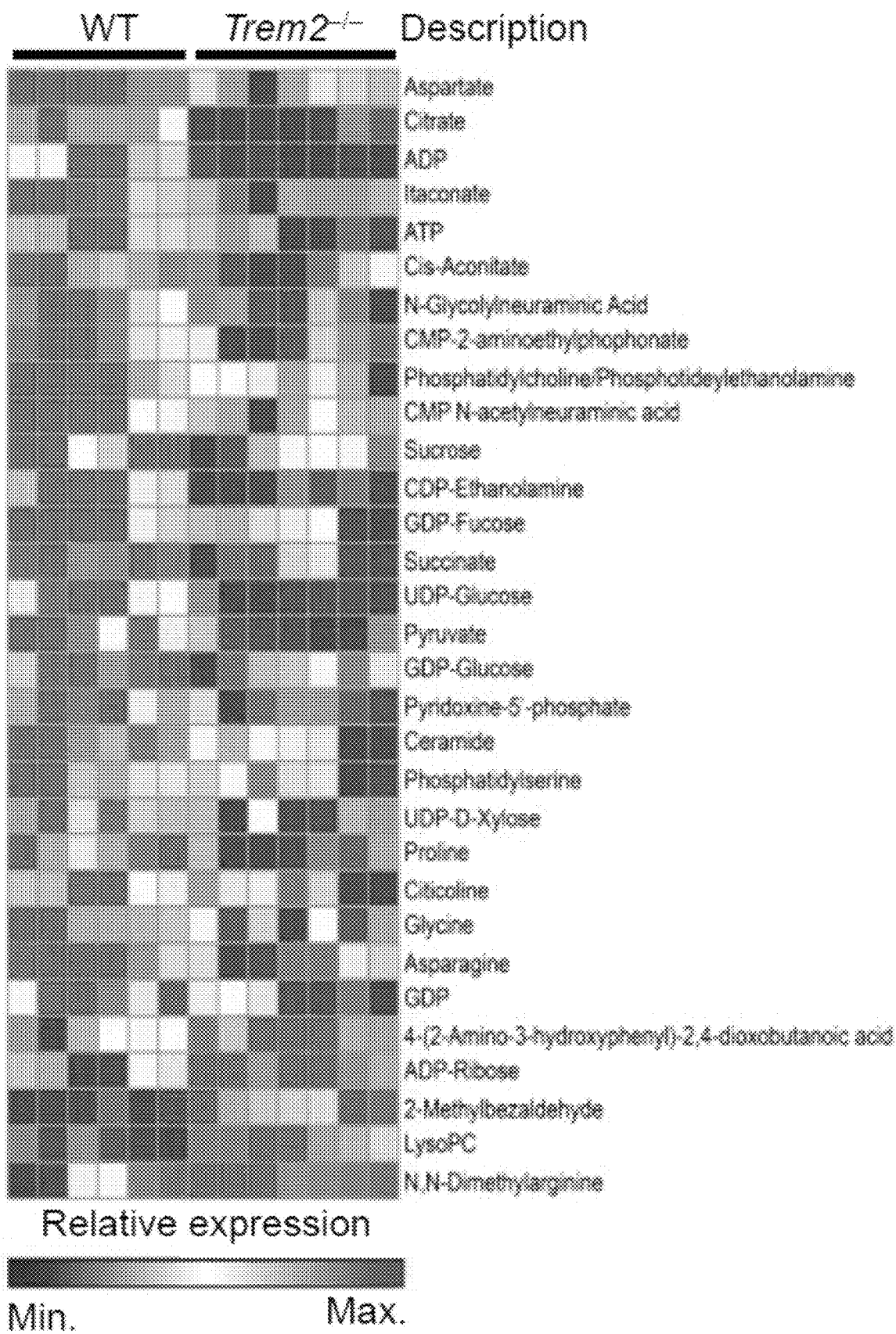
Figure 4D:
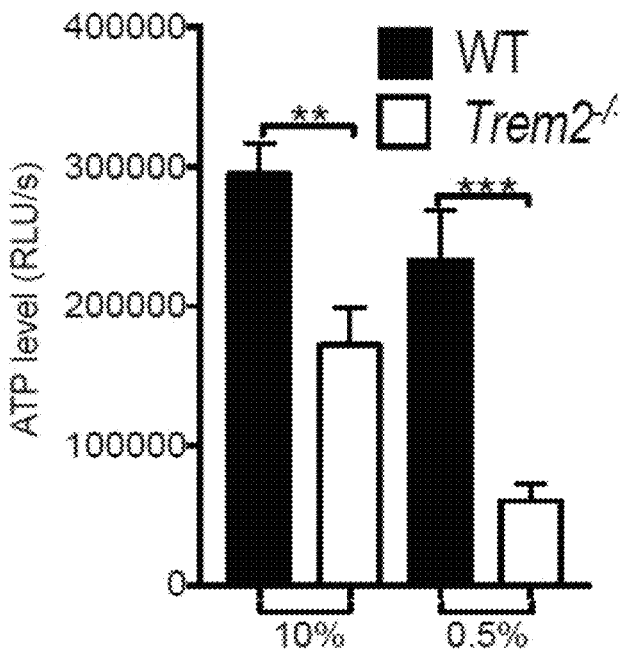
Figure 4E:
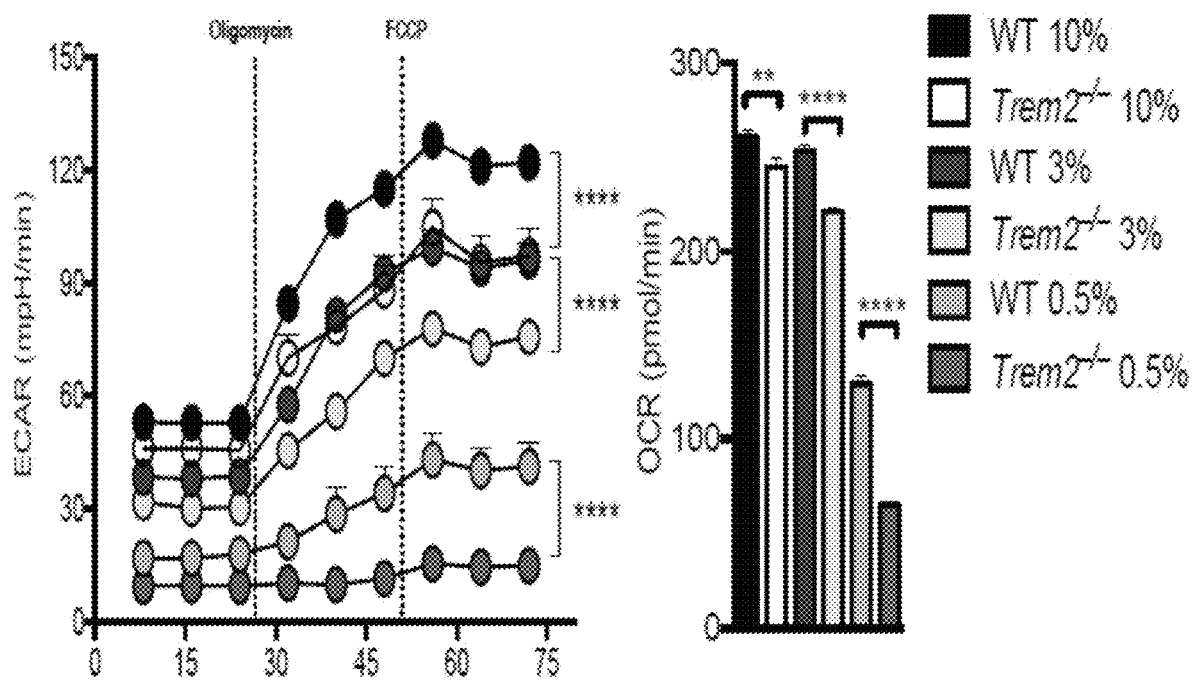
Figure 4F:
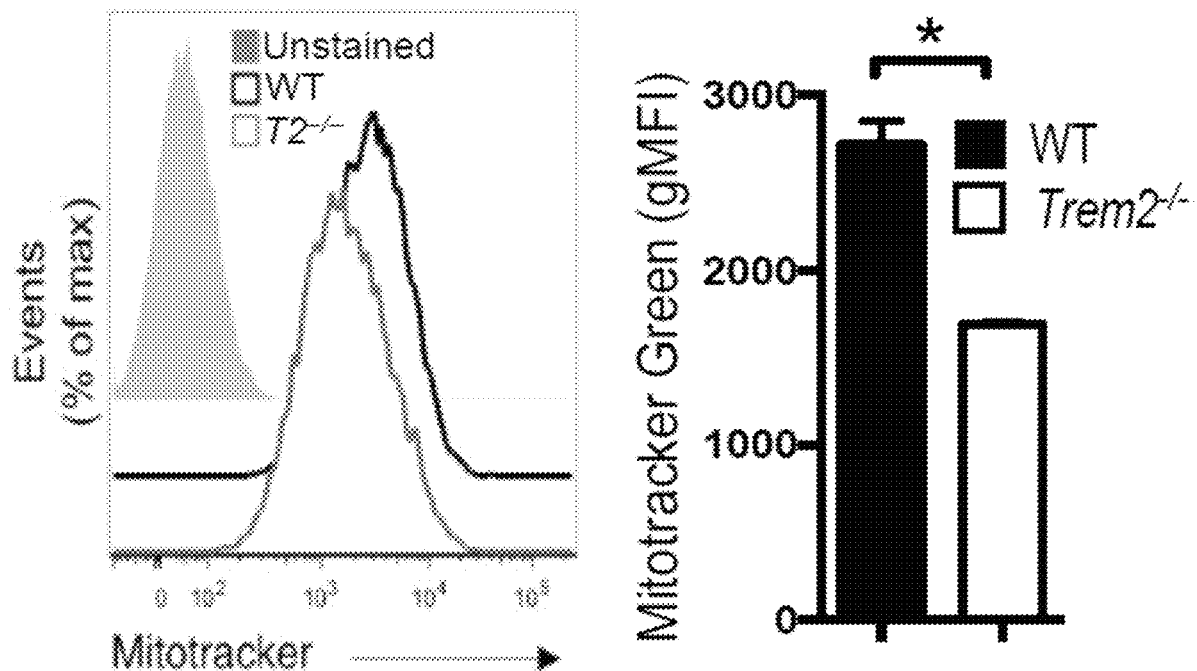
Figure 4G:
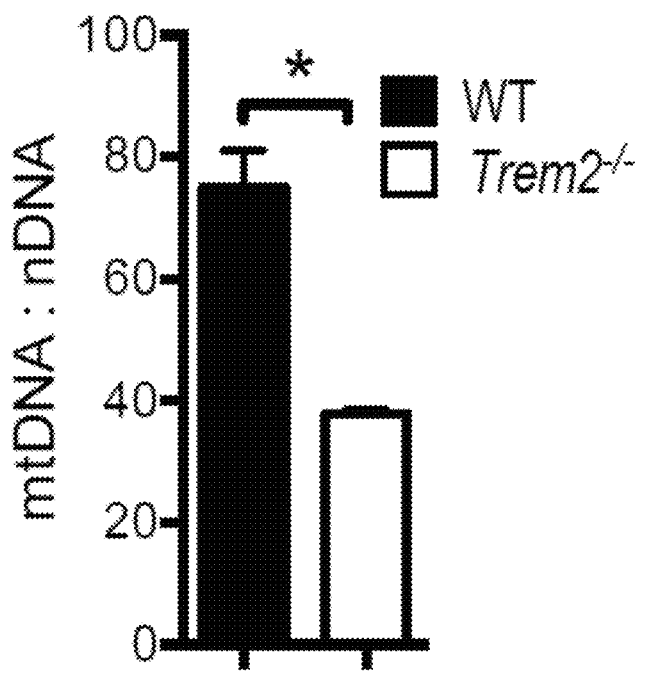

CSF-1 reduction further deteriorated energy and anabolic metabolism in Trem2$^{-/-}$ BMDMs. Under these conditions, again in comparison to WT BMDMs, Trem2$^{-/-}$ BMDMs underwent a marked increase in symmetrical dimethyl arginine, indicative of protein catabolism, as well as an increase in ADP-ribose, indicative of NAD degradation (FIG. 4C, FIG. 11B-FIG. 11C). Furthermore, stores of high-energy phosphates, such as phosphocreatine and ATP, were depleted in Trem2$^{-/-}$ BMDMs cultured in limiting CSF1 conditions (FIG. 11D). A luciferase-based ATP assay confirmed an ATP deficiency in Trem2$^{-/-}$ BMDMs, which was exacerbated at low CSF1 concentrations (FIG. 4D). We further assessed the energy metabolism of WT and Trem2$^{-/-}$ BMDMs using the Seahorse analyzer. A lower extracellular acidification rate (ECAR), indicative of less glycolytic flux, was noted in Trem2$^{-/-}$ BMDMs both at baseline and after induction of maximal glycolytic capacity by oligomycin and FCCP. This deficit widened relative to WT cells as the CSF1 concentration was reduced (FIG. 4E). Trem2$^{-/-}$ BMDMs had only a slightly reduced oxygen consumption rate (OCR) compared to WT BMDMs when cultured in standard CSF1 concentrations, indicating relatively intact oxidative phosphorylation; however, a deficit in OCR emerged as the CSF1 concentration was reduced (FIG. 4E). Trem2$^{-/-}$ BMDMs also had fewer mitochondria than WT BMDMs on a per cell basis as measured by MitoTracker Green fluorescence and by the mitochondrial-to-nuclear DNA ratio (FIG. 4F, FIG. 4G). These findings were not restricted to BMDMs, as resting and thioglycolate-elicited peritoneal TREM2-deficient macrophages also had a lower mitochondrial mass than did WT macrophages (FIG. 11E-FIG. 11H). Cultured adult primary Trem2$^{-/-}$ microglia recapitulated the deficiencies in energetic metabolism and mTOR signaling as well as autophagy observed in Trem2$^{-/-}$ BMDMs (FIG. 11I-FIG. 11M). Thus, lack of TREM2-mTOR signaling impairs the energy status and anabolism of BMDMs and other primary macrophages both in steady state and under energetic stress.

Example 5

Figure 5A:
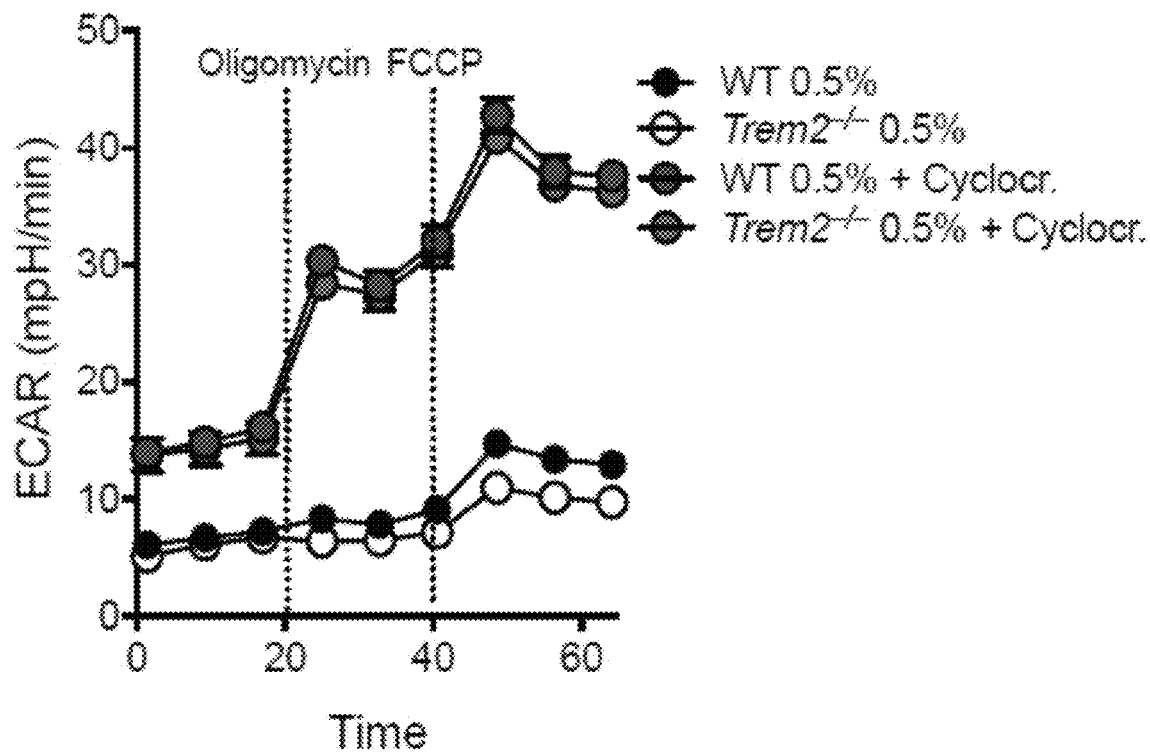
FIG. 5A, FIG. 5B, FIG. 5C, FIG. 5D, FIG. 5E, FIG. 5F and FIG. 5G depict enhanced energy storage or dectin-1 signaling can compensate for TREM2 deficiency.
Figure 5B:
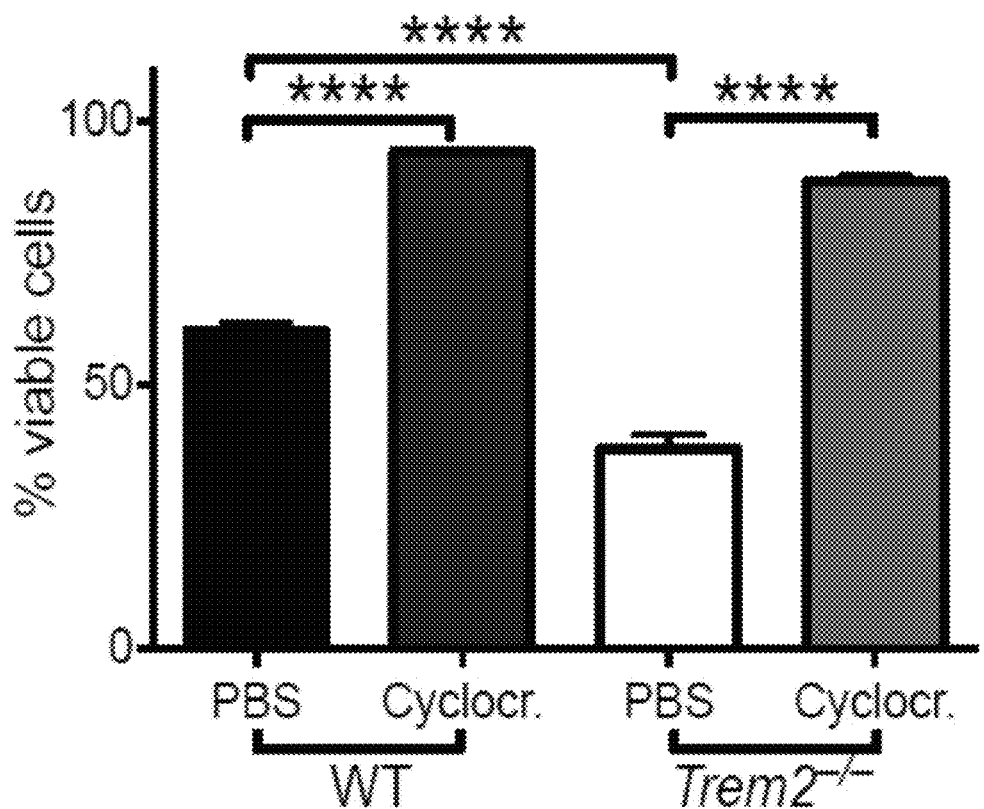
Figure 5C:
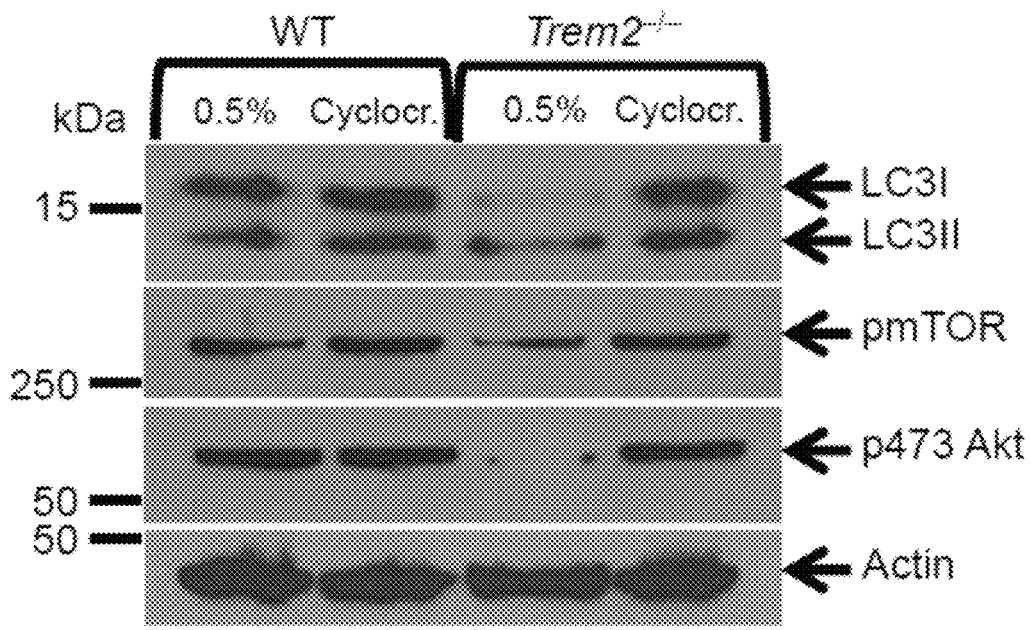

Enhanced Energy Storage or Dectin-1 Signaling Can Compensate for TREM2 Deficiency In Vitro Given the dramatic effect of TREM2 deficiency on mTOR activation and energy utilization in BMDMs, we tested whether bypassing TREM2 and directly compensating for these deficits by alternative means could restore the cellular energy status of Trem2$^{-/-}$ BMDMs. Muscle physiology studies have extensively demonstrated that creatine phosphate contributes to the regeneration of ATP and to the maintenance of uniformly high ATP/ADP ratios in muscle fibers (Walker, 1979). Moreover, the creatine analog 1-carboxymethyl-2-iminoimidazolidine (cyclocreatine) can, upon phosphorylation, generate a long-acting phosphagen that can effectively sustain cellular ATP levels during increased energy demand (Kurosawa et al., 2012; Woznicki and Walker, 1979). Thus, we tested whether addition of cyclocreatine to the culture medium could rescue energetic metabolism in Trem2-deficient BMDMs. Indeed, incubation with cyclocreatine improved ECAR, which was accompanied by less autophagy, increased mTOR signaling and viability (FIG. 5A-FIG. 5C and data not shown).

Figure 5D:
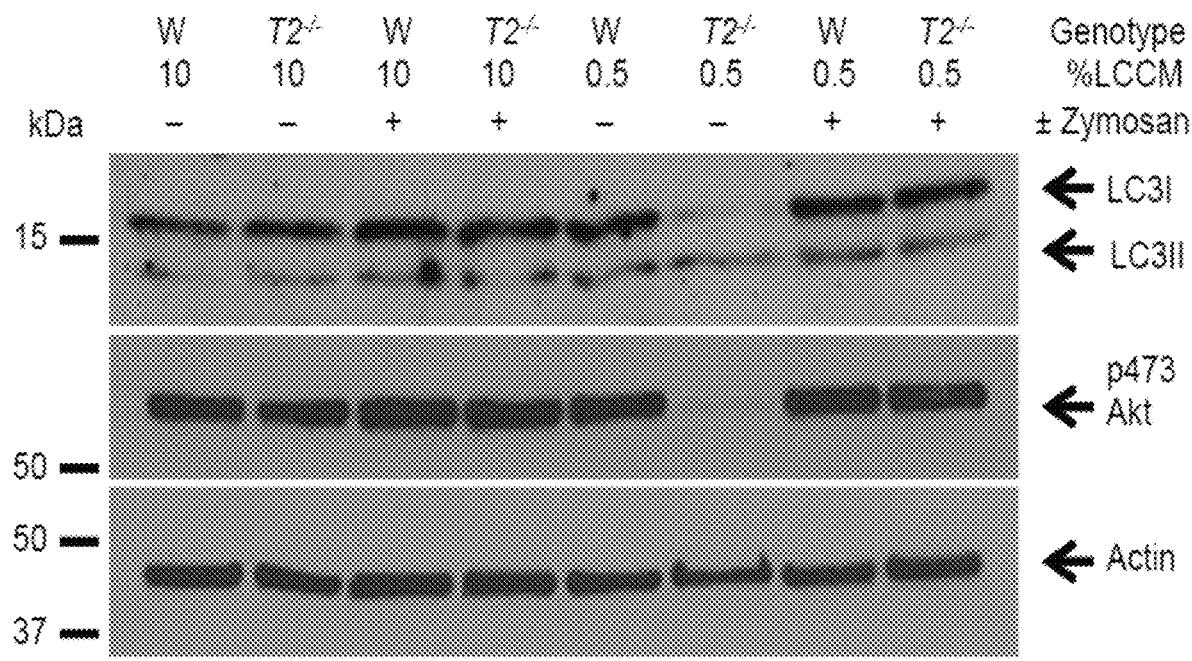
Figure 5E:
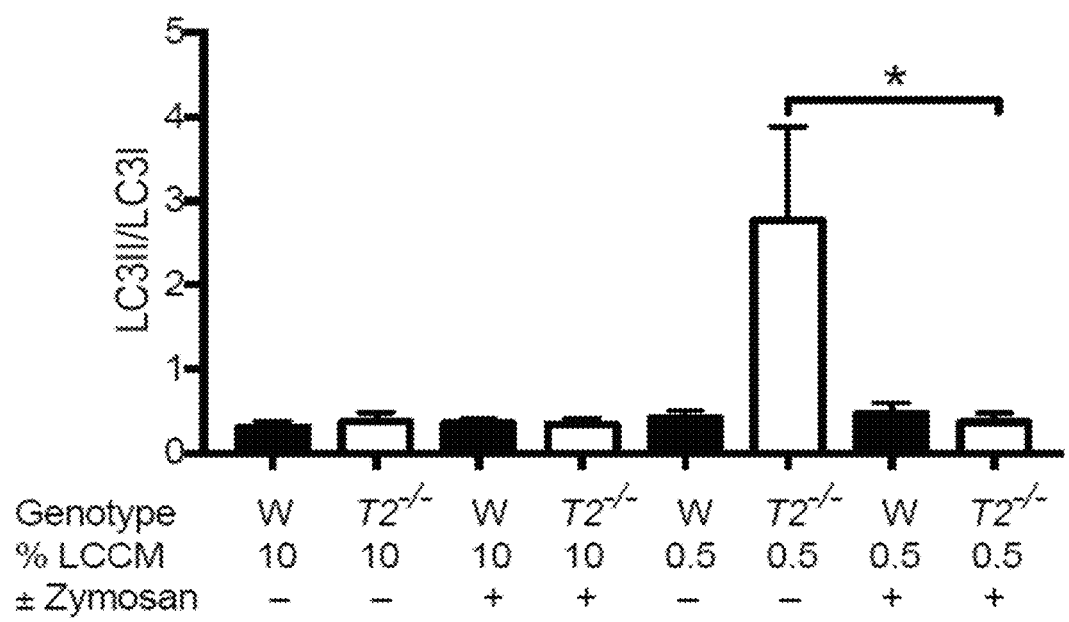
Figure 5F:
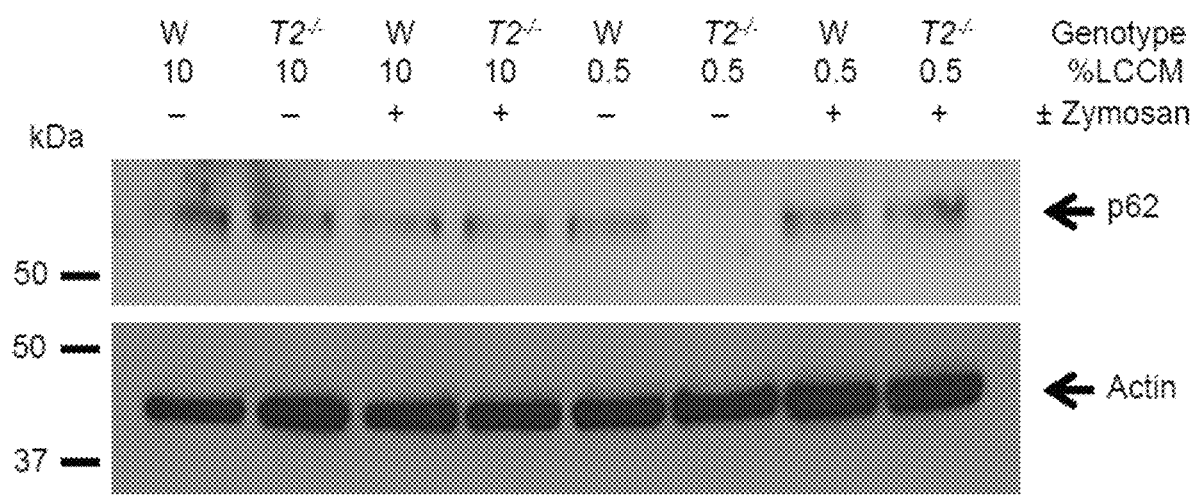
Figure 5G:
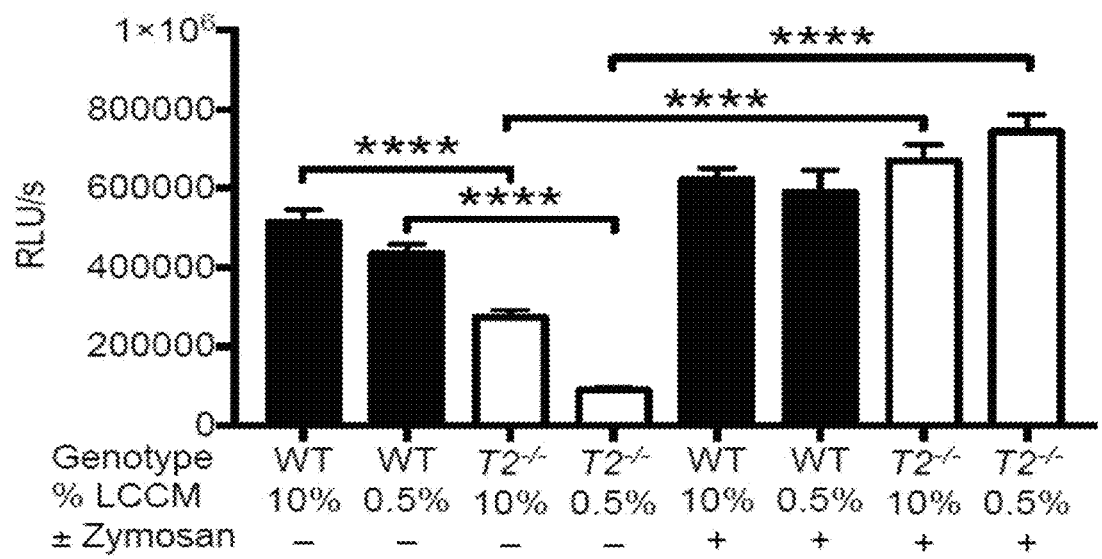

To test whether engagement of receptors that elicit signaling pathways similar to those of TREM2 could also mitigate autophagy and support cell survival, Trem2$^{-/-}$ and WT BMDMs were cultured with depleted zymosan, a selective ligand of dectin-1, which activates Syk and PI3K signaling independent of DAP12 (Dambuza and Brown, 2015). Dectin-1 activation curbed autophagy in CSF1-starved TREM2-deficient BMDMs to levels seen in WT BMDMs in low CSF-1, as indicated by a reduction in the LC3II/LC3I ratio (FIG. 5D, FIG. 5E) along with increased amounts of p62 (FIG. 5F). Treatment with zymosan also enhanced cellular ATP levels in Trem2$^{-/-}$ BMDMs, restoring them to WT BMDM levels. (FIG. 5G). Thus, alternative energetic and signaling pathways can compensate for lack of TREM2 signaling.

Example 6

Cyclocreatine Rescues Microgliosis and Clustering and Moderates Neurite Dystrophy In Vivo Because cyclocreatine rescued metabolism and viability and suppressed autophagy in Trem2$^{-/-}$ BMDMs in vitro and given previous studies showing that cyclocreatine is passively transported across membranes and can accumulate and function as a phosphagen in the mouse brain in vivo (Kurosawa et al., 2012), we asked whether dietary supplementation with cyclocreatine could rescue microglial function and suppress autophagy in vivo in Trem2$^{-/-}$ 5XFAD mice. The drinking water of 5XFAD and Trem2$^{-/-}$ 5XFAD mice was supplemented with cyclocreatine from 10 weeks of age until 8 months of age. Remarkably, significantly fewer multivesicular/multilamellar structures were seen by TEM in microglia in Trem2$^{-/-}$ 5XFAD mice treated with cyclocreatine than in microglia in untreated mice (FIG. 6A, FIG. 6B). Corroborating this with confocal microscopy, the percentage of LC3+ microglia, the number of LC3 puncta/cell, and the percentage of cleaved caspase-3+ microglia were all significantly decreased in Trem2$^{-/-}$ 5XFAD mice treated with cyclocreatine (FIG. 12B and FIG. 6C, FIG. 6E, FIG. 6F,). Furthermore, the number of microglia/high powered field (HPF) in plaque-bearing regions of the cortex and clustering of microglia around plaques were both significantly increased (FIG. 6C-FIG. 6D and FIG. 12A) in Trem2$^{-/-}$ 5XFAD mice treated with cyclocreatine compared to untreated Trem2$^{-/-}$ 5XFAD mice. These findings indicate that dietary supplementation with cyclocreatine is sufficient to partially rescue the defect in microgliosis and microglial clustering around plaques in Trem2$^{-/-}$ 5XFAD mice, while concomitantly mitigating autophagy and death of the microglia.

To assess the impact of cyclocreatine on microglial activation, which is also impaired in Trem2$^{-/-}$ 5XFAD mice, we quantified the percentage of microglia that expressed the microglial activation marker osteopontin (Spp1) in 5XFAD and Trem2$^{-/-}$ 5XFAD mice, a protein that, in the brain, is specifically upregulated in microglia in the context of Aβ deposition (Orre et al., 2014; Wang et al., 2015). Untreated Trem2$^{-/-}$ 5XFAD mice had very few Spp1+ microglia, while 5XFAD, cyclocreatine-treated 5XFAD, and cyclocreatine-treated Trem2$^{-/-}$ 5XFAD mice all had significantly more Spp1+ microglia (FIG. 7A, FIG. 7B). Moreover, biochemical analysis of microglia isolated ex vivo demonstrated that cyclocreatine treatment of Trem2$^{-/-}$ 5XFAD mice also restored microglial mTOR signaling and significantly limited autophagy compared to untreated Trem2$^{-/-}$ 5XFAD mice (FIG. 7C, FIG. 7D).

As a major function of TREM2 in vivo is enabling microglia to form a barrier around plaques that prevents spreading of Aβ fibrils and alleviates dystrophy of plaque-adjacent neurites (Wang et al., 2016; Yuan et al., 2016), we asked whether cyclocreatine treatment of Trem2$^{-/-}$ 5XFAD mice impacted plaque morphology and/or neuronal dystrophy. While plaques in untreated Trem2$^{-/-}$ 5XFAD mice had a lower density than those in 5XFAD mice as measured by methoxy-X04 staining intensity, the density of plaques in cyclocreatine treated Trem2$^{-/-}$ 5XFAD mice resembled that of plaques in 5XFAD mice (FIG. 7E), although plaque shape complexity was not significantly altered (FIG. 12K). Despite reducing plaque density, cyclocreatine did not moderate plaque accumulation or the engulfment of plaque particulates by microglia, at least at this time point (FIG. 12F-FIG. 12K). As APP is known to accumulate in dystrophic neurites, we used APP deposition in distinct rounded particles around plaques to assess neurite dystrophy (Masliah et al., 1996; Wang et al., 2016; Yuan et al., 2016). Cyclocreatine treatment of Trem2$^{-/-}$ 5XFAD mice significantly reduced plaque-associated neurite dystrophy compared to untreated Trem2$^{-/-}$ 5XFAD mice to levels observed in 5XFAD mice (FIG. 7F, FIG. 7G). Taken together, these data indicate that cyclocreatine administration improves microglial metabolism and the protective response to Aβ plaques in TREM2-deficient 5XFAD mice.

Discussion

Increasing evidence supports the hypothesis that the microglial response to AD lesions controls disease progression (Gold and El Khoury, 2015; Hong et al., 2016; Meyer-Luehmann and Prinz, 2015; Perry and Holmes, 2014; Tejera and Heneka, 2016; Wang et al., 2016; Yuan et al., 2016). Toll-like receptors and NOD-like receptors have been previously implicated in the microglia response to Aβ accumulation and shown to mediate an inflammatory response that contributes to pathology (Freeman and Ting, 2016; Heneka et al., 2015; Heneka et al., 2013). To sustain cytokine secretion, these receptors induce a striking metabolic reprogramming, which consists of a switch from fatty acid metabolism and oxidative phosphorylation to glycolysis (O'Neill and Pearce, 2016). In our study, TREM2 emerges as an innate immune receptor that impacts microglia metabolism in AD through a distinct mechanism, which consists of basic activation of mTOR signaling that supports long-term cell trophism, survival, growth, and proliferation, rather than drastic metabolic reprogramming. This function of TREM2 is reminiscent of the tonic function of the B cell antigen receptor in mature B cells, which delivers survival signals through PI3-K (Werner et al., 2010). Likewise, cell membrane phospholipids and lipoprotein particles may continuously engage TREM2, inducing tonic mTOR signaling through upstream activators, such as P I3-K, PDK1 and AKT, which are recruited by the TREM2-associated signaling subunits DAP12 and DAP10 (Ford and McVicar, 2009; Peng et al., 2010). This concept provides a unifying mechanism to explain the reported broad and long-term impact of TREM2 on diverse microglial functions, such as survival, proliferation, clustering around plaques, as well as phagocytosis of apoptotic cells and myelin debris (Jay et al., 2017; Neumann and Takahashi, 2007; Wang et al., 2015; Yeh et al., 2016; Yuan et al., 2016).

We found that the defective mTOR signaling in TREM2-deficient microglia is associated with a compensatory increase of autophagy in vitro and in vivo in AD. Reduced glycolysis and autophagy are known to attenuate inflammation (Netea-Maier et al., 2016) and, indeed, microglia from 5XFAD mice lacking TREM2 weakly express inflammatory mediators in comparison to microglia from 5XFAD mice (Wang et al., 2015). Moreover, autophagy may also enhance microglial clearance of Aβ (Cho et al., 2014; Lucin et al., 2013; Shibuya et al., 2014), as it does in neurons (Nara et al., 2006; Komatsu et al., 2006; Yang et al., 2011). However, a long-term defect in mTOR activation results in global microglial dysfunction, reduced cell viability and proliferation, as demonstrated by increased caspase-3 activation in microglia and by the previously reported increase in dying microglia around plaques in Trem2$^{-/-}$ 5XFAD mice (Wang et al., 2015). Thus, while increased autophagy may be beneficial in reducing inflammation and Aβ load in the short-term, a defect in mTOR signaling is detrimental and severely impairs microglia fitness and capacity to respond to Aβ accumulation in the long-term.

TREM2-deficient microglia have long been thought to improperly remain in a homeostatic state during neurodegenerative disease rather than responding appropriately to pathology, a paradigm that has been supported by transcriptomic analysis of these cells. However, for the first time, we demonstrate that on a biochemical and ultrastructural level, TREM2-deficient microglia adopt a severely divergent cellular state that does not reflect homeostasis during neurodegeneration, with a dramatic loss of mTOR signaling and robust induction of autophagy. These results suggest that TREM2-deficient microglia are not simply ignoring plaque pathology, but rather that they are being actively driven into a stressed state that is normally compensated by TREM2-dependent survival signals. An important implication of this finding is that microglia in a neurodegenerative environment probably receive not only positive activating signals but also negative cytotoxic signals. Thus, it may not be microglial activation per se that is required to protect against neurodegeneration, but rather avoidance of a dysfunctional, low-energy state induced by the disease. Based on our findings, previous reports of impaired microglial activation in a variety of settings may be due to either impaired recognition of activating signals or to impaired resistance to cytotoxic signals—two possibilities that can be distinguished by the strength of mTOR signaling. Counteracting such dysfunction by metabolic compensation may also represent a fundamentally distinct therapeutic approach.

Along these lines, our study shows that the defect in mTOR-mediated metabolic activation in TREM2-deficient cells can be corrected in vitro through the creatine kinase pathway or by triggering the dectin-1 pathway, which transmits intracellular signals similar to those of TREM2. Based on these results, we adopted a therapeutic strategy based on the use of cyclocreatine, an analog of creatine that crosses membranes, enters the brain (Woznicki and Walker, 1979), can be phosphorylated and dephosphorylated by creatine kinases (McLaughlin et al., 1972), and can generate a supply of ATP (Kurosawa et al., 2012). Remarkably, we found that administration of dietary cyclocreatine throughout the progression of Aβ accumulation improves microglia viability, numbers and clustering around Aβ plaques. As a result, plaques are denser and, most importantly, plaque-associated neurite dystrophy is greatly reduced. Although cyclocreatine treatment was not sufficient to reduce the overall Aβ plaque accumulation, this may depend on time point chosen for analysis and/or cyclocreatine dosage and duration of treatment. While the creatine kinase pathway has been previously recognized to play an important role in the CNS in neurotransmitter release, membrane potential maintenance, $Ca^{2+}$ homeostasis, and ion gradient restoration (Snow and Murphy, 2001; Wyss and Kaddurah-Daouk, 2000), our results indicate that this system may also be exploited for sustaining microglial metabolism. It should be noted that in certain settings cyclocreatine can inhibit creatine kinase and can also have systemic effects such as alteration in pancreatic hormones and glucose metabolism (Ara et al., 1998; Kuiper et al., 2008). As this is the case and creatine and creatine analogs like cyclocreatine are available over the counter for use we must emphasize that these findings are the result of proof of principal studies and we do not advise the use cyclocreatine as a preventative treatment for AD. Future studies will be required to precisely define the mechanisms through which cyclocreatine impacts microglial responses to Aβ. Additionally, it will be important to determine whether cyclocreatine has any impact on proteolytic shedding of TREM2 from microglia, which results in the release of soluble TREM2 with potential pro-survival functions. Altogether, our study provides proof of principle that strategies aimed at sustaining microglial metabolism may be promising for therapeutic intervention in AD and other neurodegenerative diseases linked to TREM2 deficiency and microglial dysfunction in general.

Experimental Model and Subject Details
Mice.

Mice were of mixed sexes. Mice within experiments were age and sex matched. For studies using 5XFAD and Trem2$^{-/-}$ 5XFAD animals all animals were 8 months of age at the time of use. For bone marrow and primary microglia mice were used from 6 weeks of age until 12 weeks of age. Mice used in this study include WT C57BL/6J, 5XFAD, Trem2$^{-/-}$, and Trem2$^{-/-}$ 5XFAD animals. All animals were backcrossed until at least >98% C57BL/6J confirmed by genotype wide microsatellite typing. Mice were housed under specific pathogen free conditions. Mice from different genotypes were cohoused. Mice did not undergo any procedures prior to their stated use. For cyclocreatine treatment mixed litters of sex matched mice were randomly assigned to experimental groups. All studies performed on mice were done in accordance with the Institutional Animal Care and Use Committee at Washington University in St. Louis approved all protocols used in this study.

Human Post-Mortem Samples.

Characteristics of donors of human post-mortem brain tissue at the time of collection is indicated in Table 1. Samples from 7 R47H, 4 R62H, and 8 case matched AD patients were examined. Samples were obtained from the Knight Alzheimer's Disease Research Center at Washington University. Protocol numbers: Healthy Aging and Senile Dementia (NASD) Morphology Core: 89-0555 and Program Project: Alzheimer's Disease Research Center (ADRC): 89-0556.

Cell Lines and Primary Cells.

Bone marrow derived macrophages and microglia were prepared from sex and age matched mice. To prepare bone marrow-derived macrophages, femurs and tibias were removed and flushed with PBS. Cells were counted and plated at $2.5 \times 10^6$ cells/100 mm petri dish in RPMI supplemented with Glutamax, penicillin/streptomycin, non-essential amino acids, pyruvate, and 10% heat inactivated fetal bovine serum (complete RPMI) and 10% L-cell conditioned medium (LCCM). Cells were cultured for 4-5 days before use. Microglia were prepared as previously described (Wang et al., 2015). Briefly, brains were dissociated by using a Neural Tissue Dissociation Kit (T) (Miltenyi Biotech Cat. Number 130-093-231). Cells suspensions were labeled with anti-mouse CD45 magnetic beads and isolated on LS columns (Miltenyi Biotic). Cells were plated onto poly-L-lysine coated polystyrene plates in complete RPMI supplemented with 20% LCCM and 10 ng/ml human TGF-β. Media was changed on day 3 post plating and cells were used 5-7 days post plating.

Trem2 reporter cells were maintained in 10% FBS in RPMI-1640 supplemented with sodium pyruvate, GlutaMAX, and penicillin/streptomycin. Trem2 reporter cells were based on the 2B4 NFAT-GFP cells developed by Arase et al. (Arase et al., 2002). The sex of the mouse from which 2B4 t-cell hybridoma cells were derived has not been reported (Arase et al., 2002; Hedrick et al., 1982).

Method Details
Mice.

The generation of Trem2$^{-/-}$ and Trem2$^{-/-}$ 5XFAD mice has been described previously (Oakley et al., 2006; Turnbull et al., 2006; Wang et al., 2015). All mice were on a C57BL/6 background. Age and sex matched mice were used for all experiments; experimental cohorts of mice were cohoused from birth to control for the microbiota. For in vivo cyclocreatine treatment 10-week old mice were put on cyclocreatine-containing water, treatment was continued until mice reached 8 months of age (Santa Cruz SC-217964 S). Desired intake of cyclocreatine was approximately 0.28 mg/g of body weight/day, which is approximately the same as the standard creatine dose used in humans of 285 mg/kg of body weight/day (Kurosawa et al., 2012). Cyclocreatine was administered in drinking water at a final concentration of 2.33 mg/ml. The Institutional Animal Care and Use Committee at Washington University in St. Louis approved all protocols used in this study.

Human Post-Mortem Brain Tissue.

Paraffin-embedded sections (8 um) from the frontal cortex of individuals carrying the common variant (CV) of TREM2 (8) or heterozygous for the CV and either R47H (7), R62H (4) were obtained from the Knight Alzheimer's Disease Research Center at Washington University. Protocol numbers: Healthy Aging and Senile Dementia (NASD) Morphology Core: 89-0555 and Program Project: Alzheimer's Disease Research Center (ADRC): 89-0556. R47H and R62H carriers were case matched for age, gender, and CERAD-Reagan plaque score to CV TREM2 control individuals. Detailed demographic characteristics are provided in Table 1.

Immunohistochemistry of Human Post-Mortem Brain Tissue.

Brain sections were deparaffinized with xylene and rehydrated with decreasing concentrations of ethanol. Antigen retrieval was performed by incubating sections for 20 minutes in a 95° C. citrate buffer bath (10 mM sodium citrate, 0.05% Tween-20, pH 6.0) prior to staining. Sections were blocked in 3% goat serum in PBS for 30 minutes at room temperature (RT) followed by incubation with rabbit anti-Iba1 (1:250, Wako; catalog no. 019-19741) overnight at 4° C. Sections were washed in PBS and incubated for 1 hour at room temperature (RT) with methoxy-XO4 (20 µg/ml) (Tocris Bioscience #4920) and anti-rabbit DyLight 549 (Vector Laboratories DI-1549). Sections were washed and incubated overnight in anti-LC3A/B Alexa Fluor 488 (Cell Signaling Technologies #13082). Sections were washed and mounted using Fluoromount G (SouthernBiotech #0100-01) and images were collected using a Nikon A1Rsi+ confocal microscope. Images were then processed with Imaris 7.7 (Bitplane).

Cell Culture and Biochemical Assays.

To prepare bone marrow-derived macrophages, femurs and tibias were removed and flushed with PBS. Cells were counted and plated at $2.5 \times 10^6$ cells/100 mm petri dish in RPMI supplemented with Glutamax, penicillin/streptomycin, non-essential amino acids, pyruvate, and 10% heat inactivated fetal bovine serum (complete RPMI) and 10% L-cell conditioned medium (LCCM). Cells were cultured for 4-5 days before use. Microglia were prepared as previously described (Wang et al., 2015). Briefly, brains were dissociated by using a Neural Tissue Dissociation Kit (T) (Miltenyi Biotech Cat. Number 130-093-231). Cell suspensions were labeled with anti-mouse CD45 magnetic beads and isolated on LS columns (Miltenyi Biotic). Cells were plated onto poly-L-lysine coated polystyrene plates in complete RPMI supplemented with 20% LCCM and 10 ng/ml human TGF-β. Media was changed on day 3 post plating and cells were used 5-7 days post plating. ATP concentrations were determined with an ATP Determination Kit (Invitrogen).

Microglia Sorting.

Microglia were isolated from the indicated animals as previously described (Wang et al., 2015). CD45$^+$, CD11 b$^+$, F4/80$^+$ (Biolegend Cat. Number 103134, eBioscience Cat. Numbers 11-0112 and 17-4801) cells in the brain were fluorescence-activated cell-sorted (FACS) directly into RLT-plus lysis buffer for microarray or 2% FBS in PBS for TEM or immunoblot lysates. For microarray RNA extraction was performed using a RNeasy micro kit (QIAGEN). Microarray hybridization (Affymetrix MoGene 1.0 ST array) and data processing were performed at the Washington University Genome Center. For normalization, raw data was processed by Robust Multi-Array (RMA) method and genes were pre-filtered for expression value ≥120 expression units, a cut-off above which genes have a 95% chance of expression demonstrated in Immgen data set, which uses the same array platform(Wang et al., 2015). QIAGEN IPA analysis was performed by comparing fold change and p-values for all genes SXFAD and Trem2-deficient SXFAD microglia. Heatmaps and hierarchical clustering were generated from preselected gene-lists using Morpheus. Microarray data has been deposited at GEO:GSE65067.

Immunoblotting.

BMDM or microglia were lysed in RIPA buffer (50 mM Tris, 150 mM NaCl, 1% SDS, and 1% Triton X100) containing PMSF, leupeptin, activated sodium orthovanidate, apoprotinin, and phosphatase inhibitor cocktail 3 (Sigma Aldrich Cat. Number P0044). Lysates were flash frozen on dry ice and stored at −80° C. until use. Lysates were thawed and 4× LDS running buffer and 10% β-mercaptoethanol were added. Lysates were heated to 95° C. for 10 minutes and run on either a 15% polyacrylamide gel with a 4% stacking gel, a 12% bis-tris gel (Nupage), or a 4-12% bis-tris gel (Nupage). Proteins were transferred to nitrocellulose and blocked for 1 hour at RT in 5% milk in Tris buffered saline with 0.05% Tween 20 (TBST). Membranes were incubated in primary antibody overnight at 4° C. . Membranes were subsequently washed and incubated in Lienco anti-rabbit HRP for 1 hour at RT, washed, and developed using either SuperSignal West Pico Chemiluminescent Substrate or a combination of SuperSignal West Pico Chemiluminescent Substrate and SuperSignal West Femto Chem iluminescent Substrate.

Metabolite Profiling by EIS-MS/MS.

BMDMs were cultured in either 0.5% or 10% LCCM overnight in complete RPMI. Polar metabolites were extracted according to General Metabolics protocol for extraction of polar metabolites from adherent mammalian cell culture. Briefly, cells were washed in pre-warmed 75 mM ammonium carbonate in water. Metabolites were extracted by addition of 70° C. 70% ethanol for 3 minutes. Ethanol was removed and plates were washed with additional 70° C. 70% ethanol. Debris was pelleted by spinning at 14,000 rpm in a tabletop microcentrifuge for 10 minutes at 4° C. Extracts were moved to a fresh tube and shipped to General Metabolics for assessment by EIS-MS/MS. Differential expression analysis was done using limma.

RNA-Seq Analysis.

Cells were cultured as described in the metabolite profiling by EIS-MS/MS section above. mRNA was extracted from cell lysates using oligo-dT beads (Invitrogen). For cDNA synthesis, we used custom oligo-dT primer with a barcode and adaptor-linker sequence (CCTA-CACGACGCTCTTCCGATCT-XXXXXXXX-T15)(SEQ ID NO:1). After first-strand synthesis, samples were pooled together based on Actb qPCR values and RNA-DNA hybrids were degraded with consecutive acid-alkali treatment. Subsequently, a second sequencing linker (AGATCG-GAAGAGCACACGTCTG)(SEQ ID NO:2) was ligated with T4 ligase (NEB) followed by SPRI-beads (Agencourt AMPure XP, BeckmanCoulter) clean-up. The mixture was enriched by PCR for 12 cycles and SPRI-beads (Agencourt AMPure XP, BeckmanCoulter) purified to yield final strand-specific RNA-seq libraries. Libraries were sequenced using a HiSeq 2500 (Illumina) using 50 bp×25 bp pair-end sequencing. Second read (read-mate) was used for sample demultiplexing. Reads were aligned to the GRCm38.p2 assembly of mouse genome using STAR aligner. Aligned reads were quantified using quant3p script to account for specifics of 3' sequencing. RefSeq genome annotation was used and DESeq2 was used for differential gene expression analysis. RNAseq data has been deposited at GEO: GSE98563.

Network Analysis.

Network analysis was performed as previously described utilizing Shiny GAM (Sergushichev et al., 2016; Vincent et al., 2015). We considered a network of chemical mappings between carbon atoms in substrates and products for all annotated reactions in KEGG database using RPAIRs entries. The scores for nodes and edges were assigned according to log(p-value), such that highly significant gene or metabolite signals had positive scores and not significant had negative scores. Using an exact solver we found a module with a maximal weight, with counting positive scores maximum once for a measured entity (a mass-spectrometry peak or a gene). For clarity, addition edges between nodes in the module were added if the corresponding gene was highly expressed (was in a top 3000 expressed genes).

qRT-PCR.

Total RNA was isolated with TRIzol Reagent (Invitrogen) and single-strand cDNA was synthesized with a High Capacity cDNA Reverse Transcription Kit (Applied Biosystems). Genomic DNA was extracted using the QIAamp DNA micro kit (Qiagen) to determine mtDNA/nDNA ratios. Real-time PCR was performed using SYBR Green real-time PCR master mix (Thermo-Fisher) and LightCycler 96 detection system (Roche). mtDNA primers were to cytochrome c oxidase subunit 1 and nDNA primers were to NADH: ubiquinone oxidoreductase core subunit V1.

Metabolism Assays.

For real-time analysis of extracellular acidification rates (ECAR) macrophages were analyzed using an XF96 Extracellular Flux Analyzer (Agilent Technologies). Cells were incubated overnight in complete RPMI in the indicated concentration of LCCM with or without cyclocreatine (10 mM). Measurements were taken under basal conditions and following the sequential addition of 1 µM oligomycin and 1.5 µM fluoro-carbonyl cyanide phenylhydrazone (FCCP) (purchased from Sigma-Aldrich).

Transmission Electron Microscopy.

For ultrastructural analyses, cells were fixed in 2% paraformaldehyde/2.5% glutaraldehyde in 100 mM sodium cacodylate buffer, pH 7.2 for 1 hr at RT (Polysciences Inc., Warrington, Pa.). Samples were washed in sodium cacodylate buffer and postfixed in 1% osmium tetroxide for 1 hr (Polysciences Inc.). Samples were then rinsed extensively in deionized water prior to en bloc staining with 1% aqueous uranyl acetate for 1 hr (Ted Pella Inc., Redding, CA). Following several rinses in $dH_2O$, samples were dehydrated in a graded series of ethanol and embedded in Eponate 12 resin (Ted Pella Inc.). Sections of 95 nm were cut with a Leica Ultracut UCT ultramicrotome (Leica Microsystems Inc., Bannockburn, Ill.), stained with uranyl acetate and lead citrate, and viewed on a JEOL 1200 EX transmission electron microscope (JEOL USA Inc., Peabody, MA) equipped with an AMT 8 megapixel digital camera and AMT Image Capture Engine V602 software (Advanced Microscopy Techniques, Woburn, MA).

For quantitation of multivesicular/multilamellar structures, 30 cells that were cross-sectioned through the nucleus (indicating cross-section through the middle of cell) were randomly chosen, and images of each cell were taken at 6,000× and 20,000× magnification. The cross-sectional area of each of the multivesicular structures were determined using Image J 1.38 g (National Institutes of Health, USA, customized for AMT images). Data is expressed as the 1) total number of a multivesicular/multilammelar structures per cross-sectional area of cytosol and 2) the total cross-sectional area of multivesicular/multilamellar structures per area of cytosol.

Preparation of Brain Samples and Confocal Microscopy.

Confocal microscopy analysis was performed as previously described (Wang et al., 2015). Briefly, mice were anesthetized with ketamine/xylazine and perfused with ice-cold PBS containing 1 U/ml of heparin. Brains were fixed in 4% PFA overnight at 4° C. rinsed in PBS and incubated overnight at 4° C. in 30% sucrose before freezing in a 2:1 mixture of 30% sucrose and optimal cutting temperature compound. Serial 40 µm coronal sections were cut on a cryo-sliding microtome. Floating sections from 1.1 mm Bregma to 0.8 mm Bregma for cortical imaging or slides with fixed human sections were stained with lba-1 (Waco Chemicals Cat. Number 019-19741) overnight at 4° C. followed by staining with anti-rabbit IgG DyLight 549 (Vector Laboratories Cat. Number DI-1549) and methoxy-X04 (Tocris Cat. Number 4920) for 1 hour at RT. Finally, sections were stained for with anti-LC3 Alexa 488±anti-cleaved caspase 3 (Cell Signaling Technologies Cat. Number 13082 and 9602). Images were collected using a Nikon A1 Rsi+ confocal microscope. Images were then processed with Imaris 7.7 (Bitplane).

Microglia Clustering Analysis.

Positions of microglia and positions and volumes of plaques within z-stacks were derived from analysis in Imaris, and microglia-plaque association was determined using automated scripts in Matlab. Briefly, each plaque in the z-stack was modeled as an idealized sphere with the same volume and center of mass. Microglia density within 15 µm of the plaque surface was determined by isolating the voxels of the image that fall within 15 µm of the edge of the idealized plaque. The number of microglia contained in these voxels was divided by the total volume of those voxels to obtain density for a single plaque. Densities of all plaques in a z-stack were averaged together, and the resulting values were averaged together for all z-stacks corresponding to a single animal.

Reporter Cell Assay.

The 2B4 T cell hybridoma cell line was retrovirally transduced with an NFAT-GFP reporter construct, and TREM2 reporter cells were generated by a second retroviral transduction with a TREM2 overexpression construct and selected by puromycin resistance, as previously described (Wang et al., 2015). Cells were cultured routinely in complete media (10% FBS in RPMI-1640 supplemented with sodium pyruvate, GlutaMAX, and penicillin/streptomycin). For serum starvation, cells were plated at a density of 25,000 cells/well in a 96-well plate in either complete media or RPMI-1640 in the presence of 20% anti-TREM2 hybridoma supernatant (clone M178, generated in house) or 20% isotype control hybridoma supernatant (Wang et al., 2015). After 16 hours, the percent of GFP+ cells among live cells was measured by flow cytometry.

Quantification of Methoxy-X04 Coverage.

To measure total plaque area, brain sections were stained with methoxy X04. Images were collected using a Nikon Eclipse 80i microscope. For quantitative analysis, images were converted to 8-bit greyscale and stitched using the "Stitching" plugin in ImageJ. Cortex (~1.1 mm Bregma to 0.8 mm Bregma) and hippocampus (~−1.7 Bregma to −2.4 Bregma) were determined by manual selection. The threshold of selected images were set at 1.5× mean intensity of the selected area to highlight plaques and analyzed using the "Measure" function in ImageJ to calculate the percent area covered. Identified objects after thresholding were individually inspected to confirm the object as a plaque or not. Two brain sections per mouse were used for quantification. The average of two sections was used to represent a plaque load for each mouse.

Plaque Morphology Analysis.

Methoxy-X04-stained sections were imaged by confocal microscopy using a 60× objective and 1.5× digital zoom in the cortex at ~1.1 mm Bregma to 0.8 mm Bregma. Z images were taken at 1.2 µm intervals. 20-30 µm z-stacks were z-projected by maximum intensity projection and individual plaques were selected in ImageJ. Each individual plaque was traced using a combination of thresholds and edge detection and smoothened using image erosion. The average intensity was determined by averaging values of pixels within the plaque trace. The shape index was calculated as $4\pi*$(perimeter pixels)$^2$/(all pixels).

Quantification and Statistical Analysis

Data in FIG.s are presented as mean±SEM. Unless otherwise stated statistical analysis was performed using Prism (GraphPad). Quantification of confocal microscopy, immunoblots, and electron microscopy images were performed using Imaris, ImageJ, Matlab, and FIJI. Differential metabolite expression was analyzed using limma. Pathway analysis of microarray data was performed using IPA software. RNAseq analysis was performed by using Second read (read-mate) for sample demultiplexing. Reads were aligned using STAR aligner and quantified using quant3p script. RefSeq genome annotation was used and DESeq2 was used for differential gene expression analysis. Combined RNAseq and metabolite network analysis was performed utilizing Shiny GAM. Statistical analysis to compare the mean values for multiple groups was performed using Prism by one-way ANOVA with Holm-Sidak's multiple comparisons test. Comparison of two groups was performed in Prism using a two-tailed unpaired t-test (Mann Whitney). Values were accepted as significant if P≤0.05. Intragroup variation compared between groups was similar in all experiments.

Data and Software Availability

Microarray data has been deposited at GEO:GSE65067.
RNAseq data has been deposited at GEO:GSE98563.

TABLE 2

KEY RESOURCES TABLE

| REAGENT or RESOURCE | SOURCE | IDENTIFIER |
|---|---|---|
| Antibodies | | |
| anti-Pan Actin | Cell Signaling Technologies | Cat# 4968 |
| anti-p62 | Cell Signaling Technologies | Cat# 8025 |
| anti-phospho Akt 473 | Cell Signaling Technologies | Cat# 9271 |
| anti-phospho Ulk1 317 | Cell Signaling Technologies | Cat# 12753 |
| anti-phospho Ulk1 757 | Cell Signaling Technologies | Cat# 6888 |
| anti-phospho NDRG1 | Cell Signaling Technologies | Cat# 3217 |
| anti-phospho S6K | Cell Signaling Technologies | Cat# 2710 |
| anti-phospho 4EBP1 | Cell Signaling Technologies | Cat# 2855 |
| anti-Akt | Cell Signaling Technologies | Cat# 9272 |
| anti-S6K | Cell Signaling Technologies | Cat# 9202 |
| anti-phospho AMPKα | Cell Signaling Technologies | Cat# 2535 |
| anti-AMPKα | Cell Signaling Technologies | Cat# 5832 |
| anti-LC3 | Cell Signaling Technologies | Cat# 4108 |
| anti-phospho mTOR 2448 | Cell Signaling Technologies | Cat# 2971 |
| anti-Spp1 | R and D Systems | Cat# AF808 |
| anti-Xbp-1s | BD Biosciences | Cat# 562642 |
| anti-Iba1 | Wako | Cat# 019-19741 |
| anti-cleaved caspase-3 Alexa 647 | Cell Signaling Technologies | Cat# 9602 |
| anti-LC3 488 | Cell Signaling Technologies | Cat# 13082 |

TABLE 2-continued

KEY RESOURCES TABLE

| REAGENT or RESOURCE | SOURCE | IDENTIFIER |
| --- | --- | --- |
| anti-APP | Milipore | Cat# MAB348 |
| anti-CD45 BV421 | Biolegend | Cat# 103134 |
| anti-CD11b FITC | eBioscience | Cat# 11-0112 |
| anti-F4/80 APC | eBioscience | Cat# 17-4801 |
| anti-Trem2 | Colonna Lab | M1178 doi: 10.1016/j.cell.2015.01.049. |
| anti-rabbit DyLight 549 | Vector Laboratories | Cat# DI-1549 |
| Bacterial and Virus Strains | | |
| Murine Trem2 expressed in pMXs-IRES-Puro Retroviral Expression Vector | Cell Biolabs | https://www.cellbiolabs.com/pmxs-ires-puro-retroviral-expression-vector |
| Biological Samples | | |
| Human brain tissue for Alzheimer's disease patients (TREM2$^{CV/CV}$ (8), TREM2$^{cv/R47H}$ (7), TREM2$^{CV/R62H}$ (4)) | Knight Alzheimer's Disease Research Center at Washington University | Protocol numbers: Healthy Aging and Senile Dementia (NASD) Morphology Core: 89-0555 and Program Project: Alzheimer's Disease Research Center (ADRC): 89-0556. |
| Chemicals, Peptides, and Recombinant Proteins | | |
| Cyclocreatine | Santa Cruz Biotechnology | Cat# SC-217964 S |
| Methoxy X04 | Tocris Biosciences | Cat# 4920 |
| MitoTraker Green | Invitrogen | Cat# M7514 |
| Wortmannin | Millipore | Cat# 12-338 |
| Ly294002 | Calbiochem | Cat# 440202 |
| Tunicamycin | Sigma-Aldrich | Cat# 654380 |
| Bafilomycin A1 from *Streptomyces griseus* | Sigma-Aldrich | Cat# B1793-10UG |
| ToPro3 Iodide | Life Technologies | Cat# T3605 |
| Zymosan, depleted | Invivogen | Cat# tlrl-zyd |
| Oligomycin | Cayman Chemical | Cat# 11341 |
| FCCP | Cayman Chemical | Cat# 370865 |
| Critical Commercial Assays | | |
| ATP Assay | Invitrogen | Cat# A22066 |
| Neural Tissue Dissociation Kit (T) | Miltenyi Biotech | Cat# 130-093-231 |
| Deposited Data | | |
| GEO/GSE65067 | Microarray data | |
| GEO/GSE98563 | RNAseq data | |

TABLE 2-continued

KEY RESOURCES TABLE

| REAGENT or RESOURCE | SOURCE | IDENTIFIER |
|---|---|---|
| Experimental Models: Cell Lines | | |
| 2B4 cells retrovirally transduced with an NFAT-GFP reporter and retrovirally transduced with TREM2 | Generated in the laboratory of Dr. Marco Colonna. | doi: 10.1016/j.cell.2015.01.049. |
| 2B4 cells expressing NFAT-GFP | Generated in the laboratory of Dr. Lewis Lanier | doi: 10.1126/science.1070884 |
| Experimental Models: Organisms/Strains | | |
| Mouse: C57BL/6J WT | The Jackson Laboratory | Cat# 000664 |
| Mouse: 5XFAD/Tg6799 | The Jackson Laboratory | Cat# 34840-JAX |
| Mouse: Trem2$^{-/-}$ | Generated in the Laboratory of Dr. Marco Colonna | |
| Oligonucleotides | | |
| For nuclear DNA | FW: CTTCCCCACTGGCCTCAAG (SEQ ID NO: 3) RV: CCAAAACCCAGTGATCCAGC (SEQ ID NO: 4) | |
| For mitochondrial DNA | FW: TGCTAGCCGCAGGCATTAC (SEQ ID NO: 5) RV: GGGTGCCCAAAGAATCAGAAC (SEQ ID NO: 6) | |
| For beta-Actin (RNAseq) | FW: GGA GGG GGT TGA GGT GTT (SEQ ID NO: 7) RV: TGT GCA CTT TTA TTG GTC TCA AG (SEQ ID NO: 8) | |
| Linker primers for RNAseq | CCTACACGACGCTCTT CCGATCT-XXXXXXXX-T15 (SEQ ID NO: 1) AGATCGGAAGAGCACA CGTCTG (SEQ ID NO: 2) | |
| Recombinant DNA Software and Algorithms | | |
| Matlab | MathWorks | |
| Morpheus | Broad Institute | |
| Prism7 | Graphpad | |
| Fiji 2.0 | ImageJ | |
| Imaris 7.7 | Bitplane | |
| IPA | QIAGEN | |
| Shiny GAM | https://artyomovlab.wustl.edu/shiny/gam/ | |
| Other | | |
| XF96 Extracellular Flux Analyzer | Agilent | |
| Nikon A1Rsi Confocal Microscope | Nikon | |

REFERENCES

1. Ara, G., Gravelin, L. M., Kaddurah-Daouk, R., and Teicher, B.A. (1998). Antitumor activity of creatine analogs produced by alterations in pancreatic hormones and glucose metabolism. In vivo 12, 223-231.
2. Arase, H., Mocarski, E. S., Campbell, A. E., Hill, A. B., and Lanier, L. L. (2002). Direct recognition of cytomegalovirus by activating and inhibitory NK cell receptors. Science 296, 1323-1326.
3. Atagi, Y., Liu, C. C., Painter, M. M., Chen, X. F., Verbeeck, C., Zheng, H., Li, X., Rademakers, R., Kang, S. S., Xu, H., et al. (2015). Apolipoprotein E is a Ligand for Triggering Receptor Expressed on Myeloid Cells 2 (TREM2). J. Biochem.
4. Bailey, C. C., DeVaux, L. B., and Farzan, M. (2015). The Triggering Receptor Expressed on Myeloid Cells 2 Binds Apolipoprotein E. J. Biochem.
5. Cho, M. H., Cho, K., Kang, H. J., Jeon, E. Y., Kim, H. S., Kwon, H. J., Kim, H. M., Kim, D. H., and Yoon, S. Y. (2014). Autophagy in microglia degrades extracellular beta-amyloid fibrils and regulates the NLRP3 inflammasome. Autophagy 10, 1761-1775.
6. Dambuza, I. M., and Brown, G. D. (2015). C-type lectins in immunity: recent developments. Curr. Opin. Immunol. 32, 21-27.
7. Ford, J. W., and McVicar, D. W. (2009). TREM and TREM-like receptors in inflammation and disease. Curr. Opin. Immunol. 21, 38-46.
8. Freeman, L. C., and Ting, J. P. (2016). The pathogenic role of the inflammasome in neurodegenerative diseases. J. Neurochem. 136 Suppl 1, 29-38.
9. Galluzzi, L., Pietrocola, F., Levine, B., and Kroemer, G. (2014). Metabolic control of autophagy. Cell 159, 1263-1276.
10. Gold, M., and El Khoury, J. (2015). beta-amyloid, microglia, and the inflammasome in Alzheimer's disease. Semin. Immunopathol. 37, 607-611.
11. Guerreiro, R., and Hardy, J. (2014). Genetics of Alzheimer's disease. Neurotherapeutics 11, 732-737.
12. Hara, T., Nakamura, K., Matsui, M., Yamamoto, A., Nakahara, Y., Suzuki-Migishima, R., Yokoyama, M., Mishima, K., Saito, I., Okano, H., et al. (2006). Suppression of basal autophagy in neural cells causes neurodegenerative disease in mice. Nature 441, 885-889.
13. Hedrick, S. M., Matis, L. A., Hecht, T. T., Samelson, L. E., Longo, D. L., Heber-Katz, E., and Schwartz, R. H. (1982). The fine specificity of antigen and Ia determinant recognition by T cell hybridoma clones specific for pigeon cytochrome c. Cell 30, 141-152.
14. Heneka, M. T., Golenbock, D. T., and Latz, E. (2015). Innate immunity in Alzheimer's disease. Nat. Immunol. 16, 229-236.
15. Heneka, M. T., Kummer, M. P., Stutz, A., Delekate, A., Schwartz, S., Vieira-Saecker, A., Griep, A., Axt, D., Remus, A., Tzeng, T. C., et al. (2013). NLRP3 is activated in Alzheimer's disease and contributes to pathology in APP/PS1 mice. Nature 493, 674-678.
16. Holtzman, D. M., Morris, J. C., and Goate, A. M. (2011). Alzheimer's disease: the challenge of the second century. Sci. Transl. Med. 3, 77sr71.
17. Hong, S., Beja-Glasser, V. F., Nfonoyim, B. M., Frouin, A., Li, S., Ramakrishnan, S., Merry, K. M., Shi, Q., Rosenthal, A., Barres, B. A., et al. (2016). Complement and microglia mediate early synapse loss in Alzheimer mouse models. Science 352, 712-716.
18. Huang, Y., and Mucke, L. (2012). Alzheimer mechanisms and therapeutic strategies. Cell 148, 1204-1222.
19. Jay, T. R., Hirsch, A. M., Broihier, M. L., Miller, C. M., Neilson, L. E., Ransohoff, R. M., Lamb, B. T., and Landreth, G. E. (2017). Disease Progression-Dependent Effects of TREM2 Deficiency in a Mouse Model of Alzheimer's Disease. J. Neurosci. 37, 637-647.
20. Kim, J., Kundu, M., Viollet, B., and Guan, K. L. (2011). AMPK and mTOR regulate autophagy through direct phosphorylation of Ulk1. Nat. Cell Biol. 13, 132-141.
21. Klionsky, D. J., Abdelmohsen, K., Abe, A., Abedin, M. J., Abeliovich, H., Acevedo Arozena, A., Adachi, H., Adams, C. M., Adams, P. D., Adeli, K., et al. (2016). Guidelines for the use and interpretation of assays for monitoring autophagy (3rd edition). Autophagy 12, 1-222.
22. Komatsu, M., Waguri, S., Chiba, T., Murata, S., Iwata, J., Tanida, I., Ueno, T., Koike, M., Uchiyama, Y., Kominami, E., et al. (2006). Loss of autophagy in the central nervous system causes neurodegeneration in mice. Nature 441, 880-884.
23. Kroemer, G., Marino, G., and Levine, B. (2010). Autophagy and the integrated stress response. Mol. Cell 40, 280-293.
24. Kuiper, J. W., Pluk, H., Oerlemans, F., van Leeuwen, F. N., de Lange, F., Fransen, J., and Wieringa, B. (2008). Creatine kinase-mediated ATP supply fuels actin-based events in phagocytosis. PLoS biology 6, e51.
25. Kurosawa, Y., Degrauw, T. J., Lindquist, D. M., Blanco, V. M., Pyne-Geithman, G. J., Daikoku, T., Chambers, J. B., Benoit, S. C., and Clark, J. F. (2012). Cyclocreatine treatment improves cognition in mice with creatine transporter deficiency. J. Clin. Invest. 122, 2837-2846.
26. Laplante, M., and Sabatini, D. M. (2012). mTOR signaling in growth control and disease. Cell 149, 274-293.
27. Lucin, K. M., O'Brien, C. E., Bieri, G., Czirr, E., Mosher, K. I., Abbey, R. J., Mastroeni, D. F., Rogers, J., Spencer, B., Masliah, E., et al. (2013). Microglial beclin 1 regulates retromer trafficking and phagocytosis and is impaired in Alzheimer's disease. Neuron 79, 873-886.
28. Masliah, E., Sisk, A., Mallory, M., Mucke, L., Schenk, D., and Games, D. (1996). Comparison of neurodegenerative pathology in transgenic mice overexpressing V717F beta-amyloid precursor protein and Alzheimer's disease. J. Neurosci 16, 5795-5811.
29. McLaughlin, A. C., Cohn, M., and Kenyon, G. L. (1972). Specificity of creatine kinase for guanidino substrates. Kinetic and proton nuclear magnetic relaxation rate studies. J. Biol. Chem. 247, 4382-4388.
30. Meyer-Luehmann, M., and Prinz, M. (2015). Myeloid cells in Alzheimer's disease: culprits, victims or innocent bystanders? Trends in neurosciences 38, 659-668.
31. Netea-Maier, R. T., Plantinga, T. S., van de Veerdonk, F. L., Smit, J. W., and Netea, M. G. (2016). Modulation of inflammation by autophagy: Consequences for human disease. Autophagy 12, 245-260.
32. Neumann, H., and Takahashi, K. (2007). Essential role of the microglial triggering receptor expressed on myeloid cells-2 (TREM2) for central nervous tissue immune homeostasis. J. Neuroimmunol. 184, 92-99.

33. O'Neill, L. A., and Pearce, E. J. (2016). Immunometabolism governs dendritic cell and macrophage function. J. Exp. Med. 213, 15-23.

34. Oakley, H., Cole, S. L., Logan, S., Maus, E., Shao, P., Craft, J., Guillozet-Bongaarts, A., Ohno, M., Disterhoft, J., Van Eldik, L., et al. (2006). Intraneuronal beta-amyloid aggregates, neurodegeneration, and neuron loss in transgenic mice with five familial Alzheimer's disease mutations: potential factors in amyloid plaque formation. J. Neurosci. 26, 10129-10140.

35. Orre, M., Kamphuis, W., Osborn, L. M., Jansen, A. H., Kooijman, L., Bossers, K., and Hol, E. M. (2014). Isolation of glia from Alzheimer's mice reveals inflammation and dysfunction. Neurobiol. Aging 35, 2746-2760.

36. Peng, Q., Malhotra, S., Torchia, J. A., Kerr, W. G., Coggeshall, K. M., and Humphrey, M. B. (2010). TREM2- and DAP12-dependent activation of PI3K requires DAP10 and is inhibited by SHIP1. Sci. Signal. 3, ra38.

37. Perry, V.H., and Holmes, C. (2014). Microglial priming in neurodegenerative disease. Nat. Rev. Neurol. 10, 217-224.

38. Saxton, R. A., and Sabatini, D. M. (2017). mTOR Signaling in Growth, Metabolism, and Disease. Cell 168, 960-976.

39. Sergushichev, A. A., Loboda, A. A., Jha, A. K., Vincent, E. E., Driggers, E. M., Jones, R. G., Pearce, E. J., and Artyomov, M. N. (2016). GAM: a web-service for integrated transcriptional and metabolic network analysis. Nucleic Acids Res. 44, W194-200.

40. Shibuya, Y., Chang, C. C., Huang, L. H., Bryleva, E. Y., and Chang, T. Y. (2014). Inhibiting ACAT1/SOAT1 in microglia stimulates autophagy-mediated lysosomal proteolysis and increases Abeta1-42 clearance. The Journal of neuroscience : the official journal of the Society for Neuroscience 34, 14484-14501.

41. Snow, R. J., and Murphy, R. M. (2001). Creatine and the creatine transporter: a review. Mol. Cell. Biochem. 224, 169-181.

42. Tanzi, R.E. (2012). The genetics of Alzheimer disease. Cold Spring Harb. Perspect. Med. 2.

43. Tejera, D., and Heneka, M. T. (2016). Microglia in Alzheimer's disease: the good, the bad and the ugly. Curr. Alzheimer Res. 13, 370-380.

44. Turnbull, I. ., Gilfillan, S., Cella, M., Aoshi, T., Miller, M., Piccio, L., Hernandez, M., and Colonna, M. (2006). Cutting edge: TREM-2 attenuates macrophage activation. J. Immunol. 177, 3520-3524.

45. Ulrich, J. D., Finn, M. B., Wang, Y., Shen, A., Mahan, T. E., Jiang, H., Stewart, F. R., Piccio, L., Colonna, M., and Holtzman, D. M. (2014). Altered microglial response to Abeta plaques in APPPS1-21 mice heterozygous for TREM2. Mol. Neurodegener. 9, 20.

46. Vincent, E.E., Sergushichev, A., Griss, T., Gingras, M. C., Samborska, B., Ntimbane, T., Coelho, P. P., Blagih, J., Raissi, T. C., Choiniere, L., et al. (2015). Mitochondrial Phosphoenolpyruvate Carboxykinase Regulates Metabolic Adaptation and Enables Glucose-Independent Tumor Growth. Mol. Cell 60, 195-207.

47. Walker, J. B. (1979). Creatine: biosynthesis, regulation, and function. Adv. Enzymol. Relat. Areas Mol. Biol. 50, 177-242.

48. Wang, Y., Cella, M., Mallinson, K., Ulrich, J. D., Young, K. L., Robinette, M. L., Gilfillan, S., Krishnan, G. M., Sudhakar, S., Zinselmeyer, B. H., et al. (2015). TREM2 lipid sensing sustains the microglial response in an Alzheimer's disease model. Cell 160, 1061-1071.

49. Wang, Y., Ulland, T. K., Ulrich, J. D., Song, W., Tzaferis, J. A., Hole, J. T., Yuan, P., Mahan, T. E., Shi, Y., Gilfillan, S., et al. (2016). TREM2-mediated early microglial response limits diffusion and toxicity of amyloid plaques. J. Exp. Med. 213, 667-675.

50. Werner, M., Hobeika, E., and Jumaa, H. (2010). Role of PI3K in the generation and survival of B cells. Immunol. Rev. 237, 55-71.

51. Woznicki, D. T., and Walker, J. B. (1979). Formation of a supplemental long time-constant reservoir of high energy phosphate by brain in vivo and in vitro and its reversible depletion by potassium depolarization. J. Neurochem. 33, 75-80.

52. Wyss, M., and Kaddurah-Daouk, R. (2000). Creatine and creatinine metabolism. Physiol. Rev. 80, 1107-1213.

53. Yang, D. S., Stavrides, P., Mohan, P. S., Kaushik, S., Kumar, A., Ohno, M., Schmidt, S. D., Wesson, D., Bandyopadhyay, U., Jiang, Y., et al. (2011). Reversal of autophagy dysfunction in the TgCRND8 mouse model of Alzheimer's disease ameliorates amyloid pathologies and memory deficits. Brain: a journal of neurology 134, 258-277.

54. Yeh, F. L., Wang, Y., Tom, I., Gonzalez, L. C., and Sheng, M. (2016). TREM2 Binds to Apolipoproteins, Including APOE and CLU/APOJ, and Thereby Facilitates Uptake of Amyloid-Beta by Microglia. Neuron 91, 328-340.

55. Yuan, P., Condello, C., Keene, C. D., Wang, Y., Bird, T. D., Paul, S. M., Luo, W., Colonna, M., Baddeley, D., and Grutzendler, J. (2016). TREM2 Haplodeficiency in Mice and Humans Impairs the Microglia Barrier Function Leading to Decreased Amyloid Compaction and Severe Axonal Dystrophy. Neuron 90, 724-739.

All cited references are herein expressly incorporated by reference in their entirety.

Whereas particular embodiments have been described above for purposes of illustration, it will be appreciated by those skilled in the art that numerous variations of the details may be made without departing from the disclosure as described in the appended claims.

What is claimed is:

1. A method for treating a microglial dysfunction-associated neurodegenerative disease in a subject in need thereof, the method comprising:
   administering to the subject a therapeutically effective amount of a composition comprising a microglial rescuing agent, wherein the microglial rescuing agent is cyclocreatine or a pharmaceutically acceptable salt thereof;
   wherein the microglial dysfunction-associated neurodegenerative disease is a neurodegenerative disease characterized by SNPs or mutations effecting a TREM2 variant or an ApoE variant, resulting in decreased microglial activity; and
   wherein the microglial dysfunction-associated neurodegenerative disease is Alzheimer's disease.

2. The method of claim 1, wherein the microglial dysfunction-associated neurodegenerative disease is characterized by single nucleotide polymorphisms (SNPs) or mutation in Trem2 or ApoE affecting microglial activity.

3. The method of claim 1, wherein a therapeutically effective amount of a microglial rescuing agent results in one or more of improved microglial metabolic activity, decreased microglial autophagy, reduced neurite dystrophy, decreased cell death, improved microglia viability or improved microglia numbers.

4. The method of claim 1, wherein the therapeutically effective amount of a microglia) rescuing agent results in improved microglia clustering around plaques or reduced plaque-associated neurite dystrophy.

5. The method of claim 1, wherein the subject is human.

6. A method of treating at least one symptom of cognitive dysfunction in a subject having a microglial dysfunction-associated neurodegenerative disease, wherein the microglial dysfunction-associated neurodegenerative disease is a neurodegenerative disease characterized by SNPs or mutations effecting a TREM2 variant or an ApoE variant, resulting in decreased microglial activity, the method comprising:
   administering to the subject a therapeutically effective amount of a composition comprising a microglial rescuing agent, wherein the microglial rescuing agent is cyclocreatine or a pharmaceutically acceptable salt thereof; and
   wherein the microglial dysfunction-associated neurodegenerative disease is Alzheimer's disease.

7. The method of claim 6, wherein at least one symptom comprises short term memory function.

8. The method of claim 6, wherein the at least one symptom comprises a spatial learning dysfunction.

9. The method of claim 6, wherein the subject is human.

* * * * *